(12) United States Patent
Matsuo et al.

(10) Patent No.: US 7,879,766 B2
(45) Date of Patent: Feb. 1, 2011

(54) METHOD OF PREPARING A SUGAR CHAIN LIBRARY AND USE THEREOF

(75) Inventors: Ichiro Matsuo, Wako (JP); Yukishige Ito, Wako (JP)

(73) Assignee: RIKEN, Saitama (JP)

( * ) Notice: Subject to any disclaimer, the term of this patent is extended or adjusted under 35 U.S.C. 154(b) by 500 days.

(21) Appl. No.: 11/723,933

(22) Filed: Mar. 22, 2007

(65) Prior Publication Data

US 2007/0254344 A1 Nov. 1, 2007

(30) Foreign Application Priority Data

Apr. 27, 2006 (JP) ............... 2006-124468

(51) Int. Cl.
C12N 9/24 (2006.01)
C07H 1/00 (2006.01)
C07H 3/00 (2006.01)
C12P 19/18 (2006.01)

(52) U.S. Cl. ............... 506/19; 435/97; 435/200; 536/123; 536/123.1

(58) Field of Classification Search ............ None
See application file for complete search history.

(56) References Cited

PUBLICATIONS

Matsuo (Jun. 13, 2005 Tetrahedron Letters vol. 46 p. 4197).*
Kajihara Y, Suzuki Y, Yamamoto N, Sasaki K, Sakakibara T, Juneja LR. Prompt chemoenzymatic synthesis of diverse complex-type oligosaccharides and its application to the solid-phase synthesis of a glycopeptide with Asn-linked sialyl-undeca- and asialo-nonasaccharides. Chemistry. Feb. 20, 2004;10(4):971-85.

* cited by examiner

Primary Examiner—Jeffrey S Lundgren
Assistant Examiner—Christian Boesen
(74) Attorney, Agent, or Firm—Wenderoth, Lind & Ponack, L.L.P.

(57) ABSTRACT

The present invention provides methods which enables synthesis of various sugar chains and products obtained by the same. More specifically, the present invention provides protected sugar chain compounds represented by the formula (I) below:

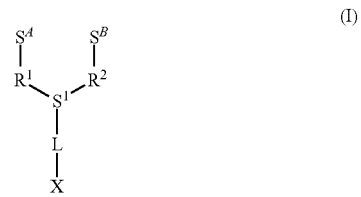

(I)

[wherein $R^1$ and $R^2$ are the same or different and each is a linear or branched sugar chain, $S^1$ is any sugar residue, $S^A$ and $S^B$ are the same or different sugar residues, L is a bond or a linear sugar chain, X is absent, or, if present, represents certain group, the sugar residues $S^A$ and $S^B$ are cleaved by different exoglycosidases, respectively] and libraries thereof, and methods of producing the same; methods of producing a sugar chain compound, which comprises treating the sugar chain compound or library with glycosidase, and glycosidase decomposition products obtained by the same; intermediates for the synthesis of protected sugar chain compounds; reagents and kits; and the like.

15 Claims, 22 Drawing Sheets

METHOD OF PREPARING A SUGAR CHAIN LIBRARY AND USE THEREOF

FIELD OF THE INVENTION

The present invention relates to protected sugar chain compounds, a library thereof, and a method of producing the same; a method of producing sugar chain compounds, which comprises treating protected sugar chain compounds and a library thereof with glycosidases, and glycosidase decomposition products thereof; intermediates for the synthesis of protected sugar chain compounds; a reagent and kit comprising protected sugar chain compounds and a library thereof, and the like.

BACKGROUND ART

In recent years, mechanisms for quality control of nascent proteins based on interactions between sugar chains and intracellular lectin/molecular chaperones have been drawing attention as a subject of active research worldwide in the field of sugar chain biology. In the rough endoplasmic reticulum, the majority of proteins are modified by a tetradecasaccharide consisting of three glucose units, nine mannose units, and two N-acetylglucosamine units (Glc3Man9GlcNAc2). Such protein-bound sugar chains are decomposed by glycosidases, resulting in the formation of a dodecasaccharide (GlcMan9GlcNAc2; see below). This is followed by trimming of the sugar chain moieties by glycohydrolases; it is postulated that there exists a lectin-like protein that accurately recognizes the various sugar chain structures and polypeptide moieties resulting in this trimming process, which protein acts to deliver other proteins in the correct higher-order structure to Golgi body, to retain immature proteins in the endoplasmic reticulum until they assume the correct higher-order structure, and to direct faulty proteins failing to assume the correct higher-order structure to endoplasmic reticulum-related decomposition. Hence, it is considered that in the endoplasmic reticulum, protein quality control takes place through confounding interactions between sugar chains and glucosidases, glucose transferases, the lectin-like protein and the like.

The Structure of High Mannose Type Sugar Chain (GlcMan9GlcNAc2)

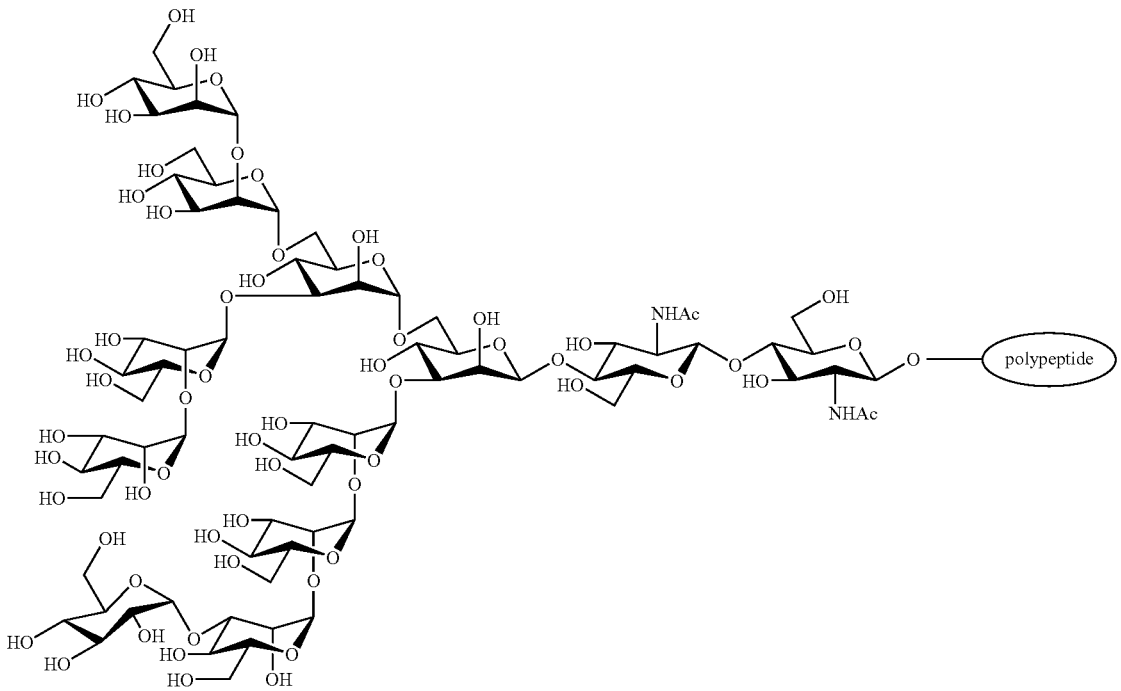

The Schematic Structure of High Mannose Type Sugar Chain (GlcMan9GlcNAc2)

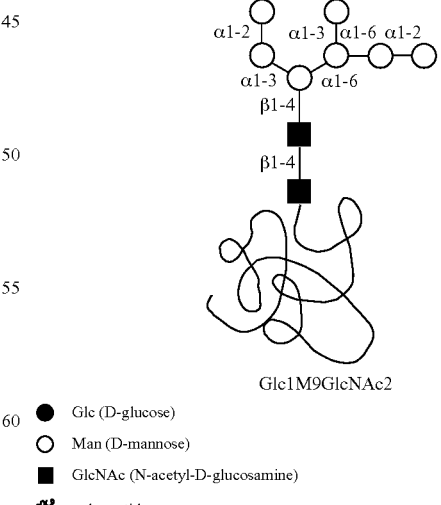

Glc1M9GlcNAc2

● Glc (D-glucose)
○ Man (D-mannose)
■ GlcNAc (N-acetyl-D-glucosamine)
🙢 polypeptide Currently, thanks to technical improvements in sugar chain separation and analysis, an increasing variety of sugar chain samples are available from naturally occurring products. It is difficult, however, to purify from a natural product a desired sugar chain (e.g., the sugar chains resulting from glycosidase decomposition of high mannose type sugar chain, shown below) in a sufficient amount to enable its application to sugar chain functional analysis, or to various products and methods. Hence, there is a demand for the development of a method that enables easier obtainment of various naturally occurring sugar chains (sugar chain library).

The Structures of Naturally Occurring Sugar Chains Generated from High Mannose Type Sugar Chain (GlcMan9GlcNAc2)

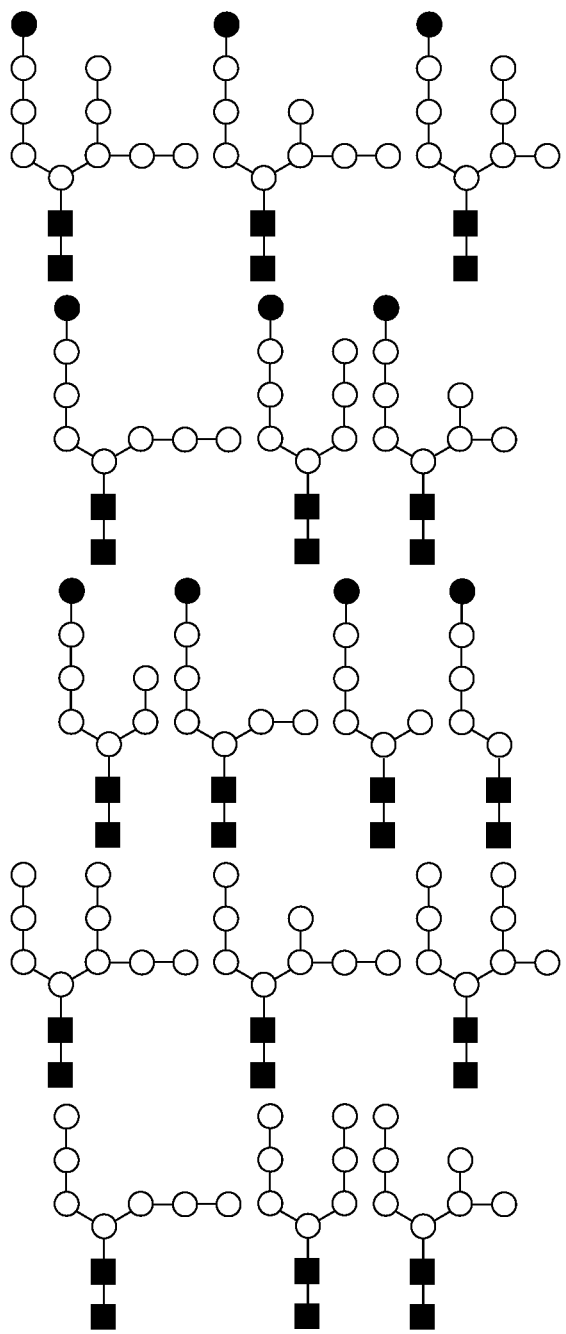

-continued

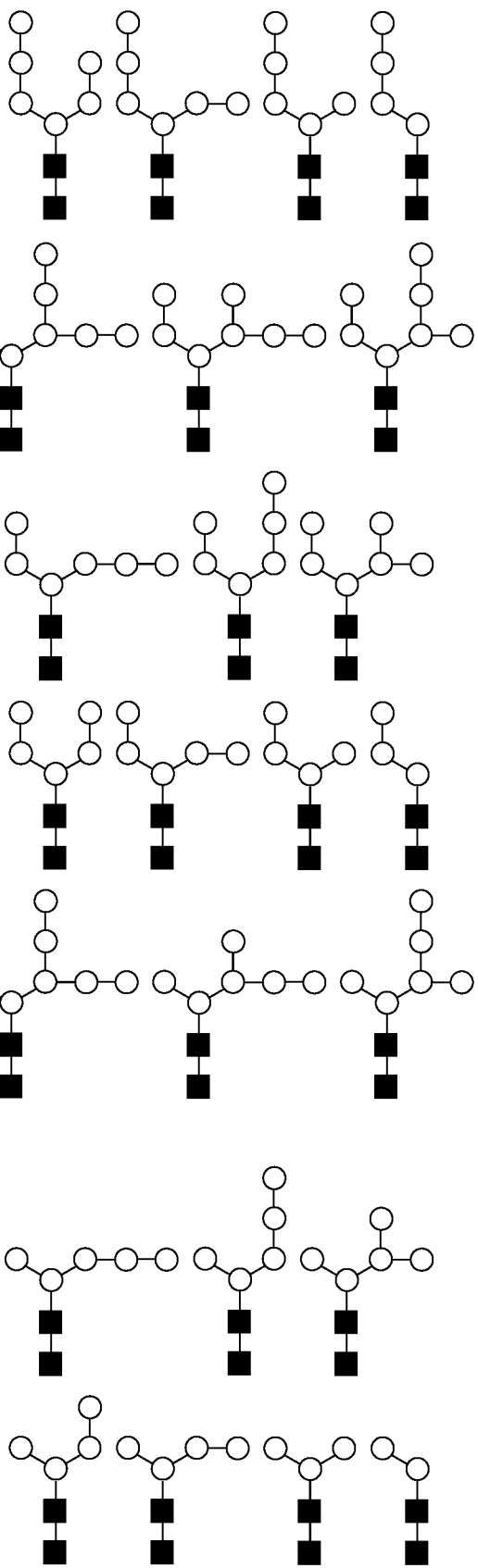

-continued

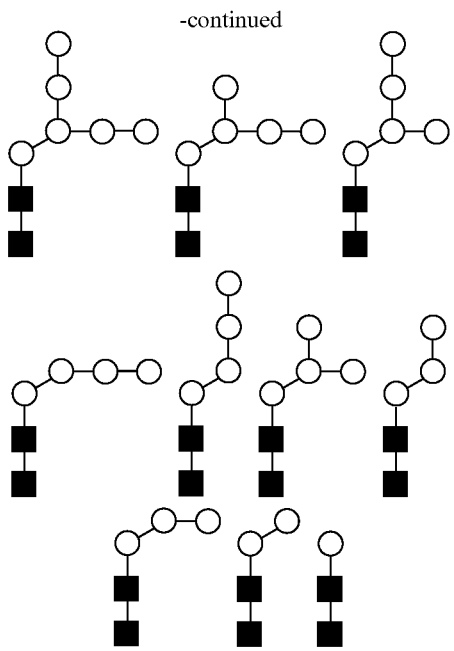

The symbols for the sugar residues are the same as those used in the schematic structures of high mannose type sugar chain (GlcMan9GlcNAc2)

Some methods using enzymes are known to date for preparing a sugar chain library. For example, Kajihara et al. (Chemistry—A European Journal Vol. 10: 971-985 (2004)) describes a method of preparing a sugar chain library using enzymes, which comprises converting an asparagine-bound sugar chain to various sugar chains by repeating limited degradation and sugar chain elongation reaction using a glycosidase and a glycosyl transferase in combination. However, these methods are problematic in that various naturally occurring sugar chains from high mannose type sugar chain like those described above cannot be produced specifically and systematically because, if the starting sugar chain compound has, for example, a plurality of non-reducing termini having the same kind of sugar residue (D-mannose) bound to the adjacent sugar residue in the same binding mode (α1-2 linkage), as in the above-described high mannose type sugar chain, the same reaction occurs undesirably in the plurality of non-reducing termini even in the presence of a glycosidase and a glycosyl transferase.

SUMMARY OF THE INVENTION

It is an object of the present invention to provide a new methodology that enables easier obtainment of various sugar chains (sugar chain library).

The present inventors conducted diligent investigations and found that various sugar chain compounds can be produced specifically and systematically by synthesizing sugar chain compounds protected with sugar residues at the termini thereof, which incorporate sugar residues that can be selectively removed with different glycosidases at the individual termini of the sugar chains, and then subjecting the thus-obtained synthetic sugar chain compounds to hydrolytic reactions with glycosidases. To date, none have proposed the concept of assuring the specificity of cleavage by glycosidases for specifically and systematically preparing naturally occurring sugar chain compounds by intentionally organically synthesizing sugar chain compounds having structures different from those of naturally occurring sugar chain compounds by introducing sugar residues to the non-reducing termini of sugar chain compounds having the same structures as those of naturally occurring sugar chain compounds. An enzymatic method can easily be performed and makes it possible to carry out multiple reactions at the same time. Therefore, provided that a starting sugar chain compound (a sugar chain compound protected at the terminus thereof by a sugar residue) is synthesized, the method developed by the present inventors enables its easy conversion to various sugar chain compounds (construction of a library). Furthermore, the method is also applicable to the production of non-natural-type sugar chains introducing a tag such as a fluorescent substance to a reducing terminus moiety, and enables the construction of a sugar chain probe library. The present inventors have succeeded in developing a method having these various advantages and completed the present invention.

Accordingly, the present invention provides the following:

[1] a protected sugar chain compound or a salt thereof, which is represented by the formula (I) below:

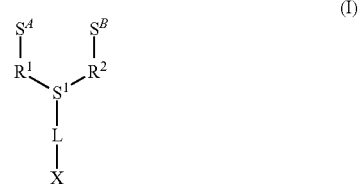

(I)

[wherein $R^1$ and $R^2$ are the same or different and each is a linear sugar chain with 1 to 10 sugar residues, or a branched sugar chain with 1 to 10 sugar residues, which has at a terminus thereof a protective sugar residue, $S^1$ is any sugar residue, $S^A$ and $S^B$ are the same or different sugar residues, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue $S^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ is substituted by an amino group in the absence of L, or represents an amino-protecting group or functional substance bound to the amino group which is substituted, the sugar residues $S^A$ and $S^B$ and the protective sugar residues in $R^1$ and $R^2$ are cleaved by different exoglycosidases, respectively].

[2] the sugar chain compound or salt thereof according to [1] above, which is characterized by one or more of the following features (a) to (d):

(a) $R^1$ and $R^2$ are linear sugar chains, and $S^A$ and $S^B$ are sugar residues different from each other;

(b) either $R^1$ or $R^2$ or both $R^1$ and $R^2$ are branched sugar chains having at a terminus thereof a protective sugar residue, and the protective sugar residue and the sugar residues $S^A$ and $S^B$ are different respectively;

(c) $R^1$ and $R^2$ are linear sugar chains, and the sugar residue in $R^1$, which is adjacent to $S^A$, and the sugar residue $S^A$ are different from each other, and the sugar residue in $R^2$ which is adjacent to $S^B$, and the sugar residue $S^B$ are different from each other;

(d) either $R^1$ or $R^2$ or both $R^1$ and $R^2$ are branched sugar chains having at a terminus thereof a protective sugar residue, and the protective sugar residue and the sugar residue adjacent thereto are different from each other, the sugar residue in $R^1$, which is adjacent to $S^A$, and the sugar residue $S^A$ are different from each other, and the sugar residue in $R^2$, which is adjacent to $S^B$, and the sugar residue $S^B$ are different from each other.

[3] the sugar chain compound or salt thereof according to [1] above, which is characterized by one or more of the following features (a) to (c):

(a) $R^1$ and $R^2$ are linear sugar chains, and each of $R^1$ and $R^2$ is composed of one kind of sugar residue;

(b) either $R^1$ or $R^2$ or both $R^1$ and $R^2$ are branched sugar chains having at a terminus thereof a protective sugar residue, and each of $R^1$ and $R^2$ is composed of one kind of sugar residue except the protective sugar residue;

(c) the sugar residue in $R^1$, which is adjacent to $S^A$, and the sugar residue in $R^2$, which is adjacent to $S^B$, are cleaved by the same exoglycosidase.

[4] the sugar chain compound or salt thereof according to [1] above, wherein the number of sugar residues in each of $R^1$ and $R^2$ is 3 to 8.

[5] the sugar chain compound or salt thereof according to [1] above, wherein $R^1$ and $R^2$ are the same or different and each is either the formulas $(v^3)$ or $(v^{14})$ below:

$$(v^3)$$
$$\begin{array}{c} | \\ S^4 \\ | \\ S^3 \\ | \\ S^2 \\ | \end{array}$$

$$(v^{14})$$
$$\begin{array}{c} | \\ S^4 \\ | \\ S^3 \\ | \\ S^{T1}-S^6-S^5-S^2 \\ | \end{array}$$

[wherein $S^2$ to $S^4$ in the formula $(v^3)$ and $S^2$ to $S^6$ in the formula $(v^{14})$ are any sugar residues, and $S^{T1}$ in the formula $(v^{14})$ is a protective sugar residue].

[6] the sugar chain compound or salt thereof according to [5] above, wherein the sugar residues $S^A$ and $S^B$ in the formula (I), the sugar residues $S^2$ to $S^4$ in the formula $(v^3)$, and the sugar residues $S^2$ to $S^6$ and $S^{T1}$ in the formula $(v^{14})$ are selected from the group consisting of D-glucose, D-mannose, D-galactose, D-xylose, N-acetyl-D-glucosamine, N-acetyl-D-galactosamine, L-fucose and sialic acid.

[7] the sugar chain compound or salt thereof according to [1] above, wherein the protected sugar chain compound is a compound represented by the formula (Ia) below:

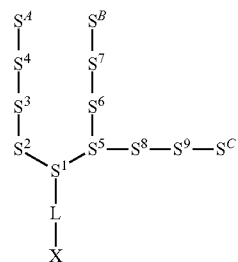

(Ia)

[wherein $S^1$ to $S^9$ are any sugar residues, $S^A$, $S^B$ and $S^C$ are the same or different sugar residues, L is a bond or a linear sugar chain with 1 to 10 sugar residues, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue $S^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ is substituted by an amino group in the absence of L, or represents an amino-protecting group or functional substance bound to the amino group which is substituted, the sugar residues $S^A$, $S^B$, and $S^C$ are cleaved by different exoglycosidases, respectively].

[8] the sugar chain compound or salt thereof according to [1] above, wherein the protected sugar chain compound is a compound represented by the formula (II) below:

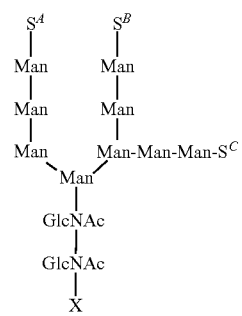

(II)

[wherein Man represents D-mannose, GlcNAc represents N-acetyl-D-glucosamine, $S^A$, $S^B$, and $S^C$ are the same or different sugar residues, X (i) is absent, or (ii) represents a hydroxyl-protecting group, amino acid residue or functional substance bound to any hydroxyl group in GlcNAc, or (iii) represents a structure wherein any hydroxyl group in GlcNAc is substituted by an amino group, or represents an amino-protecting group or functional substance bound to the amino group which is substituted, the sugar residues $S^A$, $S^B$, and $S^C$ are cleaved by different exoglycosidases, respectively].

[9] the sugar chain compound or salt thereof according to [8] above, wherein all binding modes between Man and Man, between GlcNAc and GlcNAc, and between Man and GlcNAc, are the same as the binding mode of natural high mannose type sugar chain compound.

[10] the sugar chain compound or salt thereof according to [8] above, wherein the sugar residues $S^A$, $S^B$ and $S^C$ are sugar residues different respectively.

[11] the sugar chain compound or salt thereof according to [8] above, wherein $S^A$ is D-glucose.

[12] a library comprising two or more kinds of protected sugar chain compounds or salts thereof, wherein the sugar chain compounds are represented by the formulas (I) and (I') below:

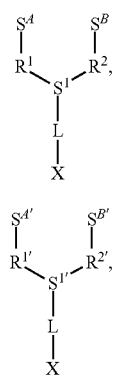

[wherein $R^1$, $R^2$, $R^{1'}$ and $R^{2'}$ are the same or different and each is a linear sugar chain with 1 to 10 sugar residues, or a branched sugar chain with 1 to 10 sugar residues, which has at a terminus thereof a protective sugar residue, $S^1$ and $S^{1'}$ are the same sugar residues, $S^A$, $S^B$, $S^{A'}$, and $S^{B'}$ are the same or different sugar residues, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue $S^1$ or $S^{1'}$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ or $S^{1'}$ is substituted by an amino group in the absence of L, or represents an amino-protecting group or functional substance bound to the amino group which is substituted, the sugar residues $S^A$ and $S^B$ and the protective sugar residues in $R^1$ and $R^2$ are cleaved by different exoglycosidases, respectively, the sugar residues $S^{A'}$ and $S^{B'}$ and the protective sugar residues in $R^{1'}$ and $R^{2'}$ are cleaved by different exoglycosidases, respectively].

[13] the library according to [12] above, wherein $R^1$ and $R^{1'}$ are the same sugar chains, $R^2$ and $R^{2'}$ are the same sugar chains, $S^A$ and $S^{A'}$ are sugar residues different from each other, and $S^B$ and $S^{B'}$ are sugar residues different from each other.

[14] the library according to [12] above, which is characterized by (a) or (b) below:

(a) $R^1$, $R^2$, $R^{1'}$ and $R^{2'}$ are linear sugar chains, and the sugar residues $S^A$, $S^{A'}$, $S^B$ and $S^{B'}$ are different respectively;

(b) at least one of $R^1$, $R^2$, $R^{1'}$ and $R^{2'}$ is a branched sugar chain having at a terminus thereof a protective sugar residue, and the protective sugar residue and the sugar residues $S^A$, $S^{A'}$, $S^B$ and $S^{B'}$ are different respectively.

[15] the library according to [13] above, which further comprises a protected sugar chain compound represented by the formula (I'') below:

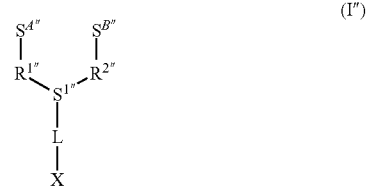

[wherein $R^{1''}$ and $R^{2''}$ are the same or different and each is a linear sugar chain with 1 to 10 sugar residues, or a branched sugar chain with 1 to 10 sugar residues, which has at a terminus thereof a protective sugar residue, $S^{1''}$ is the same sugar residue as $S^1$ and $S^{1'}$, $S^{A''}$ is a sugar residue different from $S^A$ and $S^{A'}$, and $S^{B''}$ is a sugar residue different from $S^B$ and $S^{B'}$, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue $S^{1''}$ in the absence of L, or (iii) represents a structure wherein any hydroxyl group in the L-constituting sugar residue on the reducing terminus side is substituted by an amino group in the presence of L, or a structure wherein any hydroxyl group in the sugar residue of $S^{1''}$ is substituted by an amino group in the absence of L, or represents an amino-protecting group or functional substance bound to the amino group which is substituted, the sugar residues $S^{A''}$ and $S^{B''}$ and the protective sugar residues in $R^{1''}$ and $R^{2''}$ are cleaved by different exoglycosidases, respectively].

[16] a method of producing a sugar chain compound, which comprises treating a protected sugar chain compound represented by the formula (I) above or a salt thereof with glycosidase to yield the sugar chain compound.

[17] a method of producing a sugar chain compound, which comprises treating a library comprising two or more kinds of protected sugar chain compounds represented by the formulas (I) and (I') above or salts thereof, with glycosidase to yield the sugar chain compound.

[18] a method of producing a sugar chain compound, which comprises synthesizing a protected sugar chain compound incorporating at least one sugar residue at the non-reducing terminus of a sugar chain having the same structure as a naturally occurring sugar chain, and treating the synthesized sugar chain compound with glycosidase to yield the sugar chain compound.

[19] a sugar chain compound or salt thereof, which is obtained by decomposing a protected high mannose type sugar chain compound represented by the formula (II) above with glycosidase, and (a) retaining either sugar residues $S^B$ or $S^C$ or both the sugar residues $S^B$ and $S^C$; or (b) retaining a sugar residue other than α-D-glucose as $S^A$.

[20] a sugar chain compound of any of the formulas (IIa1) to (IIa4), (IIa8), (IIb4) to (IIb5), and (IIb14) below or a salt thereof:

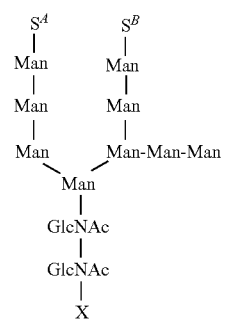
(IIa1)

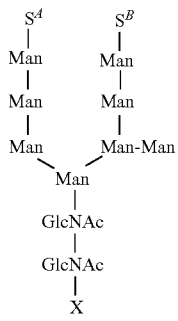
(IIa2)

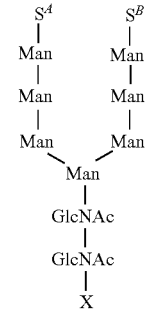
(IIa3)

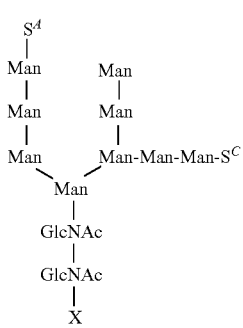
(IIa4)

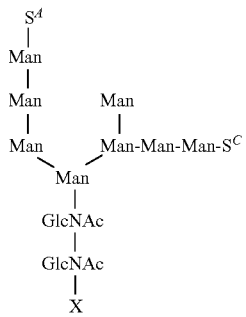
(IIa8)

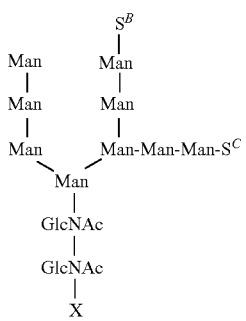
(IIb4)

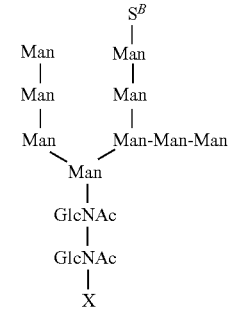
(IIb5)

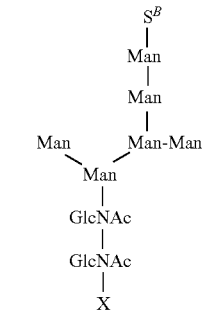
(IIb14)

[wherein Man represents D-mannose, GlcNAc represents N-acetyl-D-glucosamine,

X (i) is absent, or (ii) represents a hydroxyl-protecting group, amino acid residue or functional substance bound to any hydroxyl group in GlcNAc, or (iii) represents a structure wherein any hydroxyl group in GlcNAc is substituted by an amino group, or represents an amino-protecting group or functional substance bound to the amino group which is substituted, the sugar residues $S^A$, $S^B$, and $S^C$ are different respectively, and are selected from the group consisting of D-glucose, D-galactose, D-xylose, N-acetyl-D-glucosamine, N-acetyl-D-galactosamine, L-fucose, and sialic acid].

[21] a sugar chain compound or a salt thereof, which is represented by the formula (I$^P$) below:

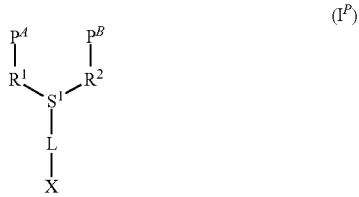

[wherein R$^1$ and R$^2$ are the same or different and each is a linear sugar chain with 1 to 10 sugar residues, or a branched sugar chain with 1 to 10 sugar residues, which has at a terminus thereof a protective sugar residue, S$^1$ is any sugar residue, P$^A$ and P$^B$ are hydroxy-protecting groups different from each other, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue S$^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue S$^1$ is substituted by an amino group in the absence of L, or represents an amino-protecting group or functional substance bound to the amino group which is substituted].

[22] a reagent or kit, which comprises the sugar chain compound or salt thereof according to [1] above, the library according to [12] above or a glycosidase decomposition product thereof or a salt thereof, or the sugar chain compound according to [20] above or a salt thereof.

[23] a kit, which comprises (a) and (b) below:

(a) the sugar chain compound or salt thereof according to [1] above, or the library according to [12] above;

(b) one or more glycosidases.

BEST MODE FOR EMBODIMENT OF THE INVENTION

Figure 1:
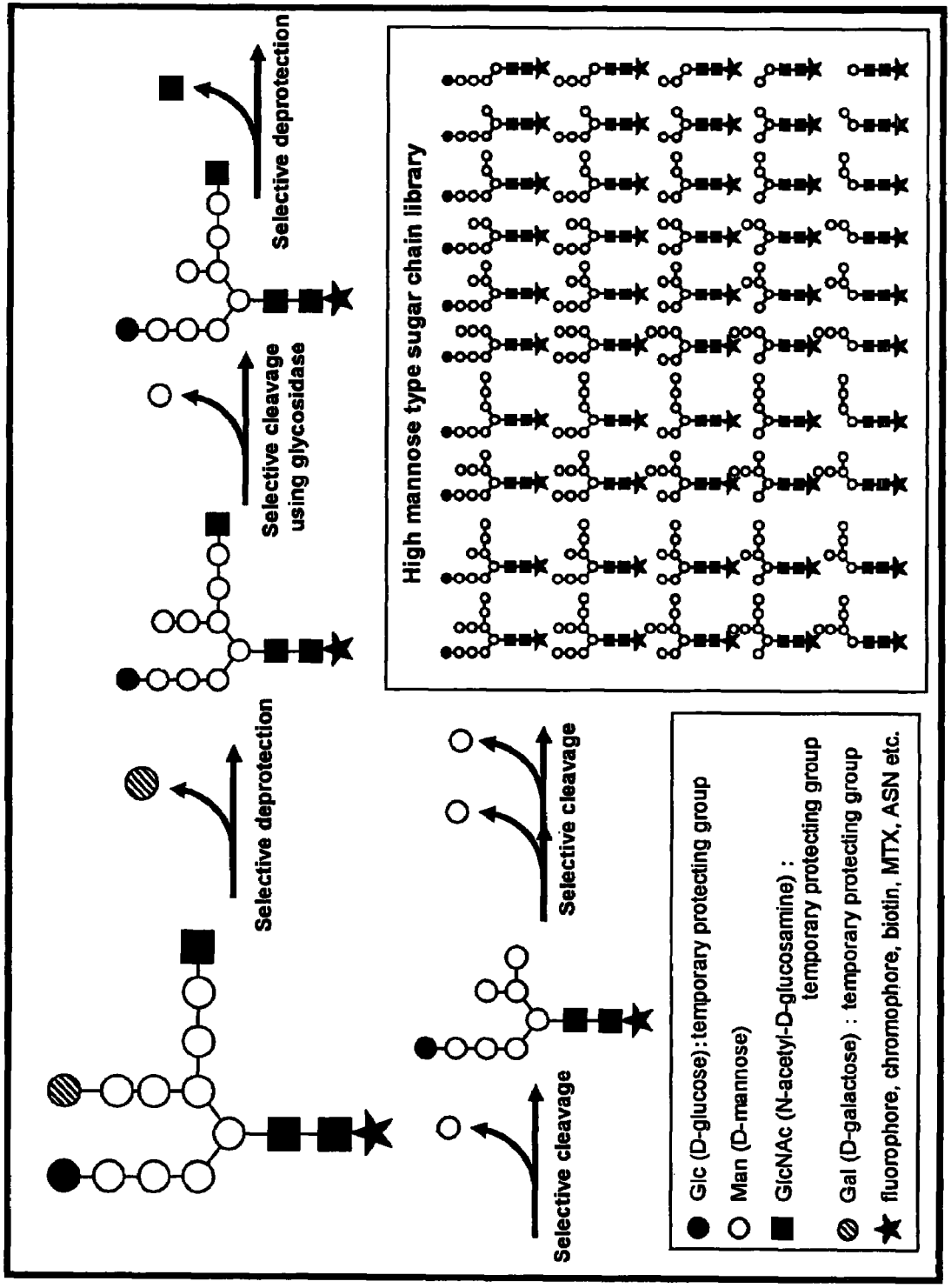
FIG. 1 shows an outline of the construction of various sugar chain compounds from a protected high mannose type sugar chain compound. The sugar residues at sugar chain termini are temporary protecting groups.

1. Protected Sugar Chain Compounds and Methods of Producing the Same

The present invention provides a protected sugar chain compound or a salt thereof.

As used herein, the term "protected" in "protected sugar chain compound" refers to the presence of sugar residues that can be selectively removed with different exoglycosidases at the non-reducing termini of the sugar chains. Therefore, a protected sugar chain compound in the present invention can be a sugar chain compound having sugar residues that can be selectively removed with different exoglycosidases at two or more non-reducing termini of the sugar chains. Examples of such protected sugar chain compounds include (a) a sugar chain compound having different kinds of sugar residues at two or more sugar chain termini thereof, (b) sugar chain compounds that have the same kind of sugar residue at two or more sugar chain termini thereof, but the binding modes between the sugar residue and the sugar residue adjacent thereto are different from each other, and (c) a sugar chain compound having a combination of (a) and (b) above.

The "sugar chain compound" in a "protected sugar chain compound" can be a compound having the same structure as that of a naturally occurring sugar chain (a compound consisting of a structure of the same sugar composition, sugar arrangement pattern and sugar-sugar binding mode, or a compound containing such a structure as a portion of the molecular structure thereof), or a non-naturally occurring newly designed sugar chain compound (a sugar chain compound that can therefore have any sugar composition, sugar arrangement pattern and sugar-sugar binding mode). Examples of the naturally occurring sugar chain include N-linked sugar chains that bind to asparagine residues found in proteins (peptides) (e.g., high mannose type sugar chains, complex type sugar chains, hybrid type sugar chains), O-linked sugar chains that bind to serine or threonine residues found in proteins (e.g., mucin type sugar chains CORE 1 to 8, dystroglycan sugar chains in animal), and Notch sugar chains.

A protected sugar chain compound in the present invention is hereinafter sometimes abbreviated "a protected compound of the present invention" as required. A sugar residue existing at a sugar chain terminus (non-reducing terminus) in a protected compound of the present invention is hereinafter sometimes abbreviated "terminal sugar residue" as required. For example, the terminal sugar residue can be $S^A$ and $S^B$ (and $S^C$ or $S^D$ if any), and a protective sugar residue (e.g., $S^{T1}$, $S^{T2}$) in a branched sugar chain (e.g., $R^1$, $R^2$) having at a terminus thereof the protective sugar residue, as described below.

Specifically, a protected compound of the present invention can be, for example, a compound represented by the formula (I) above.

In the formula (I) above, $R^1$ and $R^2$ are the same or different and each can be a linear sugar chain, or a branched sugar chain having at a terminus thereof a protective sugar residue. The "protective sugar residue" in "a branched sugar chain having at a terminus thereof a protective sugar residue" refers to a sugar residue that can be selectively removed with an exoglycosidase, located at a terminus of a branched chain (see, e.g., $S^{T1}$ and $S^{T2}$ in $(v^5)$ $(v^{13})$ $(v^{14})$, and $(v^{27})$ below). Therefore, "a branched sugar chain having at a terminus thereof a protective sugar residue" can be a sugar chain incorporating a sugar residue that can be selectively removed with an exoglycosidase different from the exoglycosidase capable of selectively removing $S^A$, $S^B$, and other protective sugar residues (in case where a plurality of branched structures are present) at a terminus of a branch chain thereof.

The number of sugar residues in the sugar chains $R^1$ and $R^2$ can be any one, for example, 1 to 20. The upper limit of the number of sugar residues can be preferably 15 or less, more preferably 10 or less, further more preferably 8 or less, most preferably 7, 6 or 5 or less. The lower limit of the number of sugar residues can be 1 or more, preferably 2 or more, more preferably 3, 4 or 5 or more.

"A branched sugar chain having at a terminus thereof a protective sugar residue" may be any sugar chain having 1 or more branched structures, and it is preferable, from the viewpoint of the ease of organic synthesis, that the number of branches be smaller, and the number can, for example, be 4 or less, preferably 3 or less, more preferably 2 or less, most preferably 1.

More specifically, $R^1$ and $R^2$ can have a sugar chain structure selected from the group consisting of $(v^1)$ to $(v^{43})$ below. Here, $S^2$ to $S^8$ are any sugar residues, and $S^{T1}$ or $S^{T2}$ can be a protective sugar residue. In some Examples below, $(v^3)$ and $(v^{14})$ were actually prepared as sugar chain structures for $R^1$ and $R^2$. Therefore, the combination of $R^1$ and $R^2$ is preferably, out of the sugar chain structures shown below, a combination of $(v^3)$ and $(v^{14})$, a combination of $(v^3)$ and $(v^3)$, or a combination of $(v^{14})$ and $(v^{14})$, but, from the viewpoint of preference to structural identity to a naturally occurring sugar chain (e.g., high mannose type sugar chain, complex type sugar chain, hybrid type sugar chain), a combination of $(v^3)$ and $(v^{14})$ and a combination of $(v^{14})$ and $(v^{14})$ are more preferable. From the viewpoint of preference to structural identity to a naturally occurring sugar chain, $(v^1)$ is also preferable for $R^1$ and $R^2$.

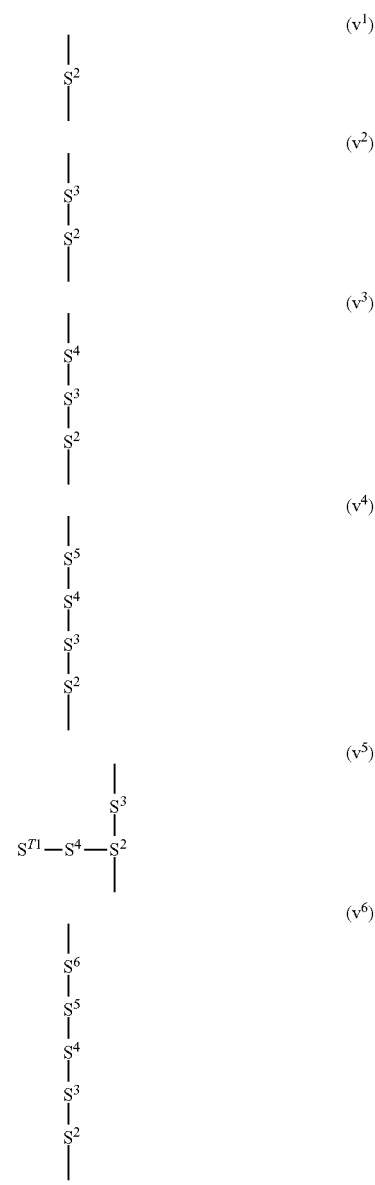

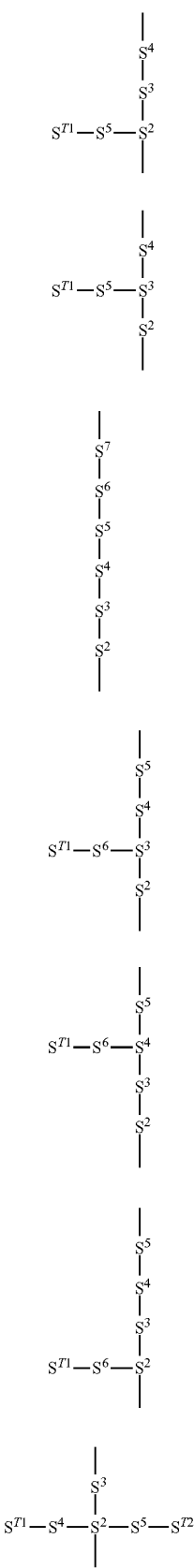
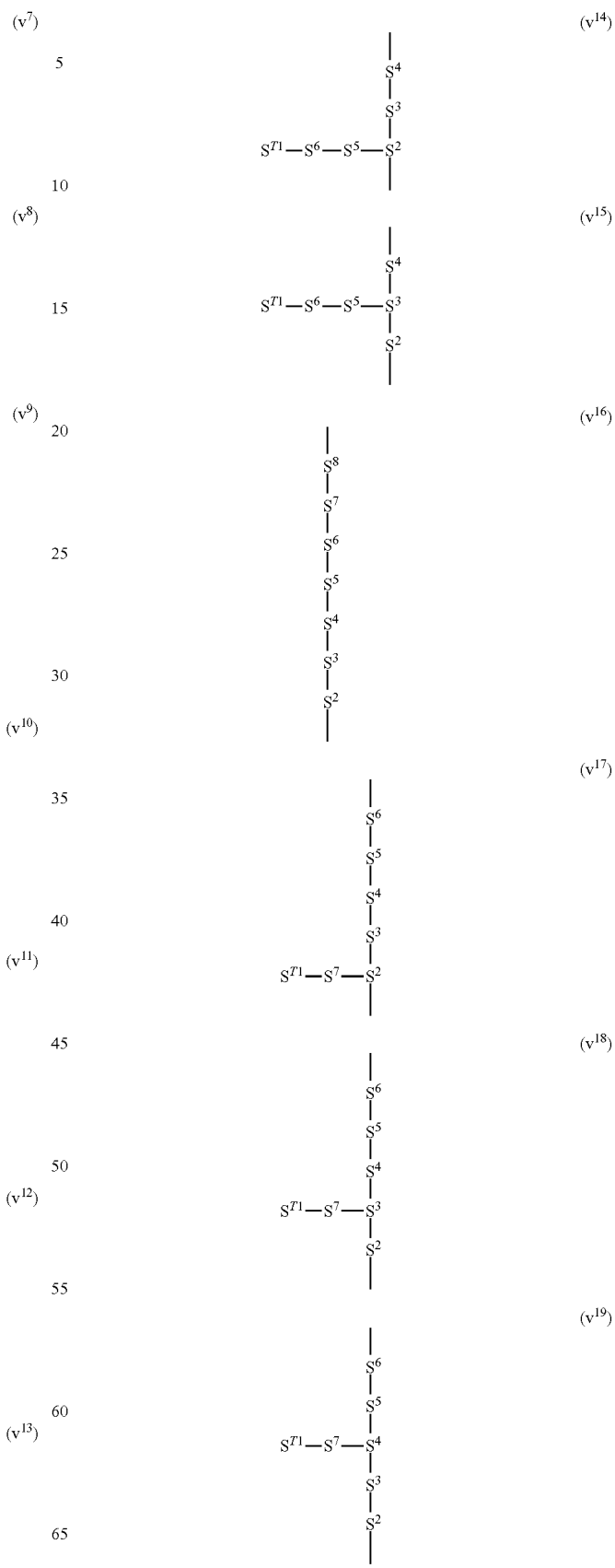

-continued
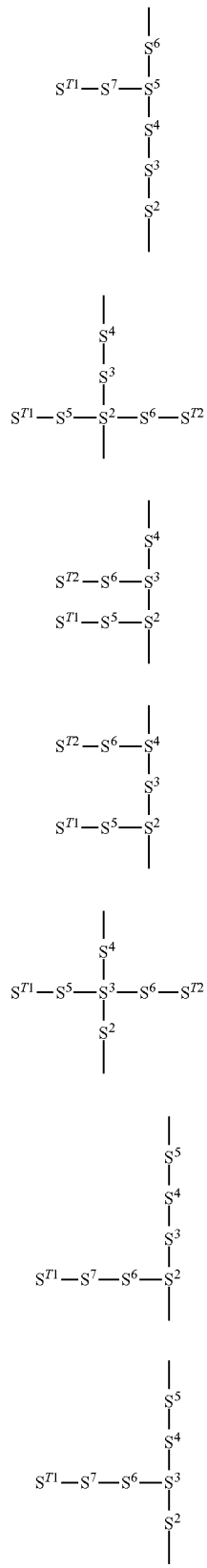
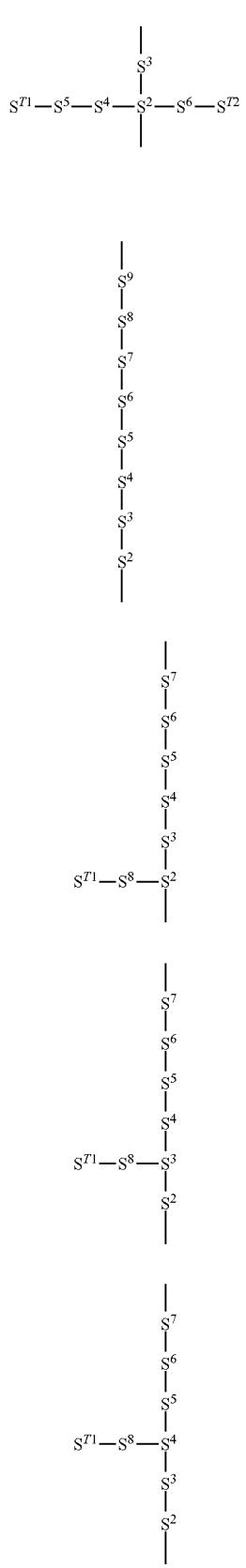

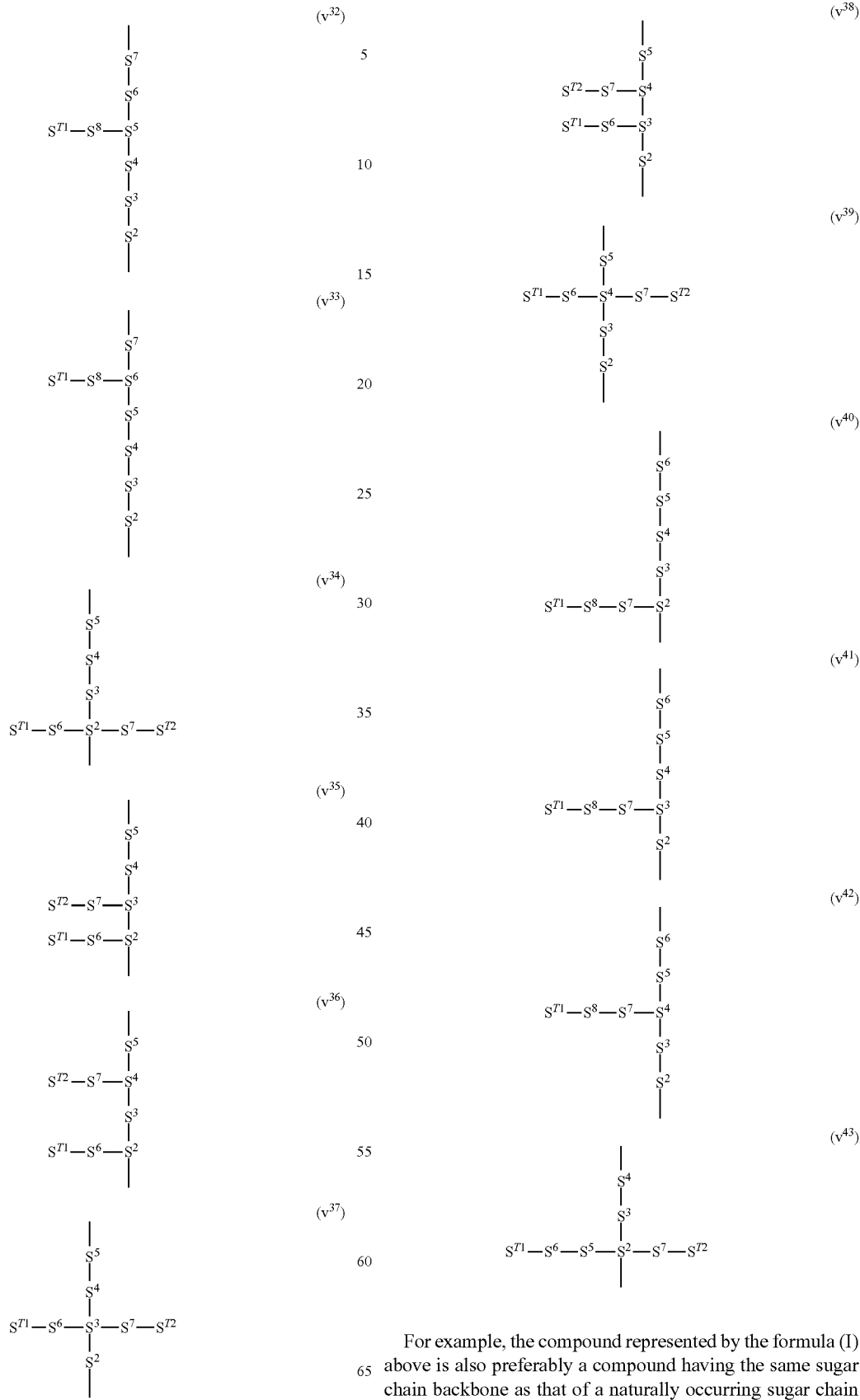
For example, the compound represented by the formula (I) above is also preferably a compound having the same sugar chain backbone as that of a naturally occurring sugar chain compound. Such a compound may be a sugar chain compound represented by the formula (Ia) above, a compound represented by the formula (Ib) below:

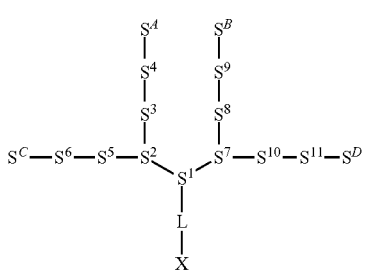

(Ib)

[wherein $S^1$ to $S^{11}$ are any sugar residues, $S^A$, $S^B$, $S^C$ and $S^D$ are the same or different sugar residues, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional-substance bound to any hydroxyl group in the sugar residue $S^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ is substituted by an amino group in the absence of L, or represents an amino-protecting group or functional substance bound to the amino group which is substituted, the sugar residues $S^A$, $S^B$, $S^C$, and $S^D$ are cleaved by different exoglycosidases, respectively], or a compound represented by the formula (Ic) below:

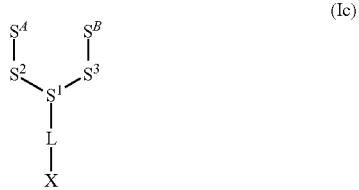

(Ic)

[wherein $S^1$ to $S^3$ are any sugar residues, $S^A$ and $S^B$ are the same or different sugar residues, L is a bond or a linear sugar chain with 1 to 5 sugar residues, X (i) is absent, or (ii) represents any hydroxyl group in the L-constituting sugar residue on the reducing terminus side in the presence of L, or a hydroxyl-protecting group, amino acid residue or functional-substance bound to any hydroxyl group in the sugar residue $S^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ is substituted by an amino group in the absence of L, or represents an amino-protecting group or functional substance bound to the amino group which is substituted, the sugar residues $S^A$ and $S^B$ are cleaved by different exoglycosidases, respectively].

Examples of the sugar residues that constitute the sugar chains $R^1$, $R^2$, and L, and the sugar residues $S^A$, $S^B$, $S^C$, $S^D$, $S^{T1}$, $S^{T2}$, and $S^1$ to $S^{11}$, in the formulas (I), (Ia), (Ib), (Ic), and $(v^1)$ to $(v^{43})$, include pentose, hexose, and heptose. The sugar residues can also be aldose or ketose. The sugar residues can also be of the D-configuration or the L-configuration. Of the above-described sugar residues, the sugar residues that constitute the sugar chains $R^1$ and $R^2$, and the sugar residues $S^A$, $S^B$, $S^C$, $S^D$, $S^{T1}$, $S^{T2}$, and $S^2$ to $S^{11}$ particularly the sugar residues $S^A$, $S^B$, $S^C$, $S^D$, $S^{T1}$, and $S^{T2}$, are preferably D-glucose, D-mannose, D-galactose, N-acetyl-D-glucosamine, N-acetyl-D-galactosamine, L-fucose, D-xylose, and sialic acid, which can be selectively cleaved by a wide variety of exoglycosidases that have been isolated to date.

With respect to the formulas (I), (Ia), (Ib), (Ic), and $(v^1)$ to $(v^{43})$ above, the sugar residues that constitute the sugar chains $R^1$ and $R^2$, and the sugar residues $S^A$, $S^B$, $S^C$, $S^D$, $S^{T1}$, $S^{T21}$ and $S^2$ to $S^{11}$ particularly the sugar residues $S^A$, $S^B$, $S^C$, $S^D$, $S^{T1}$, and $S^{T2}$, can also be characterized from the viewpoint of exoglycosidases that cleave these. Examples of exoglycosidases that cleave these sugar residues include, but are not limited to, glucosidase, mannosidase, galactosidase, xylanase, N-acetylglucosaminidase (GlcNAcase), and N-acetylgalactosaminidase. The sugar residues that constitute the sugar chains $R^1$ and $R^2$, and the sugar residues $S^2$ to $S^{11}$ can also be characterized from the viewpoint of endoglycosidases that cleave these. Examples of endoglycosidases that cleave these sugar residues include, but are not limited to, endomannosidase and endo-N-acetylglucosaminidase. For information on exo- and endoglycosidases, see, for example, Ernst et al., "Carbohydrates in Chemistry and Biology", Part II Biology of Saccharides, Vol. 3, Biosynthesis and Degradation of Glycoconjugates, WILEY-VCH.

In the formulas (I), (Ia), (Ib), (Ic), and $(v^1)$ to $(v^{43})$ above, the sugar-sugar binding modes for the sugar residues that constitute the sugar chains $R^1$, $R^2$, and L, and the sugar residues $S^A$, $S^B$, $S^C$, $S^D$, $S^{T1}$, $S^{T2}$, and $S^1$ to $S^{11}$, are any binding modes, whether α linkage or β linkage. Of these sugar residues, the sugar residues that constitute the sugar chains $R^1$ and $R^2$, and the sugar residues $S^A$, $S^B$, $S^C$, $S^D$, $S^{T1}$, $S^{T2}$, and $S^2$ to $S^{11}$, particularly the sugar residues $S^A$, $S^B$, $S^C$, $S^D$, $S^{T1}$, and $S^{T2}$, may have any sugar-sugar binding mode, as long as the mode allows them to be selectively cleaved by a given glycosidase chosen according to the kind of sugar residue. More specifically, such binding modes include α1-2 linkage, α1-3 linkage, α1-4 linkage, α1-5 linkage, α1-6 linkage, β1-2 linkage, β1-3 linkage, β1-4 linkage, β1-5 linkage, and β1-6 linkage. Also, because ketoses such as sialic acid utilize the 2-position hydroxy group for their linkage, useful binding modes for these ketoses include α2-2 linkage, α2-3 linkage, α2-4 linkage, α2-5 linkage, and α2-6 linkage. A protected compound of the present invention can, for example, have the same binding mode as that of a naturally occurring sugar chain.

In the formulas (I), (Ia), (Ib), and (Ic) above, the sugar residue that constitutes the sugar chain L is not subject to limitation, but from the viewpoint of identity to a naturally occurring sugar chain, N-acetyl-D-glucosamine is preferable. The number of sugar residues constituting the sugar chain L can be any one, for example, 0 (i.e., a bond) to 10, preferably 0 to 5, more preferably 0 to 3, but from the viewpoint of identity to a naturally occurring sugar chain, 0 or 2 is preferable. From the same viewpoint, the binding mode for the sugar residues that constitute the sugar chain L is preferably β1-4 linkage.

In the formulas (I), (Ia), (Ib), and (Ic) above, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue $S^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue $S^1$ is substituted by an amino group in the absence of L, or represents an amino-protecting group or functional substance bound to the amino group which is substituted. The number of hydroxyl groups to which a hydroxyl-protecting group binds in (ii) above, and the number of hydroxyl groups substituted by amino groups in (iii) above can be, but are not limited to, for example, 1 to 3, preferably 1 or 2, with greater preference given to 1. The positions of the hydroxyl groups to which a hydroxyl-protecting group, amino acid residue or functional substance binds in (ii), and the hydroxyl groups substituted by an amino group (may be bound with an amino-protecting group or functional substance) in (iii) above can be any ones; for example, regarding the sugar residues in 6-membered rings, hydroxyl groups at the 1-, 2-, 3-, 4- and 6-positions can be mentioned; regarding the sugar residues in 5-membered rings, hydroxyl groups at the 1-, 2-, 3- and 5-positions can be mentioned; for example, from the viewpoint of utilization of hydroxyl groups at the same positions as those in naturally occurring sugar chains, the hydroxyl group at the 1-position is useful in the formulas (Ia), (Ib), and (Ic).

The hydroxy-protecting group and amino-protecting group in X can be the same as those described below. The choice of amino acid residue is not subject to limitation, sugar chain-binding amino acid residues found in naturally occurring substances are preferable; examples of such amino acid residues include asparagine, to which an N-linked sugar chain binds, and serine/threonine, to which an O-linked sugar chain binds. Examples of the functional substance include labeling marker substances, affinity substances (e.g., biotin, streptavidin, benzophenone, methotrexate), peptides (e.g., secreted peptides, basic peptides, acidic peptides), and these substances coupled with a linker (e.g., —NH—, —O—, $C_{1-10}$ (e.g., $C_{1-6}$ alkyls such as methyl, ethyl, propyl, butyl, and pentyl) and a combination thereof) and the like. Examples of the labeling marker substance include fluorescent substances (e.g., fluorescein, fluorescein isothiocyanate, rhodamine, FITC, FAM), luminescent substances (e.g., para-nitrophenyl group), substances containing radioisotopes (e.g., $^3H$, $^{14}C$, $^{32}P$, $^{35}S$, $^{123}I$), reactive substituents (e.g., haloamido groups, thiol group), photoaffinity substituents (e.g., benzophenone derivatives, diazirine derivatives, azide group).

In one embodiment of the present invention, a protected compound of the present invention, from the viewpoint of the selectivity of cleavage by exoglycosidases, can have different kinds of terminal sugar residues, or can have different binding modes for terminal sugar residues even if they are of the same kind. In this context, selectively removal of sugar residues is basically possible, provided that they have different binding modes. From the viewpoint of the ease of choice of useful enzymes, however, it is preferable that the terminal sugar residues be of different kinds. Therefore, provided that $R^1$ and $R^2$ in the formula (I) above are linear sugar chains, $S^A$ and $S^B$ may be mutually different kinds of sugar residues. Provided that either $R^1$ or $R^2$ or both of $R^1$ or $R^2$ are branched sugar chains having at a terminus thereof one or more protective sugar residues, at least one, preferably at least two, more preferably all, of the protective sugar residues and $S^A$ and $S^B$ may be mutually different kinds of sugar residues. In the formula (Ia) above, $S^A$, $S^B$, and $S^C$ may be different kinds of sugar residues. In the formula (Ib) above, $S^A$, $S^B$, $S^C$, and $S^D$ may be different kinds of sugar residues. In the formula (Ic) above, $S^A$ and $S^B$ may be different kinds of sugar residues.

In another embodiment of the present invention, a protected compound of the present invention, from the viewpoint of terminal protection by conferring different glycosidase cleavage profiles to the terminus of each sugar chain, the kind of the terminal sugar residue and the kind of the sugar residue adjacent thereto can be different. Therefore, provided that $R^1$ and $R^2$ in the formula (I) above are linear sugar chains, the sugar residue in $R^1$, which is adjacent to $S^A$, and the sugar residue $S^A$, and/or the sugar residue in $R^2$, which is adjacent to $S^B$, and the sugar residue $S^B$ can be mutually different. Provided that either $R^1$ or $R^2$ or both of $R^1$ or $R^2$ are branched sugar chains having a protective sugar residue at a terminus thereof, the kinds of sugar residues can be different in at least one, preferably at least two, more preferably all, cases of between the protective sugar residue and the sugar residue adjacent thereto, between the sugar residue in $R^1$, which is adjacent to $S^A$, and the sugar residue $S^A$, and between the sugar residue in $R^2$, which is adjacent to $S^B$, and the sugar residue $S^B$. In the formula (Ia) above, the kinds of sugar residues can be different in at least one, preferably at least two, more preferably all, cases of between $S^4$ and $S^A$, between $S^7$ and $S^B$, and between $S^9$ and $S^C$. In the formula (Ib) above, the kinds of sugar residues can be different at least one, preferably at least two, more preferably all, cases of between $S^4$ and $S^A$, between $S^9$ and $S^B$, between $S^6$ and $S^C$, and between $S^{11}$ and $S^D$. In the formula (Ic) above, the kinds of residues can be different between $S^2$ and $S^A$ and/or between $S^3$ and $S^B$.

In another embodiment of the present invention, a protected compound of the present invention can be one wherein two or more sugar chains contained therein (but excluding terminal sugar residues) have similar sugar compositions and/or sugar-sugar binding modes. Therefore, in the formula (I) above, a structure wherein the kinds and/or binding modes of the sugar residues that constitute $R^1$ and $R^2$ are fully consistent (completely identical structure) may be present, or a structure wherein the kinds and/or binding modes are partially consistent (partially identical structure) may be present. In the formula (Ia) above, at least two, for example, all, of a) a sugar chain composed of $S^2$ to $S^4$, b) a sugar chain composed of $S^5$ to $S^7$, and c) a sugar chain composed of $S^5$, $S^8$ and $S^9$, may have completely or partially the same structure. In the formula (Ib) above, at least two, for example, three or all, of a) a sugar chain composed of $S^2$ to $S^4$, b) a sugar chain composed of $S^2$, $S^5$, and $S^6$, c) a sugar chain composed of $S^7$ to $S^9$, and d) a sugar chain composed of $S^7$, $S^{10}$, and $S^{11}$, may have completely or partially the same structure. In the formula (Ic) above, $S^2$ and $S^3$ may also have the same sugar residue and/or binding mode. If the sugar chain compound to be treated with exoglycosidases (unprotected sugar chain compound) has sugar chains of high similarity in terms of sugar residue composition and/or binding mode, it is difficult to specifically and systematically produce various sugar chain compounds by glycosidase decomposition. On the other hand, provided that the sugar chain compound to be treated is protected with sugar residues that can be selectively removed by different exoglycosidases, it is easily possible to specifically and systematically produce various sugar chain compounds by making use of exoglycosidases as appropriate. Therefore, the methodology developed by the present inventors can exhibit the advantages thereof particularly when applied to sugar chain compounds having sugar chains of high similarity in terms of sugar residue composition and/or binding mode.

In another embodiment of the present invention, a protected compound of the present invention can be one having sugar residues that are cleaved by the same exoglycosidase in two or more sugar chains contained therein (but excluding terminal sugar residues). For example, such a sugar residue can be one adjacent to a terminal sugar residue. Therefore, in the formula (I) above, the sugar residue in $R^1$, which is adjacent to $S^A$, the sugar residue in $R^2$, which is adjacent to $S^B$ (and provided that $R^1$ or $R^2$ or both are branched sugar chains having at a terminus thereof a protective sugar residue, the sugar residue adjacent to the protective sugar residue, as required) can be cleaved by the same exoglycosidase. In the formula (Ia) above, at least two, for example, all, of the sugar residues $S^4$, $S^7$, and $S^9$ can be cleaved by the same exoglycosidase. In the formula (Ib) above, at least two, for example, at least three or all, of the sugar residues $S^4$, $S^6$, $S^9$, and $S^{11}$ can be cleaved by the same exoglycosidase. In the formula (Ic) above, the sugar residues $S^2$ and $S^3$ can be cleaved by the same exoglycosidase. The methodology developed by the present inventors can also exhibit the advantages thereof when applied to such sugar chain compounds, for the same reasons as those described above.

In another embodiment of the present invention, a protected compound of the present invention can have two or more sugar chains composed of a small number of shared sugar residues. Therefore, provided that $R^1$ and $R^2$ in the formula (I) above are linear sugar chains, each of $R^1$ and $R^2$ can, for example, be a sugar chain composed of three kinds or less, preferably two kinds or less, more preferably one kind, of shared sugar residue. Provided that $R^1$ or $R^2$ or both are branched sugar chains having at a terminus thereof one or more protective sugar residues, each of $R^1$ and $R^2$ can, for example, be a sugar chain composed of three kinds or less, preferably two kinds or less, more preferably one kind, of shared sugar residue, except the protective sugar residue. In the formula (Ia) above, at least two, for example, all, of a) a sugar chain composed of $S^2$ to $S^4$, b) a sugar chain composed of $S^5$ to $S^7$, and c) a sugar chain composed of $S^5$, $S^8$, and $S^9$, can be sugar chains composed of two kinds or less, for example, one kind, of shared sugar residue. In the formula (Ib) above, at least two, for example, three or all, of a) a sugar chain composed of $S^2$ to $S^4$, b) a sugar chain composed of $S^2$, $S^5$, and $S^6$, c) a sugar chain composed of $S^7$ to $S^9$, and d) a sugar chain composed of $S^7$, $S^{10}$, and $S^{11}$, can be sugar chains composed of two kinds or less, for example, one kind, of shared sugar residue. In the formula (Ic) above, $S^2$ and $S^3$ can also be sugar chains composed of shared sugar residues. The methodology developed by the present inventors can also exhibit the advantages thereof when applied to such sugar chain compounds, for the same reasons as those described above.

More specifically, a compound represented by the formula (Ia) above can be a high mannose type sugar chain represented by the formula (II) above, or a compound wherein a hybrid type sugar chain having partial structures of a high mannose type sugar chain and a complex type sugar chain is protected by a sugar residue. Provided that a compound represented by the formula (Ia) above is a high mannose type sugar chain compound represented by the formula (II) above, all binding modes between Man and Man, between GlcNAc and GlcNAc, and between Man and GlcNAc, can be the same binding modes as those of natural high mannose type sugar chain compounds (see, e.g., the Background Art section). The sugar residues $S^A$, $S^B$, and $S^C$ can be mutually different sugar residues. Preferably, $S^A$ can be D-glucose. $S^B$ and $S^C$ are preferably any sugar residues other than D-mannose. More preferably, $S^B$ can be D-galactose, and $S^C$ can be N-acetyl-D-glucosamine.

Figure 16:
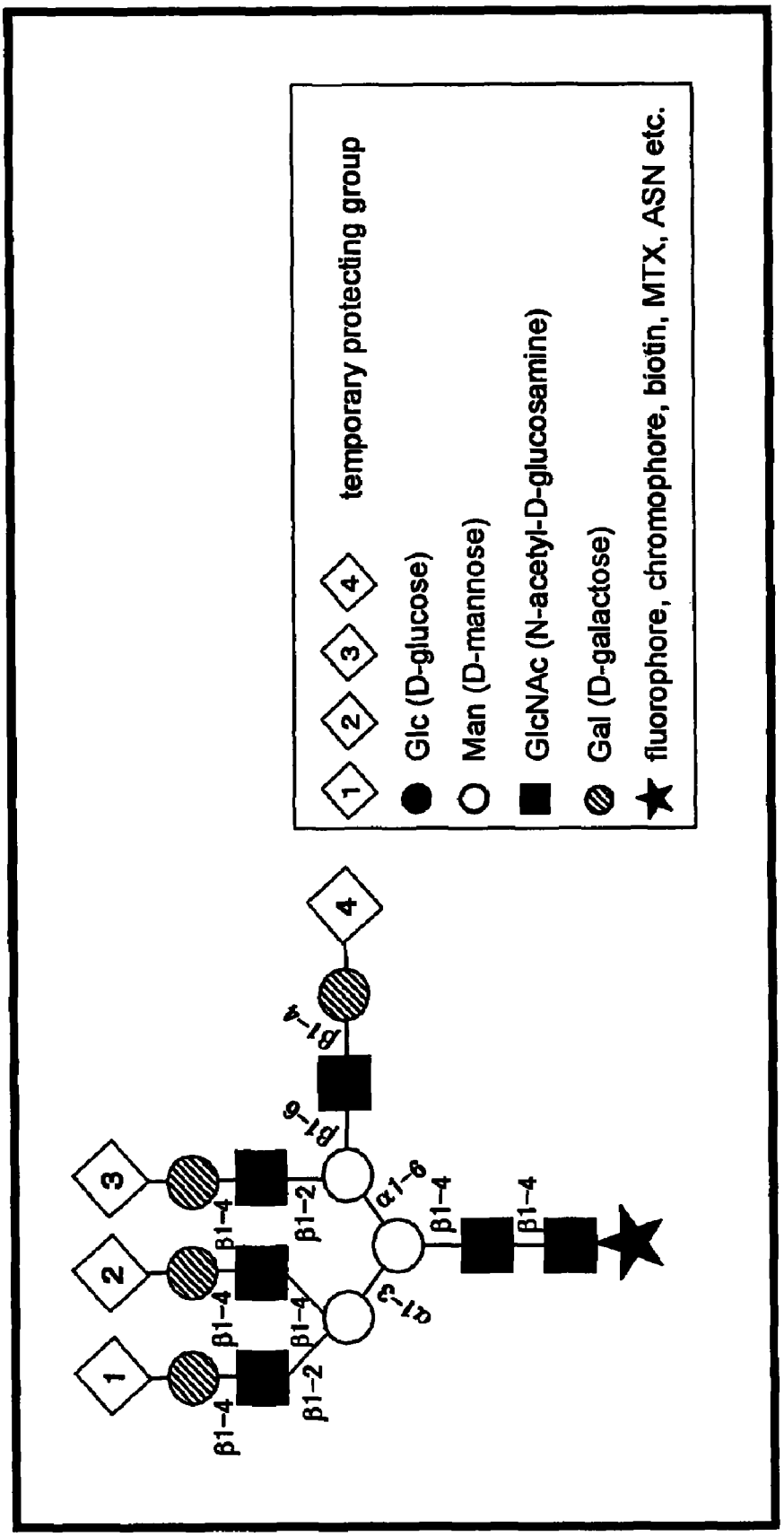
FIG. 16 shows the binding mode between sugar residues in a protected complex type sugar chain compound.

A compound represented by the formula (Ib) above can be a compound wherein a complex type sugar chain is protected by a sugar residue. Therefore, the sugar composition, sugar arrangement pattern and binding mode in the complex type sugar chain can be the same as those shown in FIG. 16. The sugar residues $S^A$, $S^B$, $S^C$, and $S^D$ can be mutually different sugar residues. Preferably, $S^A$, $S^B$, $S^C$, and $S^D$ can be sugar residues other than α-D-galactose (or D-galactose).

Figure 18:
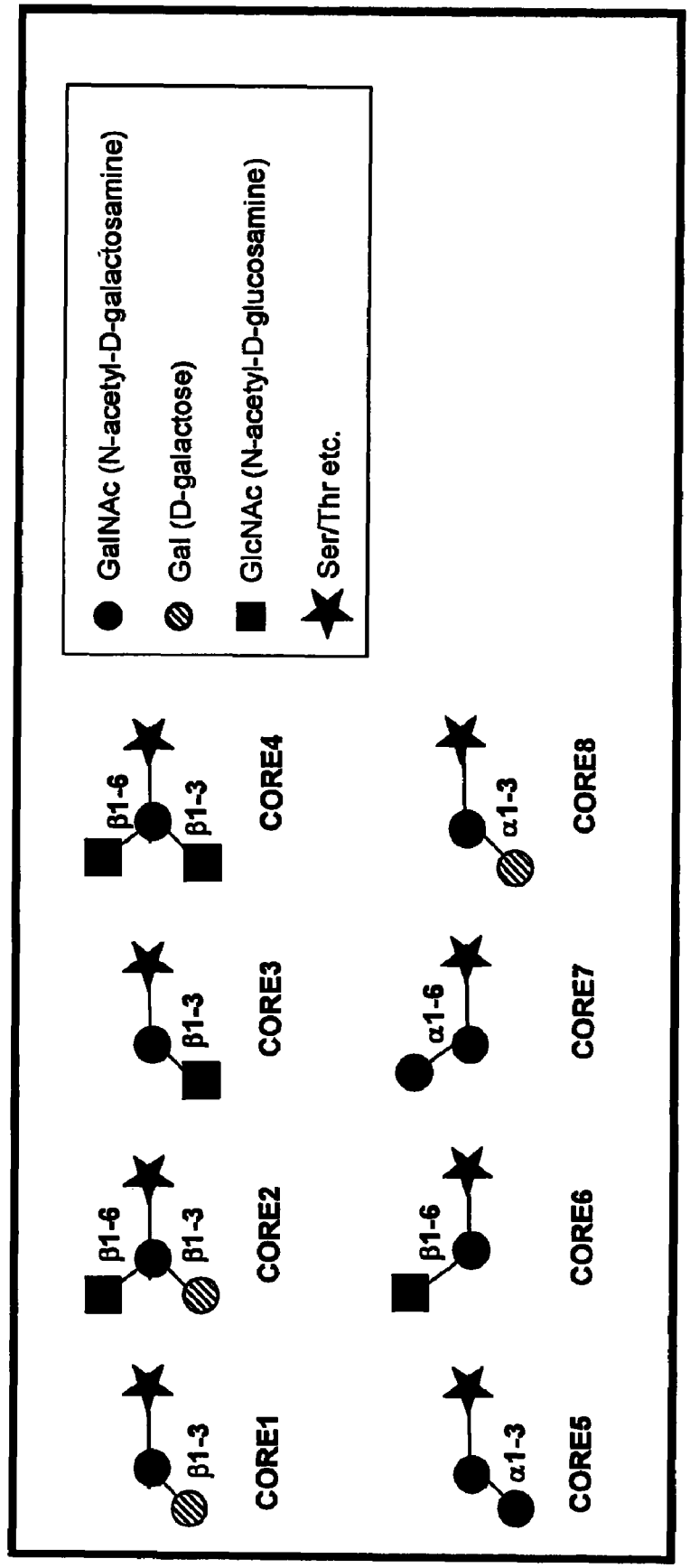
FIG. 18 shows the binding modes between sugar residues in natural O-linked sugar chains CORE 1 to 8.

A compound represented by the formula (Ic) above can be a compound wherein an O-linked sugar chain is protected by a sugar residue. Therefore, the sugar composition, sugar arrangement pattern and binding mode in the O-linked sugar chain can be the same as those of any of CORE 1 to 8 shown in FIG. 18. The sugar residues $S^A$ and $S^B$ can be mutually different sugar residues.

Examples of salts of the sugar chain compound of the present invention include, but are not limited to, salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine), or salts with acidic amino acids (e.g., aspartic acid, glutamic acid) and the like.

A protected compound of the present invention can easily be prepared by combining methods of sugar chain synthesis known per se as appropriate. For example, a protected compound of the present invention represented by the formula (I) can be produced by (a) reacting an $S^A$- and/or $S^B$-containing sugar block compound and a sugar block compound complementary thereto or a monosaccharide complementary thereto, or by (b) reacting $S^A$ and/or $S^B$ and a sugar block compound complementary thereto. The present invention also provides such a method of production. "A sugar block compound" refers to a compound having two or more sugar residues. The term "complementary" in "a complementary sugar block compound" or "complementary monosaccharide" means that a lacked partial structure is supplemented in the production of a final product (e.g., a sugar chain compound represented by the formula (I) above). For example, a sugar block compound complementary to an $S^A$-containing sugar block compound can be a sugar chain compound having a partial sugar chain structure that is not present in the $S^A$-containing sugar block compound, of the sugar chain structure that is present in the desired final product.

The production method of the present invention can also be a method of producing a compound represented by the formula (Ia), (Ib) or (Ic) above. Such a compound can be produced by (a) reacting a sugar chain block compound comprising at least one unit of $S^n$ (n represents either A or B, and, if any, C or D) and a sugar block compound complementary thereto or a monosaccharide complementary thereto, or by (b) reacting $S^n$ and a sugar block compound complementary thereto.

Production of a protected compound of the present invention may be performed by synthesizing a sugar chain compound (synthesis intermediate) wherein the sugar chain termini thereof are protected by hydroxy-protecting groups, and then removing the hydroxy-protecting groups, and adding sugar residues. Such a synthesis intermediate is particularly useful in preparing a library comprising a plurality of kinds of protected compounds of the present invention described below. The present invention also provides such a synthesis intermediate. For the sake of convenience in explaining the production method, a protected compound and synthesis intermediate of the present invention are hereinafter comprehensively represented by the formula (I$^P$) below.

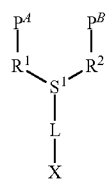
(I$^P$)

[wherein R$^1$ and R$^2$ are the same or different and each is a linear sugar chain or a branched sugar chain having at a terminus thereof a protective sugar residue, S$^1$ is any sugar residue, P$^A$ and P$^B$ are given protecting groups (e.g., sugar residues that can be selectively removed by exoglycosidases (e.g., S$^A$, S$^B$), hydroxy-protecting groups), L is a bond or a linear sugar chain, X (i) is absent, or (ii) represents any hydroxyl group in the L-constituting sugar residue on the reducing terminus side in the presence of L, or a hydroxyl-protecting group, amino acid residue or functional substance bound to any hydroxyl group in the sugar residue S$^1$ in the absence of L, or (iii) represents a structure wherein any hydroxyl group in the L-constituting sugar residue on the reducing terminus side is substituted by an amino group in the presence of L, or a structure wherein any hydroxyl group in the sugar residue S$^1$ is substituted by an amino group in the absence of L, or represents an amino-protecting group or functional substance bound to the amino group which is substituted]

(R$^1$, R$^2$, S$^1$, S$^A$, S$^B$, L, and X can be the same as those described above)

For example, a compound represented by the formula (I$^P$) above is also preferably a compound having the same sugar chain backbone as that of a naturally occurring sugar chain compound. Such compounds include sugar chain compounds represented by the formulas (Ia$^P$), (Ib$^P$) and (Ic$^P$) below:

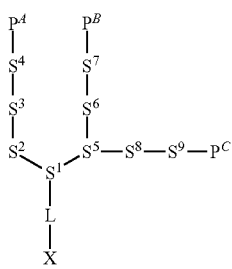
(Ia$^P$)

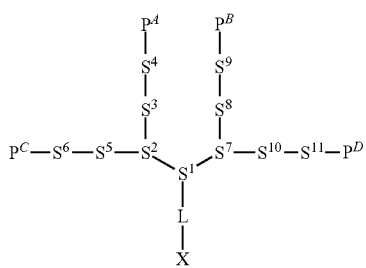
(Ib$^P$)

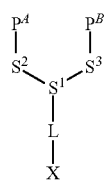
(Ic$^P$)

In the formulas (Ia$^P$), (Ib$^P$), and (Ic$^P$) above, P$^n$ can be an S$^n$ or a hydroxy-protecting group (n represents either A or B, and, if any, C or D). The symbols have the same definitions as those for the formulas (Ia), (Ib), and (Ic) above.

In a particular embodiment of the present invention, a compound represented by the formula (Ia$^P$) above can be a compound represented by the formula (II$^P$) above.

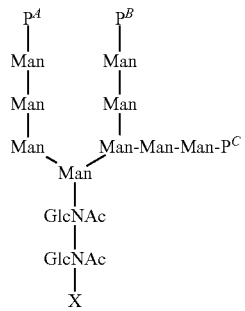
(II$^P$)

In the formula (II$^P$) above, the symbols have the same definitions as those for the formula (Ia) above. In the formula (II$^P$) above, it is also preferable that P$^A$ be D-glucose, and P$^B$ and P$^C$ be hydroxy-protecting groups.

A sugar block compound used in the present invention can be a compound having a reactive substituent at a given position to construct the sugar chain structure of the final product, wherein the hydroxy group the reaction to which must be avoided is protected by a hydroxy-protecting group, and the amino group, if any, is protected by an amino-protecting group.

A hydroxy-protecting group refers to a substituent that protects the hydroxy group during the reaction, for example, $C_{1-6}$ alkyl groups optionally having a substituent (e.g., methyl, ethyl, propyl, isopropyl, butyl, tert-butyl), phenyl, $C_{7-11}$ arylalkyl groups (e.g., benzyl, p-methoxybenzyl group), formyl, $C_{1-6}$ acyl groups (e.g., acetyl, propionyl, pivaloyl group), phenyloxycarbonyl group, $C_{7-11}$ aralkyloxy-carbonyl groups (e.g., benzyloxycarbonyl), tetrahydropyranyl, tetrahydrofuranyl, trityl group, silyl, t-butyldimethylsilyl group, triethylsilyl group, t-butyldiphenylsilyl group, methanesulfonyl group and the like are used. Substituents useful for these groups include halogen atoms (e.g., fluorine, chlorine, bromine, iodine), $C_{1-6}$ alkyl groups (e.g., methyl, ethyl, tert-butyl), $C_{7-11}$ aralkyl groups (e.g., benzyl), $C_{6-10}$ aryl groups (e.g., phenyl, naphthyl), nitro groups and the like.

An amino-protecting group refers to a substituent that protects the amino group during the reaction, for example, amide-containing protecting groups such as acetamide and trichloroacetamide, imide-containing protecting groups such as phthaloyl, $C_{1-6}$ alkyl-carbonyls (e.g., acetyl, propionyl), carbamate-containing protecting groups such as allyl carbamates and $C_{7-20}$ aralkyl carbamates (e.g., benzyl carbamate), trityl and the like are used. Useful substituents for these groups include halogen atoms (e.g., fluorine, chlorine, bromine, iodine), $C_{1-6}$ alkyl-carbonyls (e.g., acetyl, propionyl, valeryl), nitro groups and the like. An amino group protecting group particularly preferably used in the present invention is the phthaloyl group.

Described below is an outline of the synthesis of a protected compound and intermediate of the present invention with reference to a compound represented by the formula (Ia). A compound represented by the formula (Ia) can easily be produced according to the following schemes and explanations thereof, statements in Examples below and a method known per se in the art. Of course, those skilled in the art can easily produce other sugar chain compounds as well. The present invention also provides compounds appearing in the schemes shown below, compounds described in Examples, and salts thereof.

Reaction Scheme 1

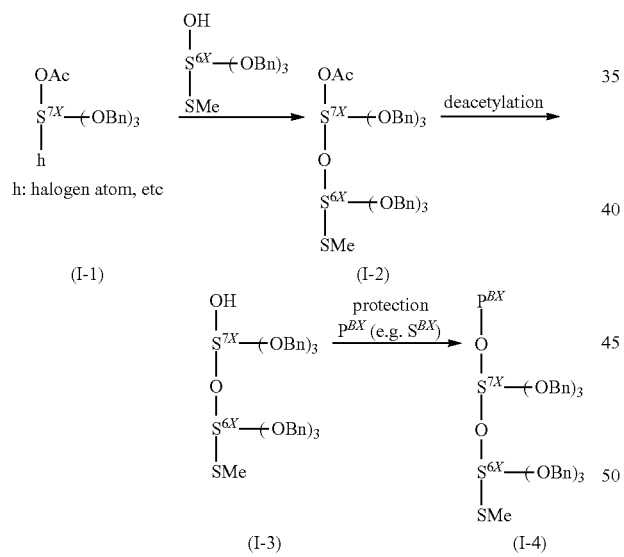

Reaction Scheme 2

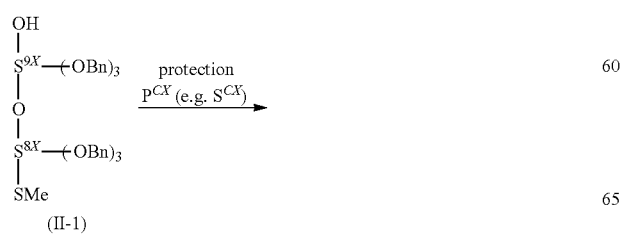

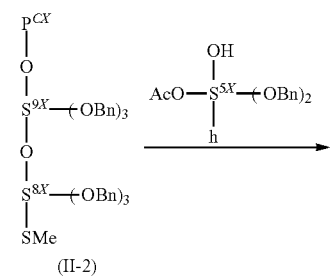

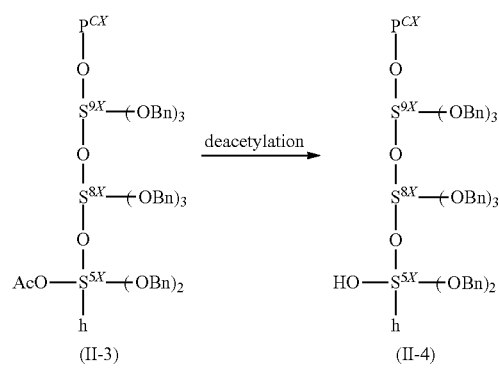

Reaction Scheme 3

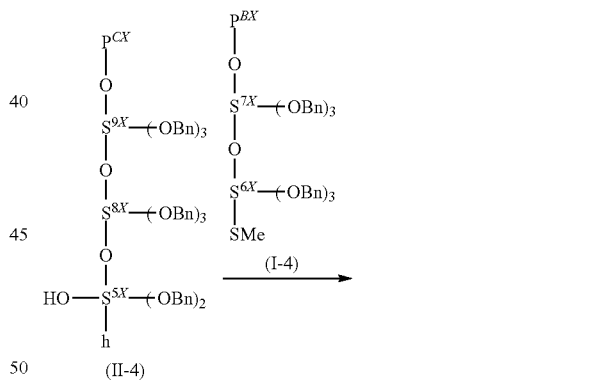

Reaction Scheme 4

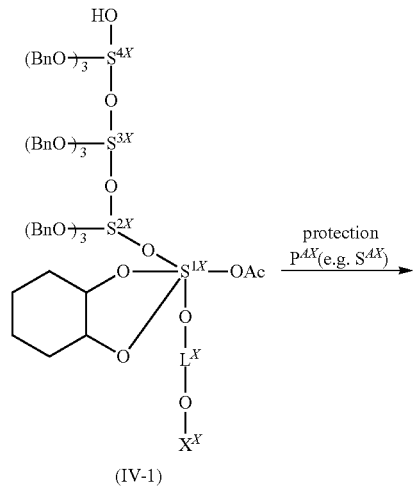

(IV-1)

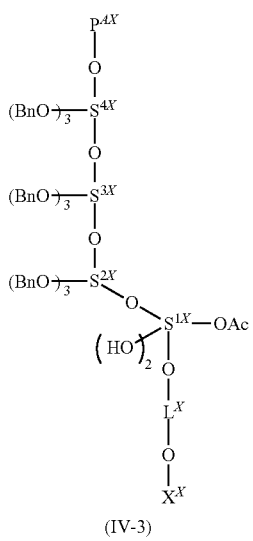

(IV-3)

Reaction Scheme 5

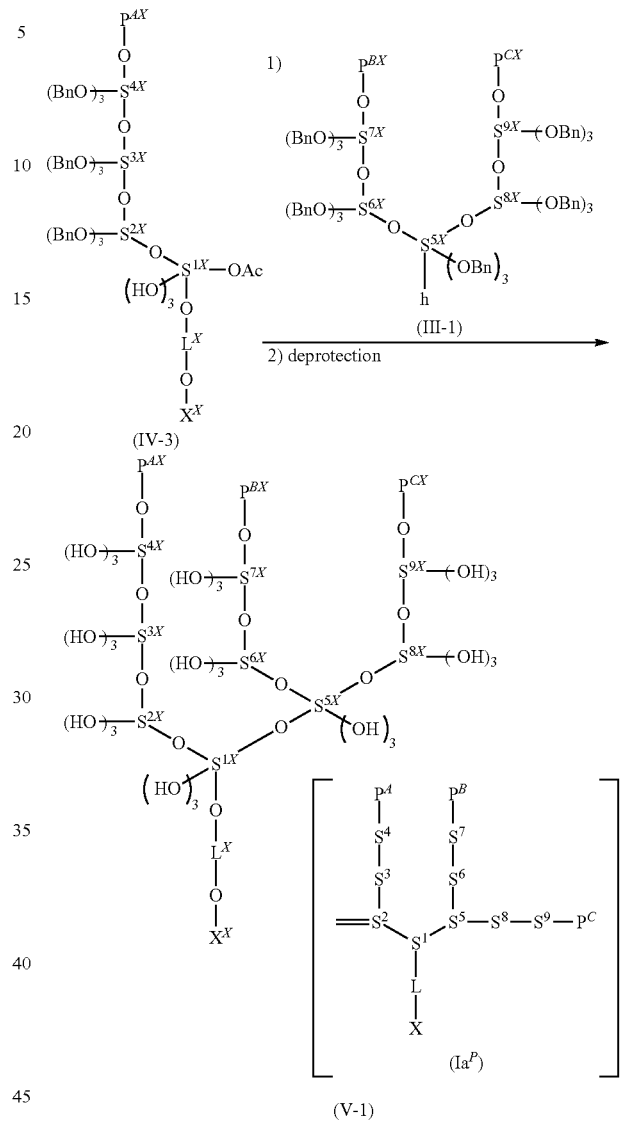

Organic synthetic reactions such as those for protection, deprotection, deacetylation, and sugar addition can be carried out by methods known per se. Furthermore, as desired, a protected compound of the present invention can be produced by carrying out commonly known deprotection reactions, acylation reactions, alkylation reactions, hydrogenation reactions, oxidation reactions, reduction reactions, carbon chain extension reactions, and substituent exchange reactions, singly or in combination of two or more thereof. These reactions are described in, for example, Japanese Patent Kokai Publication No. 2004-244583, documents disclosed in Examples below, and other publications such as "Protective Groups in Organic Synthesis", John Wiley & Sons Inc., and "Shin-Jikken Kagaku Kouza 14[V]" (Maruzen).

Known methods of total synthesis of naturally occurring sugar chains may be referenced to in producing a protected compound of the present invention. For example, a high mannose type sugar chain can be totally synthesized by a method described in Japanese Patent Kokai Publication No. 2004-

244583 and references disclosed in Examples below, a complex type sugar chain can be totally synthesized by a method described in Seifert et al., Angewandte Chemie International Edition 39: 531-534 (2000), and an O-linked sugar chain can be totally synthesized by a method described in Nakahara et al., Tetrahedron Letter 35: 3321-3324 (1994). Total synthesis of a hybrid type sugar chain can be achieved by using in combination methods described in the aforementioned references for high mannose type sugar chain and complex type sugar chain.

In preparing a synthesis intermediate of the present invention, it is preferable to use hydroxy-protecting groups showing different reactivities in the deprotection reaction in a plurality of units of P'' (n represents either A or B, and, if any, C or D) in a compound represented by the formula ($I^P$), ($Ia^P$) ($Ib^P$), ($Ic^P$), or ($II^P$). Examples of the hydroxy-protecting groups of different reactivities include 1) hydroxy-protecting groups that form an ether moiety after the protection reaction (hereinafter abbreviated ether-series protecting groups as required: e.g., methoxy-substituted benzyl group, nitro group-substituted benzyl group, trityl group, benzyl group, methoxymethyl group, methoxyethoxymethyl group), 2) acyl-series protecting groups (e.g., acetyl group, chloroacetyl group, levulinoyl group), and 3) silyl-series protecting groups (e.g., TBDMS, TBDPS, TMS, TIPS group). Also, because some of the hydroxy-protecting groups belonging to the same category described above have different deprotection conditions, such hydroxy-protecting groups can also be utilized. For example, when two kinds of hydroxy-protecting groups are used, useful combinations of hydroxy-protecting groups of different reactivities include a1) a combination of an ether-series protecting group and an acyl-series protecting group, a2) a combination of an ether-series protecting group and a silyl-series protecting group, a3) a combination of an acyl-series protecting group and a silyl-series protecting group, a4) a combination of two kinds of ether-series protecting groups of different deprotection conditions, a5) a combination of two kinds of acyl-series protecting groups of different deprotection conditions, and a6) a combination of two kinds of silyl-series protecting groups of deprotection conditions. When three kinds of hydroxy-protecting groups are used, useful combinations of hydroxy-protecting groups of different reactivities include b1) a combination of an ether-series protecting group, an acyl-series protecting group and a silyl-series protecting group, b2) a combination of two kinds of ether-series protecting groups of different deprotection conditions, and an acyl-series protecting group or a silyl-series protecting group, b3) a combination of two kinds of acyl-series protecting groups of different deprotection conditions, and an ether-series protecting group or a silyl-series protecting group, b4) a combination of two kinds of silyl-series protecting groups of different deprotection conditions, and an ether-series protecting group or an acyl-series protecting group, b5) a combination of three kinds of ether-series protecting groups of different deprotection conditions, b6) a combination of three kinds of acyl-series protecting groups of different deprotection conditions, and b7) a combination of three kinds of silyl-series protecting groups of different deprotection conditions.

2. Library and a Method of Production Thereof

The present invention also provides a library comprising two or more kinds of protected compounds of the present invention. The library of the present invention can comprise sugar chain compounds represented by the formulas (I) and (I') above, and can further comprise, as required, a sugar chain compound represented by the formula (I'') and/or the formula (I'''):

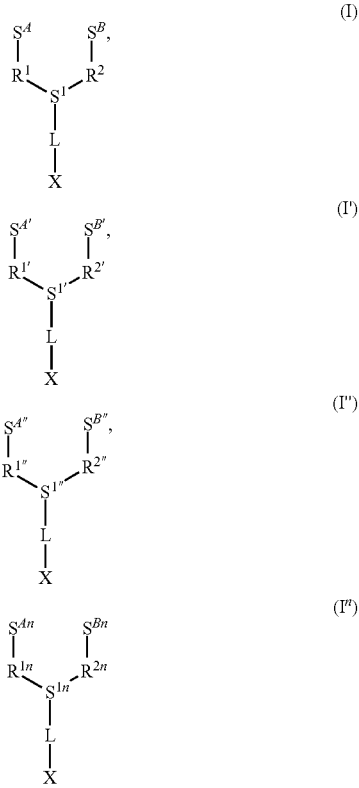

In the formulas (I'), (I''), and (I''') above, $R^{1\prime}$, $R^{1\prime\prime}$, and $R^{1\prime n}$ can independently have the same definition as that for $R^1$; $R^{2\prime}$, $R^{2\prime\prime}$ and $R^{2\prime n}$ can independently have the same definition as that for $R^2$; $S^{A\prime}$, $S^{A\prime\prime}$, and $S^{A\prime n}$ can independently have the same definition as that for $S^A$; $S^{B\prime}$, $S^{B\prime\prime}$, and $S^{B\prime n}$ can have the same definition as that for $S^B$; n (integer) represents a '-number (i.e., n+1 indicates the number of different kinds of protected compounds contained in the library of the present invention), and may be, for example, 1 or more, 2 or more, 3 or more, 4 or more, or 5 or more; n can also be, for example, 9 or less, 7 or less, or 5 or less.

Compounds represented by the formulas (I) and (I''') above (n is 2 or more as described above), contained in the library of the present invention, can be those wherein $R^1$ and $R^{1\prime n}$ are the same sugar chains, and/or $R^2$ and $R^{2\prime n}$ are the same sugar chains. Such compounds can also be those wherein $S^A$ and $S^n$ are different sugar residues, and/or $S^B$ and $S^n$ are different sugar residues, with preference given to a case where $S^A$, $S^B$, $S^{A\prime n}$, and $S^{B\prime n}$ are mutually different sugar residues. Such compounds can further be those wherein, provided that at least one of $R^1$, $R^{1\prime n}$, $R^2$, and $R^{2\prime n}$ is a branched sugar chain having at a terminus thereof a protective sugar residue, at least one, preferably two, more preferably three, most preferably all, of the protective sugar residues, and $S^A$, $S^B$, $S^{A\prime n}$, and $S^{B\prime n}$, can be mutually different sugar residues. Examples of (I''') include (Ia'''), (Ib'''), and (Ic''').

The library of the present invention is not subject to limitation, as long as it comprises a plurality of kinds of protected compounds of the present invention, and examples include a library comprising a plurality of kinds of protected compounds of the present invention contained in the same solution (e.g., glycosidase reaction solution), a library comprising a plurality of kinds of protected compounds of the present invention contained in the same section or different sections of the same container (plate, tube) (e.g., protected compounds contained in different wells of a multiwell plate), a library comprising a plurality of kinds of protected compounds of the present invention immobilized on the same substrate (e.g., supports such as a planar plate and particles), a population of different substrates on which a plurality of kinds of protected compounds of the present invention are immobilized, or a library of a plurality of kinds of protected compounds of the present invention bound to the same molecule (e.g., peptide) (e.g., peptides and proteins wherein a plurality of kinds of sugar chain compounds are bound to different amino acid residues).

The library of the present invention can be produced by combining a sugar chain compound of the formula (I) above and a sugar chain compound of the formula (I″) above (e.g., formulas (I′) and (I″)). The present invention also provides such a production method.

The step for combining a sugar chain compound of the formula (I) above and a sugar chain compound of the formula (I″) above can be performed by, for example, a) adding a plurality of kinds of protected compounds to the same section or different sections of the same solution or container, b) immobilizing a plurality of kinds of protected compounds onto the same substrate, c) immobilizing a plurality of kinds of protected compounds onto different substrates, and populating substrates with such protected compounds immobilized thereon, d) binding a plurality of kinds of protected compounds to the same molecule, or e) polymerizing a plurality of kinds of protected compounds (e.g., formation of a glycopeptide or glycoprotein by polymerization of amino acid residues bound to a plurality of kinds of protected compounds) and the like.

3. Methods of Producing a Given Sugar Chain Compound from Protected Sugar Chain Compound, and Sugar Chain Compound Obtained by the Method The present invention also provides a method of producing a sugar chain compound, which comprises treating a protected compound of the present invention or a library comprising two or more kinds of protected compounds with glycosidases. Useful glycosidases include the above-described exoglycosidases and endoglycosidases. In treating a protected compound of the present invention with glycosidases, the first-reacting glycosidase is exemplified by endoglycosidases capable of removing two or more sugar units, in addition to exoglycosidases. For example, provided that the protected compound of the present invention is a compound represented by the formula (II), it is also preferable to react an endoglycosidase capable of removing disaccharide units (e.g., disaccharide units composed of $S^A$ and Man). The protected compound subjected to this treatment and a library comprising the same can be those isolated and/or purified.

Treatment of a protected compound of the present invention or a library comprising two or more kinds of protected compounds with glycosidases is performed by a method known per se. For example, this treatment can be performed under appropriate conditions (e.g., pH, salt concentrations, temperature, reaction time) that allow the glycosidases used to exhibit their activity and the desired product to be obtained. This treatment may also be performed using a glycosidase-immobilized column. A desired sugar chain compound can easily be obtained by passing a protected compound of the present invention or a library comprising two or more kinds of protected compounds through the glycosidase-immobilized column, and then recovering the eluent. These treatments may be performed in parallel at the same time. For example, a desired sugar chain compound can be obtained by dispensing a protected compound of the present invention into different sections of the same container (e.g., different wells of a multiwell plate), and then adding different glycosidases or a glycosidase cocktail to each section.

The present invention also provides a sugar chain compound obtained by the production method described above (glycosidase decomposition product) and a library comprising two or more kinds of such sugar chain compounds.

For example, the sugar chain compound of the present invention can be a non-naturally occurring sugar chain compound prepared by treating a protected compound of the present invention or a library thereof with glycosidases. More specifically, the sugar chain compound of the present invention can be (a) (a1) a glycosidase decomposition product of protected high mannose type sugar chain compound, which retains either the sugar residues $S^B$ or $S^C$ or both the sugar residues $S^B$ and $S^C$, represented by the formula (II), (a2) a glycosidase decomposition product of protected high mannose type sugar chain compound, which retains as $S^A$ a sugar residue other than D-glucose, represented by the formula (II), (b) a glycosidase decomposition product of protected complex type sugar chain compound, which retains at least one, or at least two or three, of the sugar residues $S^A$, $S^B$, $S^C$, and $S^D$, represented by the formula (Ib) [wherein $S^1$ to $S^{11}$ and L are the same as those for natural complex type sugar chain, $S^A$, $S^B$, $S^C$, and $S^D$ are any sugar residues], or (c) a glycosidase decomposition product of protected O-linked sugar chain compound, which retains one of the sugar residues $S^A$ and $S^B$, represented by the formula (Ic) [wherein $S^1$ to $S^3$ and L are the same as those for natural O-linked sugar chain, $S^A$ and $S^B$ are any sugar residues]. Without the present inventors' idea that a protected compound of the present invention is synthesized and specifically cleaved by glycosidase, whereby a sugar chain compound is specifically and systematically prepared, there has been no motivation for preparing such a sugar chain compound. On the other hand, according to the above-described idea of the present inventors, a motivation for producing such a sugar chain compound as an intermediate in a reaction for producing a naturally occurring sugar chain with glycosidase arises.

For example, as the intermediate in the reaction for producing a naturally occurring sugar chain, the sugar chain compounds shown below are preferable ($S^A$, $S^B$, $S^C$, and X have the same definitions as those shown above, but conditions (a1) or (a2) above are satisfied).

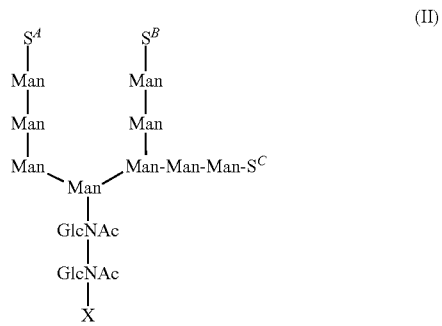
(II)

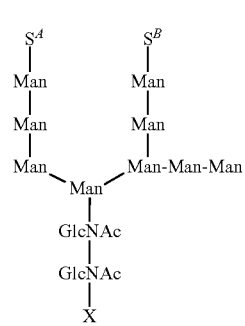 (IIa1)
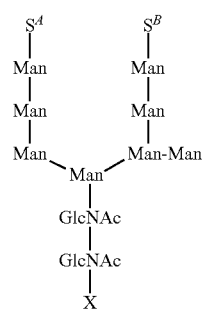 (IIa2)
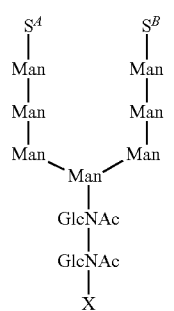 (IIa3)
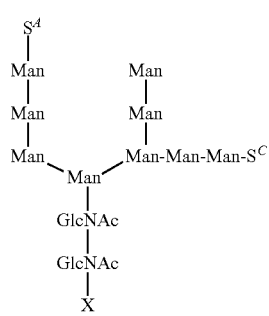 (IIa4)
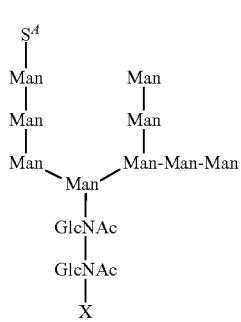 (IIa5)
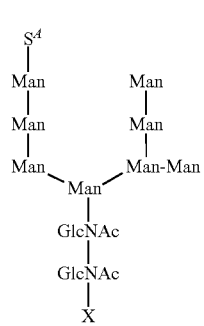 (IIa6)
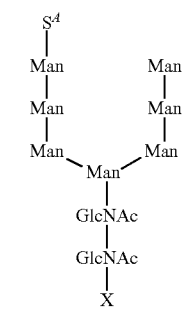 (IIa7)
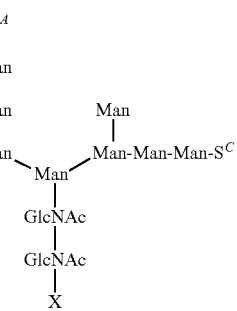 (IIa8)
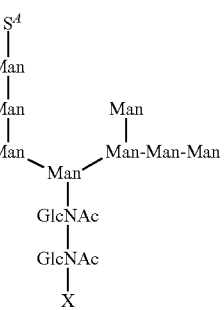 (IIa9)
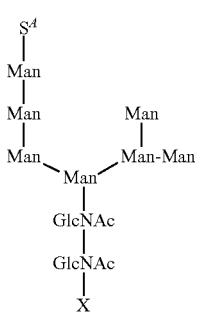 (IIa10)

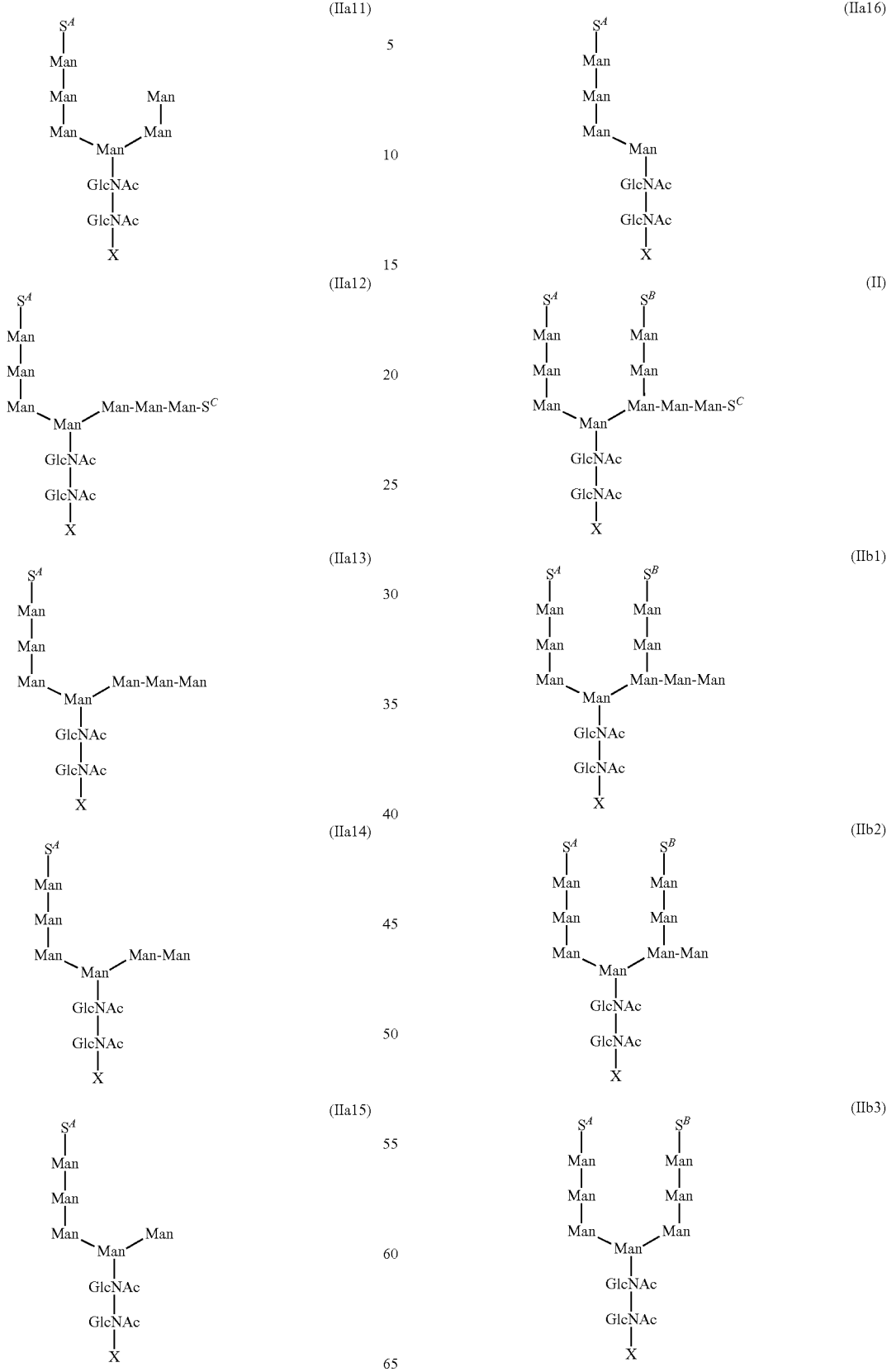

(IIb4)

```
           S^B
           |
    Man    Man
    |      |
    Man    Man
    |      |
    Man    Man-Man-Man-S^C
       \  /
        Man
        |
        GlcNAc
        |
        GlcNAc
        |
        X
```

(IIb5)

```
           S^B
           |
    Man    Man
    |      |
    Man    Man
    |      |
    Man    Man-Man-Man
       \  /
        Man
        |
        GlcNAc
        |
        GlcNAc
        |
        X
```

(IIb6)

```
           S^B
           |
    Man    Man
    |      |
    Man    Man
    |      |
    Man    Man-Man
       \  /
        Man
        |
        GlcNAc
        |
        GlcNAc
        |
        X
```

(IIb7)

```
           S^B
           |
    Man    Man
    |      |
    Man    Man
    |      |
    Man    Man
       \  /
        Man
        |
        GlcNAc
        |
        GlcNAc
        |
        X
```

(IIb8)

```
           S^B
           |
           Man
           |
    Man    Man
    |      |
    Man    Man-Man-Man-S^C
       \  /
        Man
        |
        GlcNAc
        |
        GlcNAc
        |
        X
```

(IIb9)

```
           S^B
           |
           Man
           |
    Man    Man
    |      |
    Man    Man-Man-Man
       \  /
        Man
        |
        GlcNAc
        |
        GlcNAc
        |
        X
```

(IIb10)

```
           S^B
           |
           Man
           |
    Man    Man
    |      |
    Man    Man-Man
       \  /
        Man
        |
        GlcNAc
        |
        GlcNAc
        |
        X
```

(IIb11)

```
           S^B
           |
           Man
           |
    Man    Man
    |      |
    Man    Man
       \  /
        Man
        |
        GlcNAc
        |
        GlcNAc
        |
        X
```

(IIb12)

```
           S^B
           |
           Man
           |
           Man
           |
    Man    Man-Man-Man-S^C
       \  /
        Man
        |
        GlcNAc
        |
        GlcNAc
        |
        X
```

(IIb13)

```
           S^B
           |
           Man
           |
           Man
           |
    Man    Man-Man-Man
       \  /
        Man
        |
        GlcNAc
        |
        GlcNAc
        |
        X
```

-continued
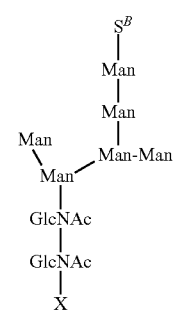
(IIb14)
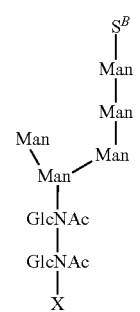
(IIb15)
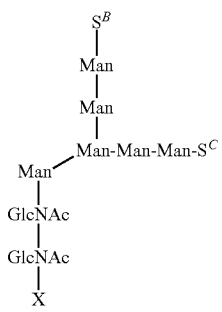
(IIb16)
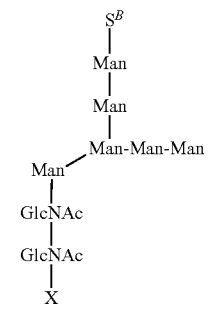
(IIb17)
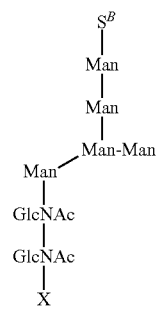
(IIb18)
-continued
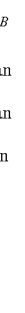
(IIb19)
(II)
(IIc1)
(IIc2)
(IIc3)

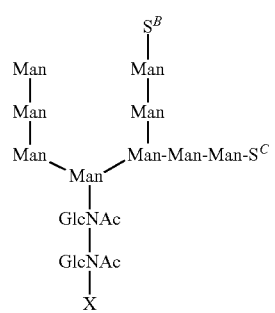 (IIc4)
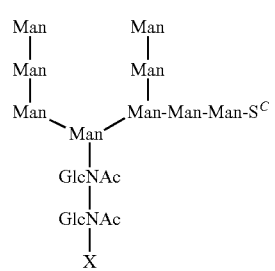 (IIc5)
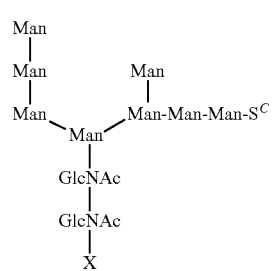 (IIc6)
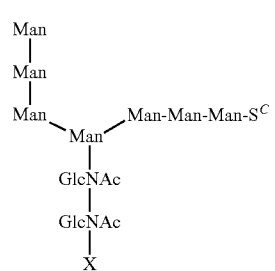 (IIc7)
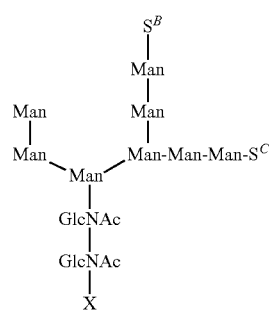 (IIc8)
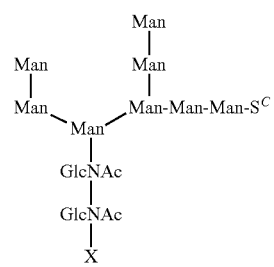 (IIc9)
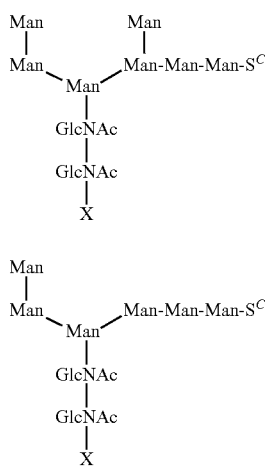 (IIc10)
(IIc11)
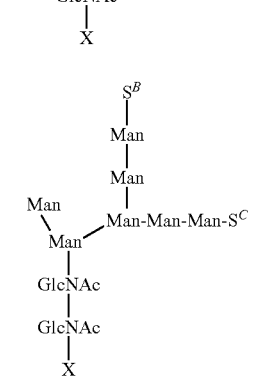 (IIc12)
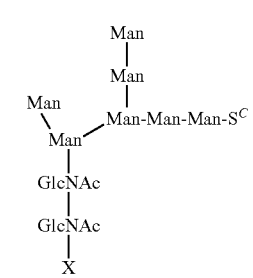 (IIc13)
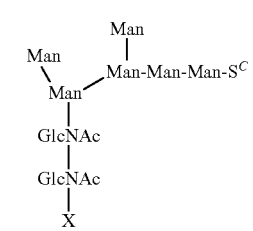 (IIc14)

-continued

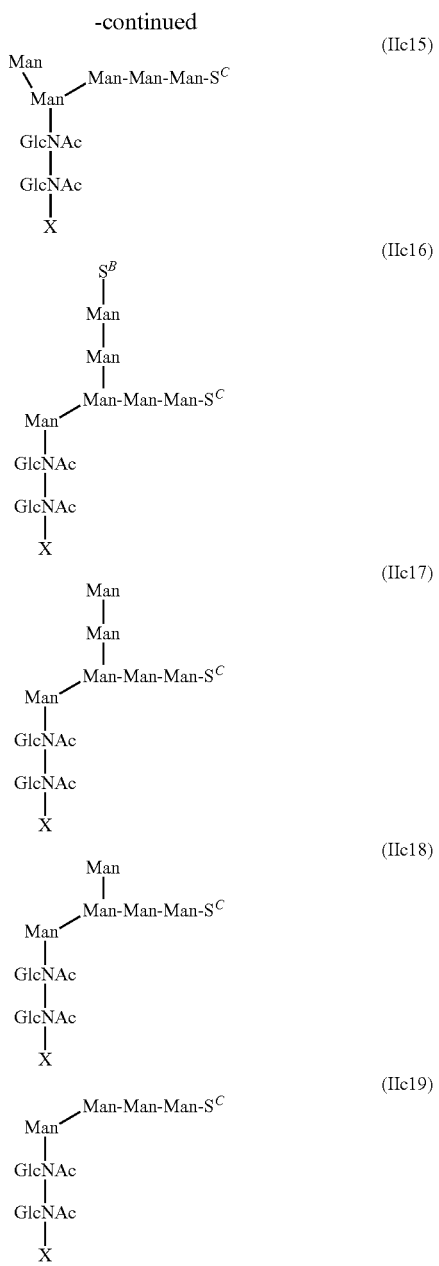

The present invention also provides a method of producing a sugar chain compound, which comprises synthesizing a protected compound of the present invention, and treating the protected compound with glycosidases. Synthesis of a protected compound and treatment of a protected compound of the present invention with glycosidases can be performed as described above. A protected compound of the present invention may, for example, be a protected sugar chain compound wherein at least one sugar residue is introduced to the non-reducing terminus of a sugar chain having the same structure as a naturally occurring sugar chain. The number of sugar residues introduced can be any one up to the number of non-reducing termini of the sugar chain having the same structure as that of a naturally occurring sugar chain, and can, for example, be 4 or less, 3 or less, preferably 1 or 2.

Naturally occurring sugar chains can exhibit various biological activities. For example, naturally occurring sugar chains play roles in the formation of higher-order structures of proteins, proteolysis signaling and the like. Abnormalities of the protein quality control mechanism in the endoplasmic reticulum are considered to be involved in diseases caused by protein folding abnormalities (e.g., Alzheimer's disease), and the involvement of sugar chain synthase deficiency in diseases has also been reported (see, e.g., Helenius et al., Science 291: 2364-2369 (2001); Ellgaard et al., Nature Reviews, Molecular Cell Biology 4: 181-191(2003); McCracken et al., BioEssays 25: 868-877 (2003)). Therefore, such glycosidase decomposition products (non-naturally occurring sugar chain compounds) are useful as, for example, intermediates in the synthesis of the above-described naturally occurring bioactive sugar chains.

4. Reagent and Kit

The present invention provides a reagent and kit comprising a protected compound of the present invention or a salt thereof or a library thereof, or any glycosidase decomposition product thereof, or a synthesis intermediate for a protected compound of the present invention.

For example, the reagent and kit of the present invention may further comprise a glycosidase, when comprising a protected compound and library of the present invention, or any glycosidase decomposition product thereof. The glycosidase contained in the kit of the present invention may be any one kind or more (e.g., 2, 3 or 4 kinds), but may comprise two kinds or more, preferably three kinds or more, or four kinds or more, of different exoglycosidases capable of cleaving protective sugar residues.

The reagent and kit of the present invention are useful for, for example, selectively and systematically preparing a sugar chain compound.

It is to be understood that this invention is not limited to particular compounds, libraries or methods, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a compound" optionally includes a combination of two or more such compounds, and the like.

Abbreviations used herein for substituents, protecting groups and reagents are defined as follows:

Bn: benzyl

Ac: acetyl

All: allyl

Phth: phthaloyl

Bz: benzoyl

CA: monochloroacetylacetic acid

AgOTf: silver triflate

Me: methyl

The references cited herein, including patents and patent application specifications, are hereby incorporated in their entireties by reference, to the extent that they have been disclosed herein.

The present invention is hereinafter described in more detail by means of the following examples, which, however, are not to be construed as limiting the present invention.

EXAMPLES

Materials

Galactosidase from *A. oryzae*, α-mannosidase from Jack beans, GlcNAc'ase from Jack beans used in the following experiments were purchased from Sigma. Glucosidase II from *A. oryzae* was obtained as follows. The bacteria of *Aspergillus oryzae* RIB40 (ATCC number: 42149) were cultured in 100 ml of DPY (2% dextrin, 1% polypeptone, 0.5% yeast extract, 0.5% $KH_2PO_4$, 0.05% $MgSO_4.7H_2O$, pH 5.5) medium at 30° C. for 18 hr, and then the bacteria were recovered. After the bacteria were freezed in nitrogen liquid, they were disrupted, and dissolved in 6 ml of extraction buffer (50 mM Tris (pH 7.5), 2 mM PMSF, 1:100 PIC (protein inhibitor cocktail)). After insoluble materials were removed by centrifugation (3,000×g, 10 min, 4° C.), membrane fraction was recovered by ultracentrifugation (20,000×g, 20 min, 4° C.). The obtained membrane fraction was dissolved in extraction buffer containing 600 μL of 1% Triton X-100, and used as crude enzyme solution.

Production Example 1

Synthesis of [GlcNAc-Mannobiosyl 1-6(Galactosyl Mannobiose) 1-3 Mannosyl] 1-6 Glucosyl Trimannosyl Core Trisaccharide The title compound was synthesized with reference to the following methods. The references are as follows.
1) Matsuo, I., Wada, M., Manabe, S., Yamaguchi, Y., Otake, K., Kato, K., and Ito, Y. (2003) J. Am. Chem. Soc., 125, 3402.
2) Matsuo, I., and Ito, Y. (2003) Carbohydr. Res., 338, 2163.
3) Matsuo, I., Kashiwagi, T., Totani, K., and Ito, Y. (2005) Tetrahedron Lett., 46, 4197.
4) Ito, Y., Ohnishi, Y., and Ogawa, T. (1998) Synlett, 1102.
5) Matsuo, I., Wada, M., and Ito, Y. (2002) Tetrahedron Lett., 43, 3273.
7) Matsuo, I., Isomura, M., Miyazaki, T., Sakakibara, T., and Ajisaka, K. (1998) Carbohydr Res., 305, 401.
8) Matsuo, I., Miyazaki, T., Isomura, M., Sakakibara, T., and Ajisaka, K. (1998) J. Carbohydr. Chem., 17, 1249.

1.1. Synthesis of Mannobiose

A mixture of SMe-mannose acceptor (276.1 mg, 0.573 mmol), AgOTf (288.2 mg, 1.12 mmol) and molecular sieves 4A (5 g) in dry toluene (5 mL) was stirred at −40° C. for 30 min. A solution of Cl-donor (298.0 mg, 0.577 mmol) in dry toluene (5 mL) was added and the mixture was stirred at −10° C. for 1 h and at ambient temperature for 12 h. The reaction was quenched with TEA (1 mL). The reaction mixture was diluted with EtOAc and filtered through Silica gel. The filtrate was washed with aq. $NaHCO_3$ and brine, successively, dried over $Na_2SO_4$ and concentrated in vacuo. The residue was purified by silica gel column chromatography (toluene:EtOAc, 20:1-9:1) to afford mannobiose (310.7 mg, 57%).

$^1$H NMR (400 MHz, $CDCl_3$) δ 7.326-7.174 (m, 30H), 5.205 (bs, 1H), 5.136 (bs, 1H), 4.905 (d, 1H, J=11.0 Hz), 4.832 (d, 1H, J=10.7 Hz), 4.670-4.487 (m, 1H), 4.368 (bd, 1H, J=11.7 Hz), 4.257 (dd, 1H, J=5.3 and 11.7 Hz), 4.291-4.047 (m, 2H), 3.965-3.765 (m, 6H), 3.678 (bd, 1H, J=11.2 Hz), 2.086 (s, 3H), 2.101 (s, 3H);

MALDI-TOF mass calcd for $C_{57}H_{62}O_{11}SNa$ $(M+Na)^+$ 977.4, found 977.9.

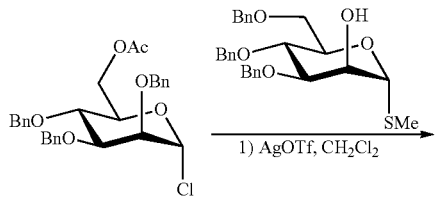

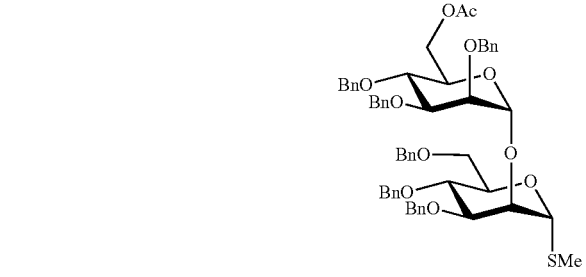

1.2. Synthesis of Mannobiose Acceptor

To a stirred solution of mannobiose (310.7 mg, 0.325 mmol) in THF:MeOH (4:1, 5 mL) was added 1M NaOMe/MeOH (15 μL) at 0° C. The mixture was stirred for 1 h, neutralized with 1N HCl (20 μL). The reaction mixture was diluted with EtOAc and washed with aq. $NaHCO_3$ and brine, successively, dried over $Na_2SO_4$ and concentrated in vacuo to afford mannobiose acceptor (279.7 mg, 94%).

$^1$H NMR (400 MHz, $CDCl_3$) δ 7.348-7.172 (m, 30H), 5.214 (bs, 1H), 5.130 (bs, 1H), 4.907 (d, 1H, J=11.2 Hz), 4.822 (d, 1H, J=10.4 Hz), 4.669-4.490 (m, 10H), 4.052 (bs, 1H), 3.930-3.686 (m, 11H), 2.093 (s, 3H); MALDI-TOF mass calcd for $C_{55}H_{62}O_{11}SNa$ $(M+Na)^+$ 935.4, found 935.9.

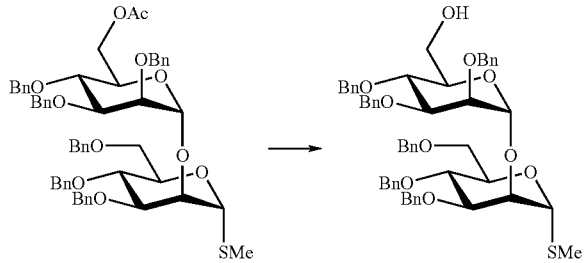

1.3. Coupling of Mannobiose Acceptor and Galactose Donor

A mixture of mannobiose acceptor (279.7 mg, 0.306 mmol), AgOTf (500.0 mg, 1.946 mmol) and molecular sieves 4A (2 g) in dry toluene (5 mL) was stirred at −40° C. for 30 min. A solution of Cl-galactose donor (317.2 mg, 0.516 mmol) in dry $CH_2Cl_2$ (5 mL) was added and the mixture was stirred at −10° C. for 1 h and at 40° C. for 24 h. The reaction was quenched with TEA (1 mL). The reaction mixture was diluted with EtOAc and filtered through Celite. The filtrate was washed with aq. $NaHCO_3$ and brine, successively, dried over $Na_2SO_4$ and concentrated in vacuo. The residue was purified by PTLC (toluene:EtOAc, 5:1) to afford galactosyl mannobiose donor (295.3 mg, 65%).

$^1$H NMR (400 MHz, $CDCl_3$) δ 8.104-7.151 (m, 50H), 5.598 (bd, 1H, J=3.6 Hz), 5.891 (dd, 1H, J=8.0 and 10.0 Hz), 5.580 (dd, 1H, J=3.6 and 10.4 Hz), 5.199 (bs, 1H), 5.055 (bs, 1H), 4.802-4.772 (m, 2H), 4.663-4.261 (m, 14H), 4.102-3.674 (m, 11H), 2.118 (s, 3H); MALDI-TOF mass calcd for $C_{89}H_{86}O_{19}SNa$ (M+Na)$^+$ 1513.54, found 1514.19.

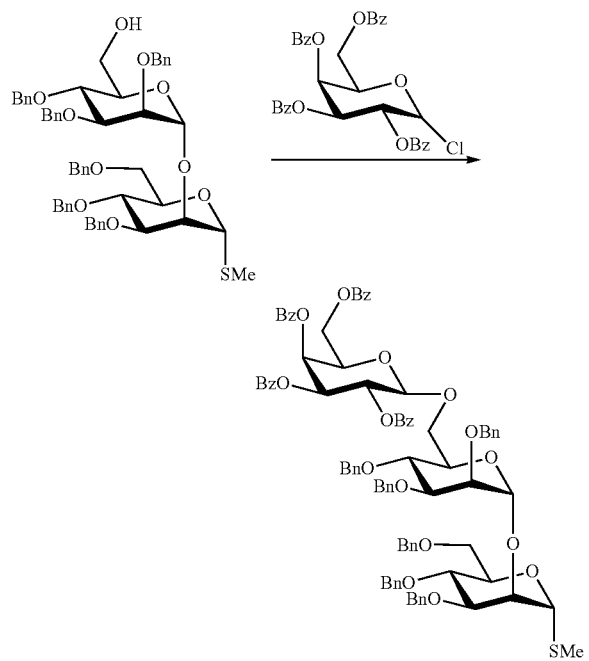

1.4. Coupling of Mannobiose Acceptor and GlcNAc Donor

To a stirred mixture of $Cp_2HfCl_2$ (269.5 mg, 0.710 mmol), AgOTf (365.5 mg, 1.423 mmol), and molecular sieves 4A (3 g) in dry $CH_2Cl_2$ (5 mL) was added a solution of mannobiose acceptor (541.1 mg, 0.593 mmol) and GlcNAc-donor (354.0 g, 0.609 mmol) in dry $CH_2Cl_2$ (10 mL) at −78° C. The mixture was stirred for 2 h and at −40° C. for 1 h. Insoluble materials were removed by passage through silica gel and the filtrate was then diluted with EtOAc, washed with brine, aq. $NaHCO_3$ and brine successively, dried over $Na_2SO_4$, and evaporated in vacuo. The residue was purified by silica gel column chromatography (toluene:EtOAc, 15:1-10:1) to afford compound GlcNAc-mannobiose donor (393.4 mg, 45%).

$^1$H NMR (400 MHz, CDCl$_3$) δ 7.347-6.830 (m, 49H), 5.246 (d, 1H, J=8.4 Hz), 5.128 (bs, 1H), 4.934 (bs, 1H), 4.750-4.273 (m, 18H), 4.200 (bd, 1H, J=10.4 Hz), 3.994 (m, 2H), 3.786-3.611 (m, 15H), 2.111 (s, 3H); MALDI-TOF mass calcd for $C_{90}H_{91}O_{16}NSNa$ (M+Na)$^+$ 1496.6, found 1497.5.

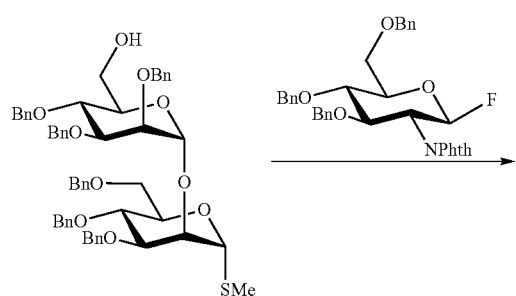

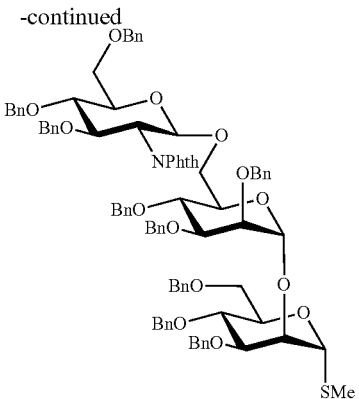

1.5. Synthesis of 3-Acetylated Mannose Acceptor

The 6-CA-mannose (533.6 mg, 1.008 mmol) was dissolved in pyridine (0.8 mL). To the mixture was added acetic anhydride (0.4 mL) at 0° C. and stirred for 2 h. The reaction mixture was concentrated in vacuo. The residue was treated with NBS (535.0 mg, 3.009 mmol) and DAST (135 μL, 1.022 mmol) in $CH_2Cl_2$ (5 mL) at −40° C. The reaction mixture was stirred at −30° C. for 1 h and then at ambient temperature. After 12 h, MeOH (0.5 mL) was added and the mixture was diluted with EtOAc, washed successively with aq. $NaHCO_3$ and brine. The organic layer was dried over $Na_2SO_4$ and concentrated in vacuo. The residue was treated with DABCO (432 mg) at 50° C. for 2 h. The mixture was neutralized with Amberlist 15 E [H$^+$]. Insoluble materials were removed by filtration and the filtrate was concentrated in vacuo. The residue was purified by silica gel column chromatography (toluene:EtOAc, 10:1-4:1) to give 3-acetylated mannose acceptor (117.3 mg, 28%).

$^1$H NMR (400 MHz, CDCl$_3$) δ 7.377-7.282 (m, 10H), 5.525 (dd, 1H, J=2.0 and 50.4 Hz), 5.216 (m, 1H), 4.745-4.617 (m, 4H), 4.092 (t, 1H, J=9.6 Hz), 4.006 (bs, 1H), 3.863-3.758 (m, 3H), 1.976 (s, 3H);

MALDI-TOF mass calcd for $C_{22}H_{25}O_6FNa$ (M+Na)$^+$ 427.2, found 427.7.

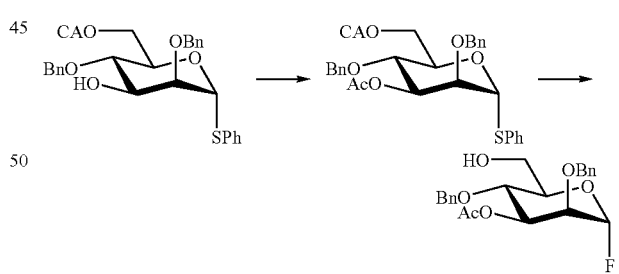

1.6. Coupling of GlcNAc-Mannobiose Donor and 3-Acetylated Mannose Acceptor

A solution of 3-acetylated mannose acceptor (45.0 mg, 0.111 mmol), GlcNAc-mannobiose donor (181.0 mg, 0.123 mmol), and molecular sieves 4A (2 g) in dry toluene (20 mL) was stirred at 0° C. for 1 h, then added 1M MeOTf (0.2 mL, 0.2 mmol) in $ClCH_2CH_2Cl$. The reaction mixture was stirred at 40° C. for 24 h. The reaction was quenched with TEA (0.2 mL) at 0° C. The mixture was diluted with EtOAc and filtered through Celite. The filtrate was washed with aq. $NaHCO_3$, and brine. The organic layer was dried over $Na_2SO_4$ and concentrated in vacuo. The residue was purified by a PTLC (toluene:EtOAc, 5/1) to afford GlcNAc-mannobiosyl 3-acetylated mannose (172.8 mg, 84%).

$^1$H NMR (400 MHz, CDCl$_3$) δ 7.361-6.840 (m, 59H), 5.750 (bd, 1H, J=50.4 Hz), 5.240 (d, 1H, J=8.4 Hz), 4.884-3.500 (m, 48H), 1.974 (s, 3H);

MALDI-TOF mass calcd for C$_{111}$H$_{112}$O$_{22}$NFNa (M+Na)$^+$ 1854.06, found 1854.5.

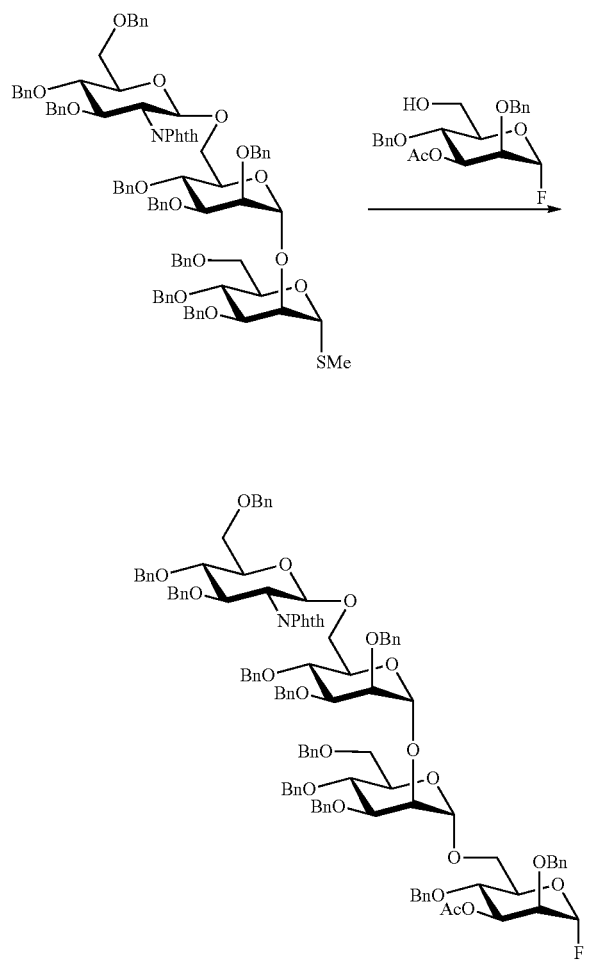

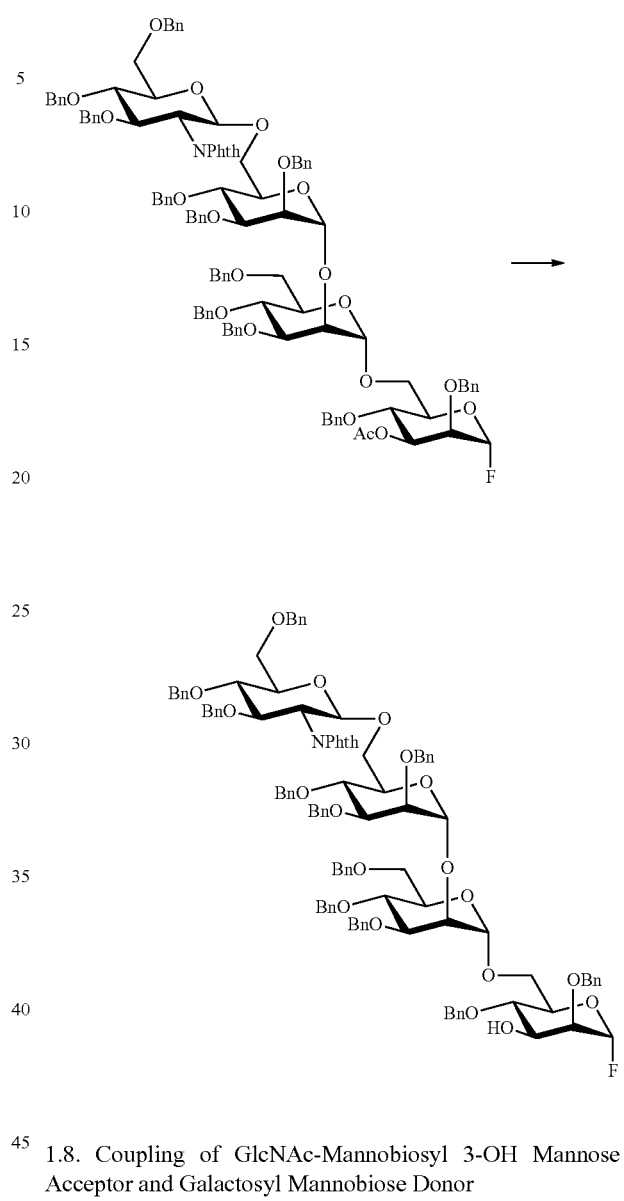

1.7. Synthesis of GlcNAc-Mannobiosyl 3-OH Mannose Acceptor

To a stirred solution of GlcNAc-mannobiosyl 3-acetylated mannose (172.8 mg, 0.932 mmol) in THF:MeOH (5:1, 6 mL) was added 1M NaOMe/MeOH (100 μL) at 0° C. The mixture was stirred for 1 h, neutralized with 1N HCl (200 μL). The reaction mixture was diluted with EtOAc and washed with aq. NaHCO$_3$ and brine successively, dried over Na$_2$SO$_4$ and concentrated in vacuo to afford GlcNAc-mannobiosyl 3-OH mannose acceptor (98.0 mg, 58%).

$^1$H NMR (400 MHz, CDCl$_3$) δ 7.361-6.840 (m, 59H), 5.809 (bd, 1H, J=49.2 Hz), 5.238 (d, 1H, J=8.4 Hz), 4.904 (bs, 2H), 4.849-4.752 (m, 6H), 4.645-4.253 (m, 17H), 4.183 (bd, 1H, J=10.8 Hz), 4.109 (bd, 1H, J=9.2 Hz), 3.974-3.506 (m, 22H), 2.395 (bd, 1H, J=9.6 Hz); MALDI-TOF mass calcd for C$_{109}$H$_{110}$O$_{21}$NFNa (M+Na)$^+$ 1810.8, found 1812.5.

1.8. Coupling of GlcNAc-Mannobiosyl 3-OH Mannose Acceptor and Galactosyl Mannobiose Donor A mixture of GlcNAc-mannobiosyl 3-OH mannose acceptor (98.0 mg, 0.055 mmol), Galactosyl-mannobiose donor (182.0 mg, 0.122 mmol), and molecular sieves 4A (2 g) in dry toluene (20 mL) was stirred at 0° C. for 1 h, then added 1M MeOTf (0.6 mL, 0.6 mmol) in ClCH$_2$CH$_2$Cl. The reaction mixture was stirred at 40° C. for 24 h. The reaction was quenched with TEA (1 mL) at 0° C. The mixture was diluted with EtOAc and filtered through Celite. The filtrate was washed with aq. NaHCO$_3$, and brine. The organic layer was dried over Na$_2$SO$_4$ and concentrated in vacuo. The residue was purified by a PTLC (toluene:EtOAc, 7/1) to afford GlcNAc-mannobiosyl 1-6(galactosyl mannobiose) 1-3 mannose donor (93.3 mg, 44%).

$^1$H NMR (400 MHz, CDCl$_3$) δ 8.104-6.804 (m, 109H), 5.959-5.916 (m, 2H), 5.683-5.541 (m, 2H), 5.261-5.104 (m, 3H), 4.862-3.419 (m, 76H);

MALDI-TOF mass calcd for C$_{197}$H$_{192}$O$_{40}$NFNa (M+Na)$^+$ 3253.29, found 3255.8.

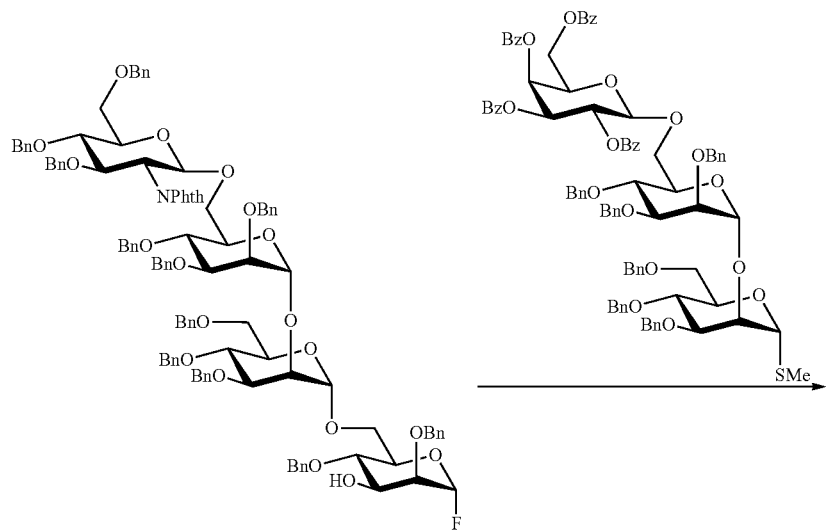

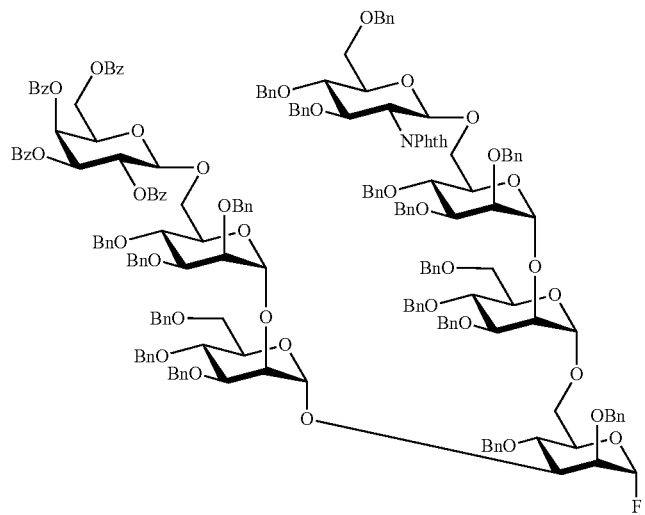

1.9. Synthesis of 3-OH Trimannosyl Core Trisaccharide Acceptor

Trimannosyl core trisaccharide (1.09 g, 0.422 mmol) was dissolved in DMF (3 mL) containing 10% HF/pyridine and transferred to 3 mL Teflon reaction vessels. It was compressed to 1.0 GPa and left at 30° C. for 12 h. The mixture was diluted with EtOAc and washed with aq. NaHCO$_3$ and brine successively. The organic layer was dried over Na$_2$SO$_4$ and concentrated in vacuo. The combined mixtures were purified by silica gel column chromatography (hexane:EtOAc, 5:1-1:1) to give compound 3-OH trimannosyl core trisaccharide acceptor (0.939 g, 94% yield).

$^1$H NMR (400 MHz, CDCl$_3$) δ 7.855-6.707 (m, 73H), 5.640-5.543 (m, 1H), 5.336-5.173 (m, 5H), 5.008-4.794 (m, 8H), 4.687-3.361 (m, 66H), 3.278 (bd, 1H, J=9.6 Hz), 3.177 (bd, 1H, J=9.6 Hz), 2.893-2.831 (m, 1H), 2.011 (s, 3H);

MALDI-TOF mass calcd for C$_{154}$H$_{160}$O$_{34}$N$_2$Na (M+Na)$^+$ 2604.1, found 2603.7.

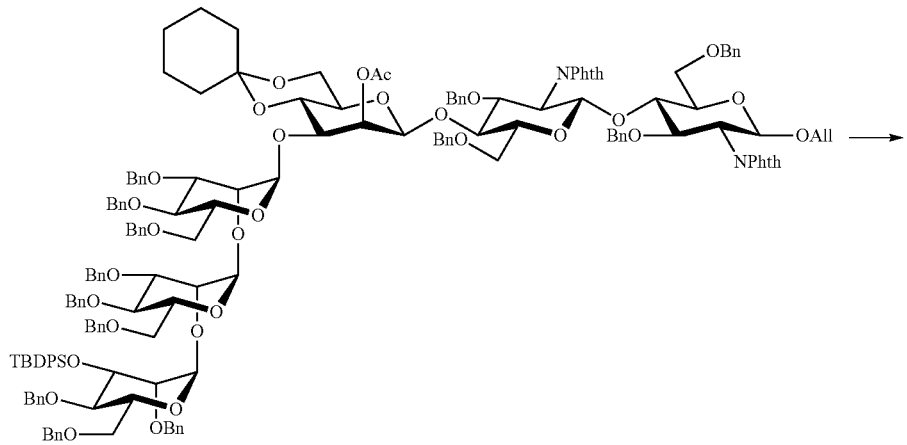

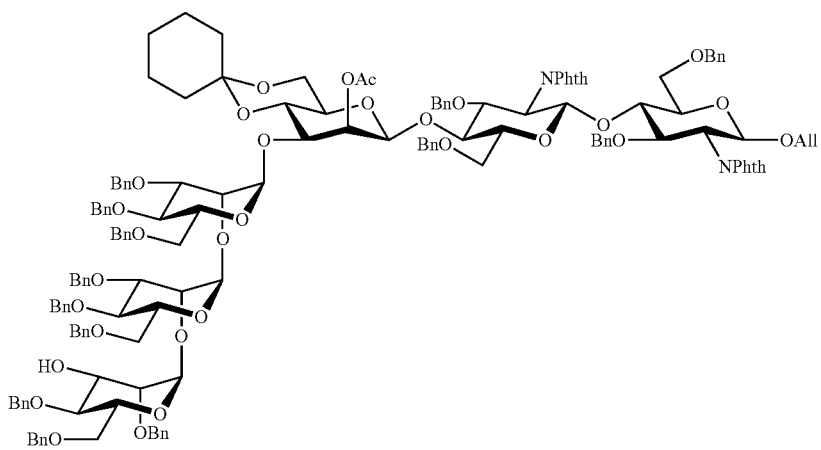

1.10. Coupling of 3-OH Trimannosyl Core Trisaccharide Acceptor and Glucose Donor To a stirred mixture of $Cp_2HfCl_2$ (225.0 mg, 0.528 mmol), AgOTf (319.0 g, 1.056 mmol), and molecular sieves 4A (2.6 g) in dry toluene/ether (2:1, 15 mL) was added a solution of 3-OH trimannosyl core trisaccharide acceptor (363.9 mg, 0.141 mmol) and Glucose-donor (257.3 mg, 0.440 mmol) in dry toluene (5 mL) at −40° C. The mixture was stirred for 2 h and at −10° C. for 12 h. Insoluble materials were removed by passage through silica gel and the filtrate was then diluted with EtOAc, washed with brine, aq. $NaHCO_3$ and brine successively, dried over $Na_2SO_4$, and evaporated in vacuo. The residue was purified by silica gel column chromatography (toluene:EtOAc, 15:1-10:1) to afford compound Glucosyl trimannosyl core trisaccharide (295.5 mg, 67%).

$^1$H NMR (400 MHz, $CDCl_3$) δ 7.985-6.727 (m, 93H), 6.070 (t, 1H, J=10.0 Hz), 5.641-5.522 (m, 2H), 3.367-5.332 (m, 2H), 5.220-5.514 (m, 3H), 5.006-4.703 (m, 5H), 4.674-3.359 (m, 66H), 3.278 (bd, 1H, J=8.8 Hz), 3.175 (bd, 1H, J=10.4 Hz), 2.903-2.843 (m, 1H), 1.999 (s, 3H);

MALDI-TOF mass calcd for $C_{188}H_{188}O_{42}N_2Na$ $(M+Na)^+$ 3168.2, found 3169.5.

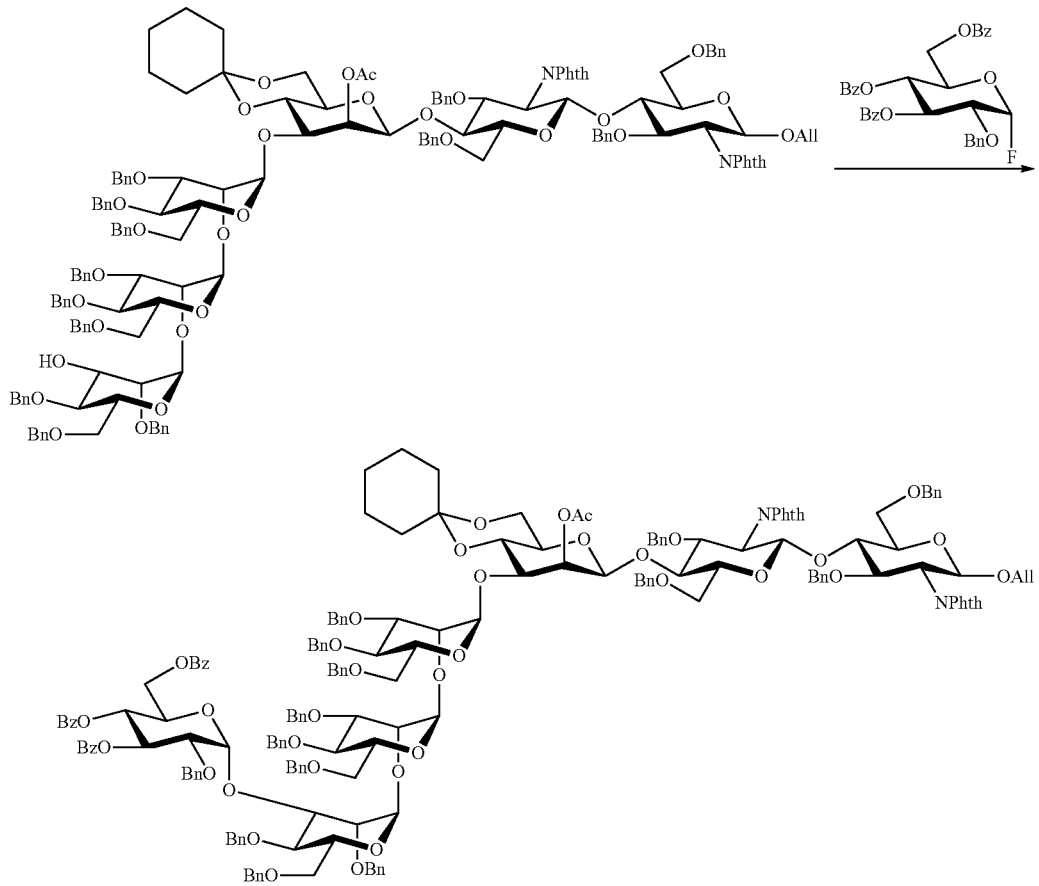

1.11. Synthesis of Glucosyl Trimannosyl Core Trisaccharide Acceptor

To a stirred solution of Glucosyl trimannosyl core trisaccharide (237.1 mg, 0.075 mmol) in dry CH$_3$CN was added p-toluenesulfonic acid monohydrate (72.3 mg, 0.381 mmol) and stirred for 1 h at room temperature. The reaction was quenched with TEA (0.1 mL) and concentrated in vacuo. The residue was purified by silica gel column chromatography (toluene:EtOAc, 5:1) to afford the Glucosyl trimannosyl core trisaccharide acceptor (221.8 mg, 96%).

$^1$H NMR (400 MHz, CDCl$_3$) δ 7.221-6.715 (m, 91H), 6.020 (t, 1H, J=7.2 Hz), 5.651-5.541 (m, 2H), 5.367-3.171 (m, 85H), 2.939 (m, 1H), 1.965 (s, 3H); MALDI-TOF mass calcd for C$_{182}$H$_{180}$O$_{42}$N$_2$Na (M+Na)$^+$ 3088.2, found 3089.9.

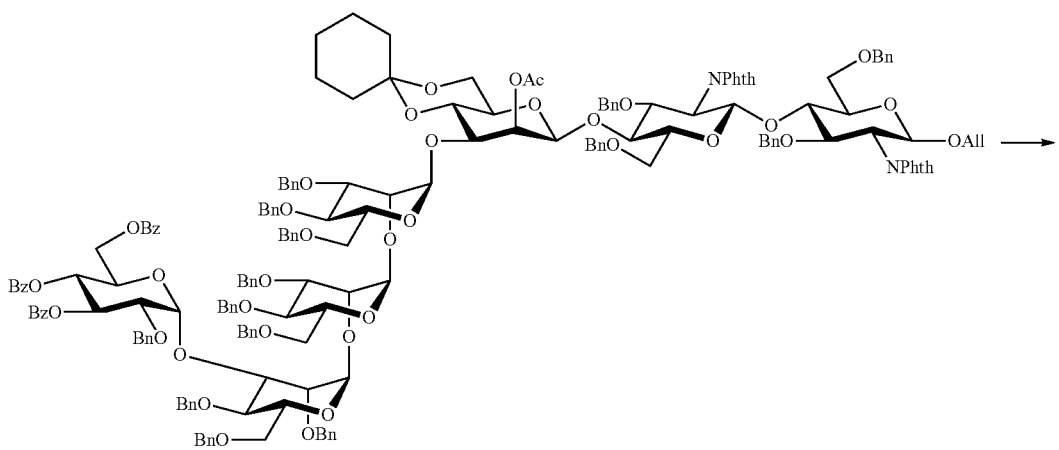

-continued

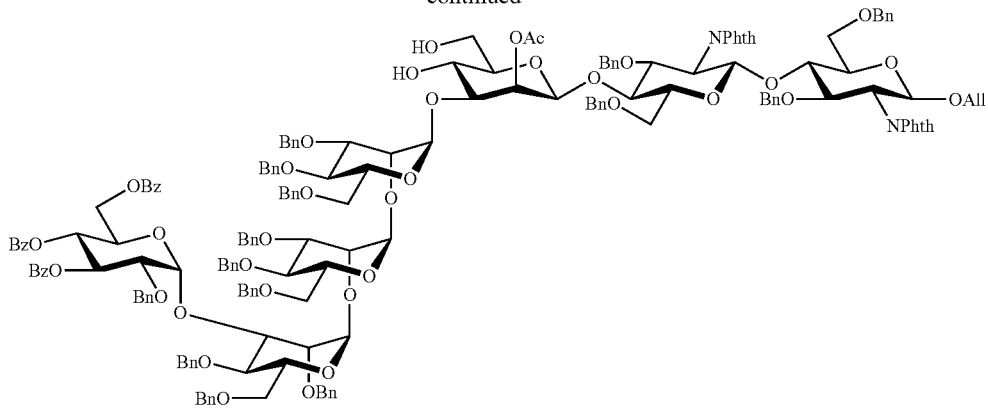

1.12. Coupling of Glucosyl Trimannosyl Core Trisaccharide Acceptor and GlcNAc-Mannobiosyl 1-6 (Galactosyl Mannobiose) 1-3 Mannose Donor To a stirred mixture of Cp$_2$HfCl$_2$ (22.7 mg, 0.060 mmol), AgOTf (36.8 mg, 0.143 mmol), and molecular sieves 4A (1.8 g) in dry toluene (5 mL) was added a solution of Glucosyl trimannosyl core trisaccharide acceptor (104.6 mg, 0.0323 mmol) and GlcNAc-mannobiosyl 1-6(galactosyl mannobiose) 1-3 mannose donor (93.3 g, 0.030 mmol) in dry toluene (10 mL) at −30° C. The mixture was gradually warmed up to 0° C. and stirred for 4 h. The reaction was quenched with TEA (1 mL). Insoluble materials were removed by passage through Celite and the filtrate was diluted with EtOAc and washed with brine, aq. NaHCO$_3$ and brine successively. The solution was dried over Na$_2$SO$_4$ and concentrated in vacuo. The residue was purified by PTLC (toluene:EtOAc, 5:1) to afford [GlcNAc-mannobiosyl 1-6(galactosyl mannobiose) 1-3 mannosyl] 1-6 Glucosyl trimannosyl core trisaccharide (42.7 mg, 23%).

$^1$H NMR (400 MHz, CDCl$_3$) δ 8.064-6.596 (m, 197H), 6.089 (t, 1H, J=9.6 Hz), 5.092 (d, 1H, J=3.2 Hz), 3.834 (dd, 1H, J=10.0 and 8.4 Hz), 5.611-5.466 (m, 3H), 5.339-5.142 (m, 9H), 4.985-3.164 (m, 155H), 3.051 (bd, 1H, J=10 Hz), 2.109 (s, 3H);

MALDI-TOF mass calcd for C$_{379}$H$_{371}$O$_{82}$N$_3$Na (M+Na)$^+$ 6298.5, found 6300.2.

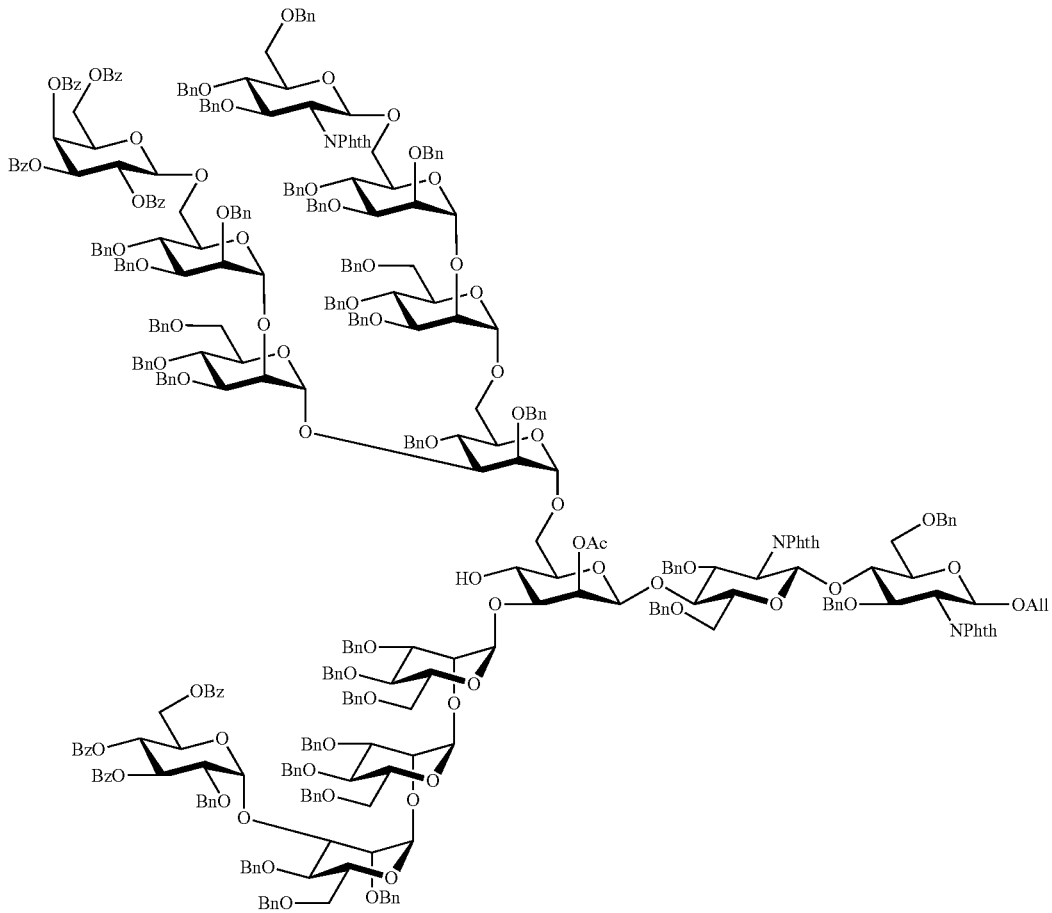

1.13. Deprotection of [GlcNAc-Mannobiosyl 1-6 (Galactosyl Mannobiose) 1-3 Mannosyl] 1-6 Glucosyl Trimannosyl Core Trisaccharide A solution of [GlcNAc-mannobiosyl 1-6(galactosyl mannobiose) 1-3 mannosyl] 1-6 Glucosyl trimannosyl core trisaccharide (42.7 mg, 0.0068 mmol) in n-butanol (2 mL) containing 1 mL of ethylenediamine was stirred at 90° C. for 15 h. Volatiles were removed by evaporation in vacuo and the residue was dissolved in pyridine (3 mL). The solution was treated with $Ac_2O$ (1.5 mL) at 0° C. for 5 h and evaporated in vacuo. The residue was diluted with EtOAc and washed with brine, 1 N HCl, brine, aq. $NaHCO_3$ and brine successively. The solution was dried over $Na_2SO_4$ and concentrated in vacuo to give acetylated compound. The acetylated compound was treated with $Pd(OH)_2$—C (20 wt. %, 50 mg) in MeOH (10 mL) at room temperature for 24 h. The mixture was filtered through Celite. The filtrate was concentrated in vacuo. The residue was purified using a Sep-Pak C18 cartridge (500 mg, Waters, $H_2O$:MeOH, 100:0-20:1) to give tetradecasaccharide TM (14 mg, 85%).

$^1$H NMR (400 MHz, $CDCl_3$) δ 5.185 (bs, 3H), 5.127 (d, 1H, J=3.6 Hz), 4.966 (bs, 1H), 4.934 (bs, 1H), 4.910 (bs, 1H), 4.898 (bs, 1H), 4.774 (bs, 1H), 4.266 (d, 1H, J=8.4 Hz), 4.464 (d, 1H, J=8.0 Hz), 4.374 (d, 1H, J=7.6 Hz), 4.309 (d, 1H, J=8.0 Hz), 4.109 (bs, 2H), 3.990-3.247 (m, H), 1.946 (s, 3H), 1.940 (s, 3H), 1.902 (s, 3H), 1.410 (m, 1H), 0.735 (t, 3H, J=7.6 Hz); MALDI-TOF mass calcd for $C_{93}H_{157}O_{71}N_3Na$ (M+Na)$^+$ 2474.9, found 2474.6.

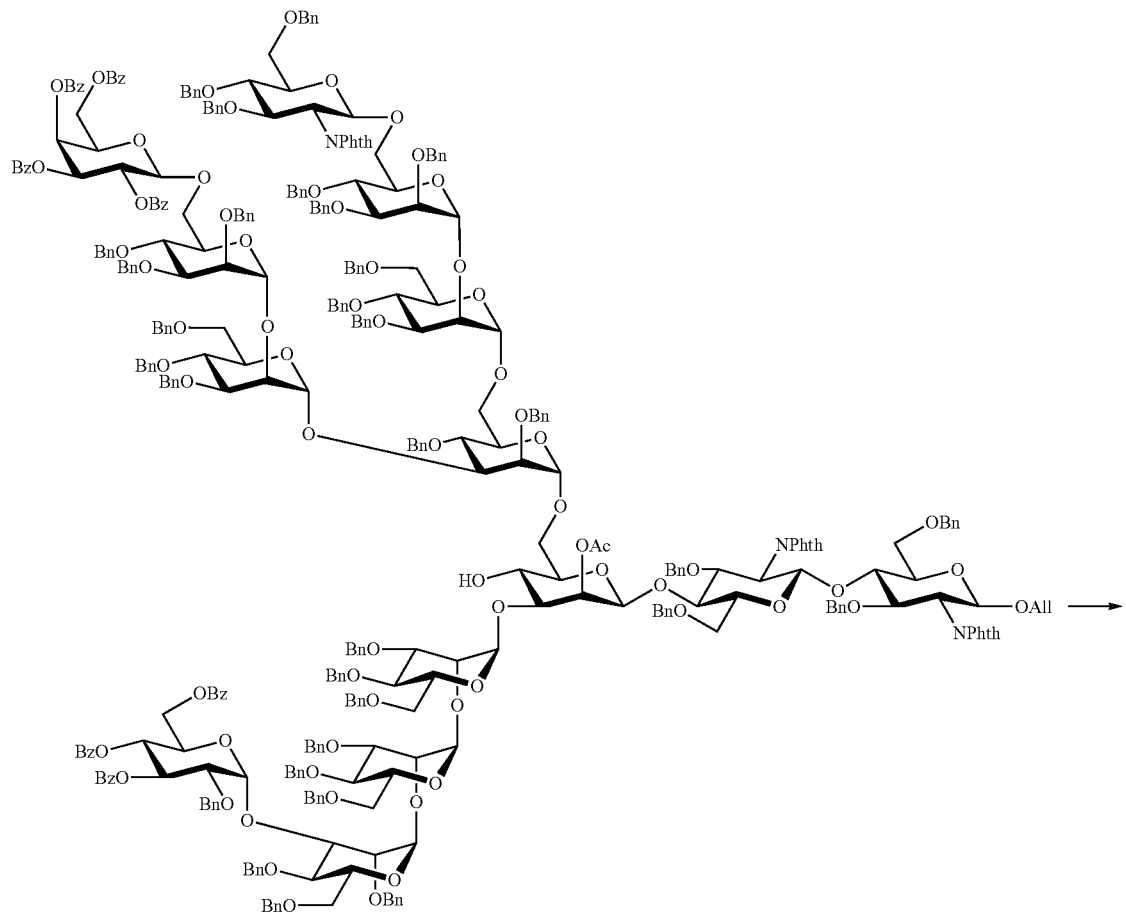

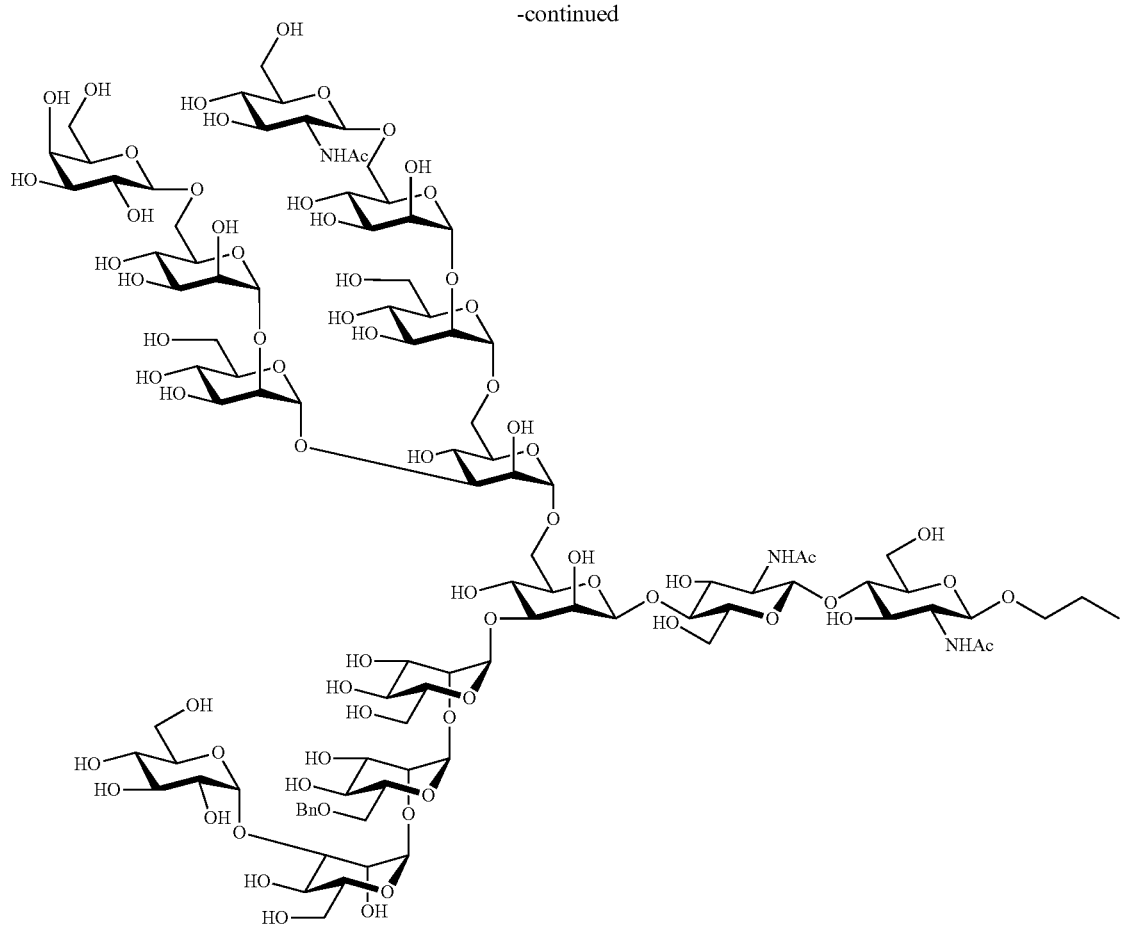

Production Example 2

Selective Cleavage of Terminal Sugar Residues Using Glycosidases

Figure 2:
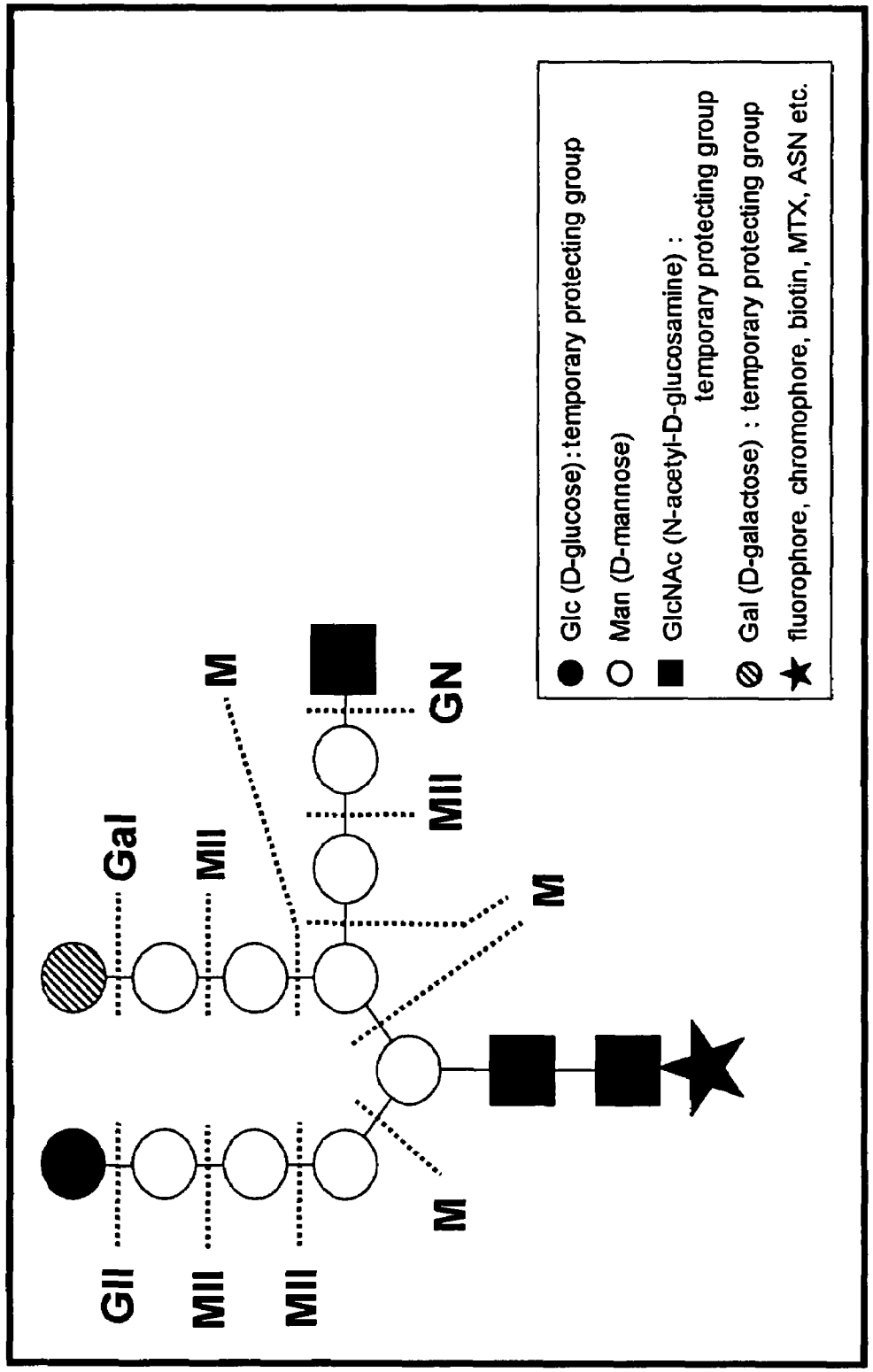
FIG. 2 shows a glycosidase cleavage site in a protected high mannose type sugar chain compound. The sugar residues at sugar chain termini are temporary protecting groups. GII: glucosidase II; Gal: β-galactosidase; GN: GlcNAcase; MII: α1-2 mannosidase; M: mannosidase

By preparing a starting sugar chain compound comprising all structures required for a sugar chain library, which incorporates independently removable protecting groups on the non-reducing terminus sides of sugar chains, it is possible to convert the starting sugar chain compound to a desired sugar chain compound with no dependence on the selectivity of glycosidases. For example, a sugar chain library can be constructed by strategically cleaving a high mannose type sugar chain (tetradecasaccharide) incorporating independently removable protecting groups on the non-reducing terminus sides of sugar chains, produced in 1.13 above, or a derivative thereof (e.g., the compound produced in 1.12 above), with glycosidases (FIG. 1). Because the high mannose type sugar chain compounds produced in 1.13 above (and 1.12) have the glycosidase cleavage sites shown in FIG. 2, the various sugar chains shown in Tables 1 to 4 below (but some compounds are overlapping) can be produced by reacting various glycosidases as appropriate.

TABLE 1

The compounds having the same structures as those of naturally occurring sugar chains generated from high mannose type sugar chain (GlcMan9GlcNAc2)

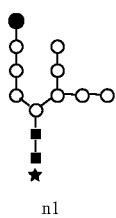

n1

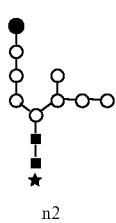

n2

TABLE 1-continued
The compounds having the same structures as those of naturally occurring sugar chains generated from high mannose type sugar chain (GlcMan9GlcNAc2)
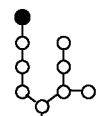
n3
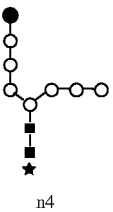
n4
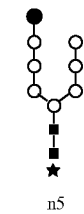
n5
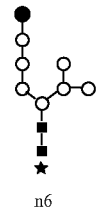
n6
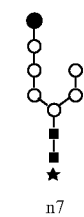
n7
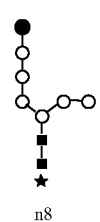
n8
TABLE 1-continued
The compounds having the same structures as those of naturally occurring sugar chains generated from high mannose type sugar chain (GlcMan9GlcNAc2)
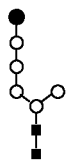
n9
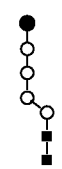
n10
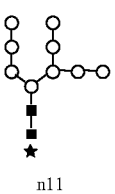
n11
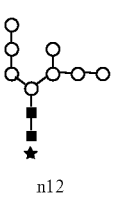
n12
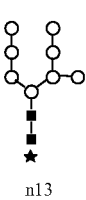
n13
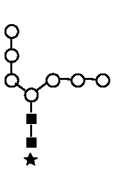
n14
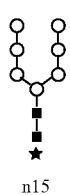
n15

TABLE 1-continued
The compounds having the same structures as those of naturally occurring sugar chains generated from high mannose type sugar chain (GlcMan9GlcNAc2)
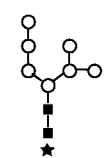
n16
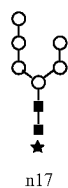
n17
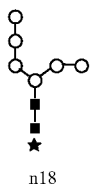
n18
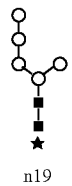
n19
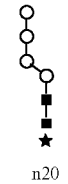
n20
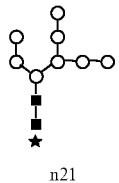
n21
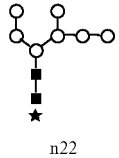
n22
TABLE 1-continued
The compounds having the same structures as those of naturally occurring sugar chains generated from high mannose type sugar chain (GlcMan9GlcNAc2)
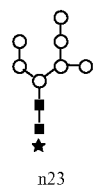
n23
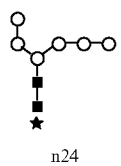
n24
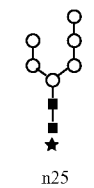
n25
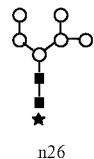
n26
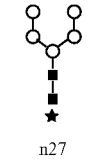
n27
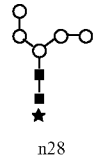
n28
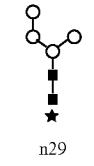
n29
n30

TABLE 1-continued
The compounds having the same structures as those of naturally occurring sugar chains generated from high mannose type sugar chain (GlcMan9GlcNAc2)
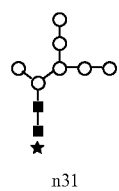
n31
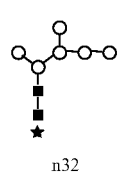
n32
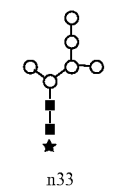
n33
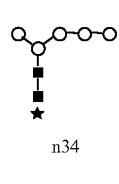
n34
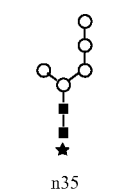
n35
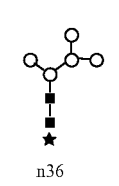
n36
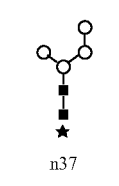
n37
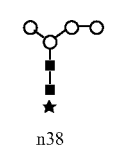
n38
TABLE 1-continued
The compounds having the same structures as those of naturally occurring sugar chains generated from high mannose type sugar chain (GlcMan9GlcNAc2)
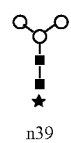
n39
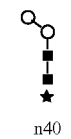
n40
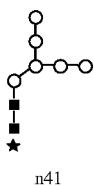
n41
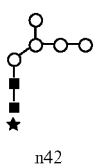
n42
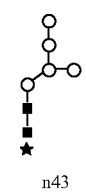
n43
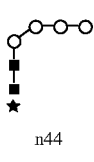
n44
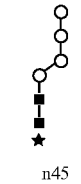
n45
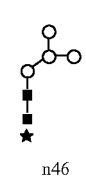
n46

TABLE 1-continued
The compounds having the same structures as those of naturally occurring sugar chains generated from high mannose type sugar chain (GlcMan9GlcNAc2)
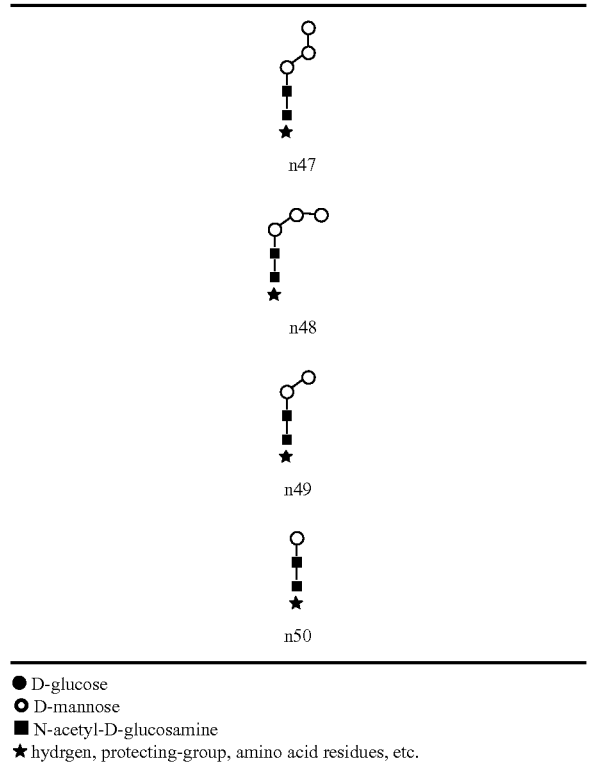
- ● D-glucose
- ○ D-mannose
- ■ N-acetyl-D-glucosamine
- ★ hydrgen, protecting-group, amino acid residues, etc.
TABLE 2
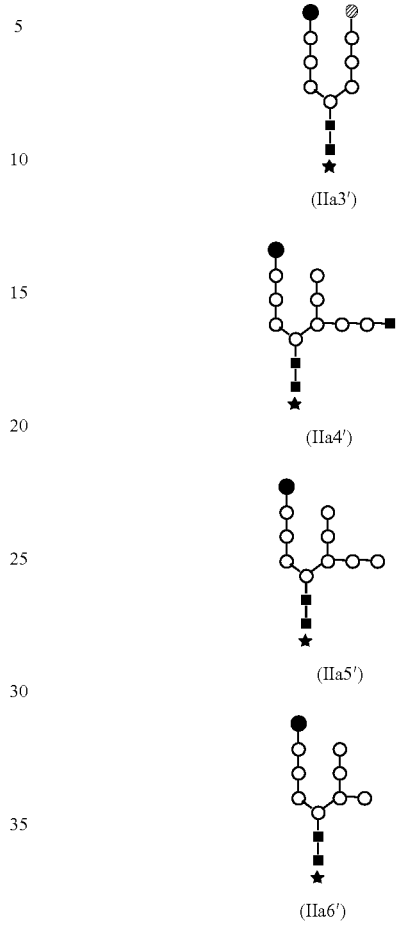
TABLE 2-continued
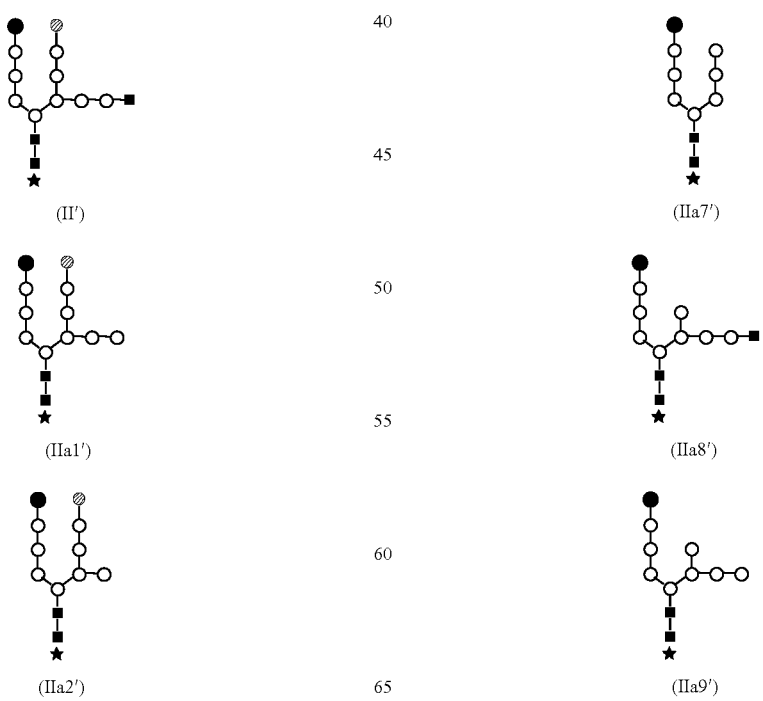

TABLE 2-continued
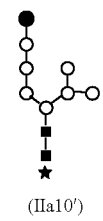
(IIa10′)
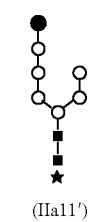
(IIa11′)
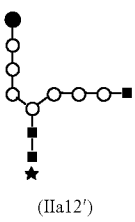
(IIa12′)
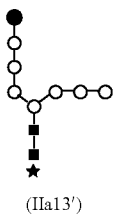
(IIa13′)
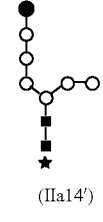
(IIa14′)
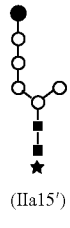
(IIa15′)
TABLE 2-continued
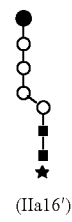
(IIa16′)
- ● D-glucose
- ○ D-mannose
- ■ N-acetyl-D-glucosamine
- ◉ D-galactose
- ★ hydrogen, protecting group, amino acid residues, etc.
TABLE 3
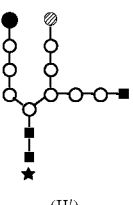
(II′)
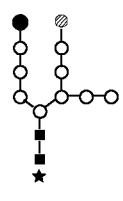
(IIb1′)
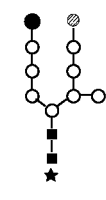
(IIb2′)
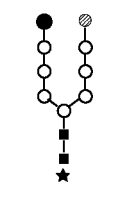
(IIb3′)
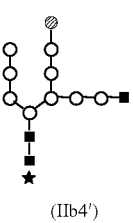
(IIb4′)

TABLE 3-continued (IIb5′)

(IIb6′)

(IIb7′)

(IIb8′)

(IIb9′)

(IIb10′)

(IIb11′)

TABLE 3-continued (IIb12′)

(IIb13′)

(IIb14′)

(IIb15′)

(IIb16′)

(IIb17′)

(IIb18′)

TABLE 3-continued (IIb19′)

- ● D-glucose
- ○ D-mannose
- ■ N-acetyl-D-glucosamine
- ⊘ D-galactose
- ★ hydrogen, protecting-group, amino acid residues, etc.

TABLE 4

(II′)

(IIc1′)

(IIc2′)

(IIc3′)

(IIc4′)

TABLE 4-continued (IIc5′)

(IIc6′)

(IIc7′)

(IIc8′)

(IIc9′)

(IIc10′)

(IIc11′)

(IIc12′)

TABLE 4-continued

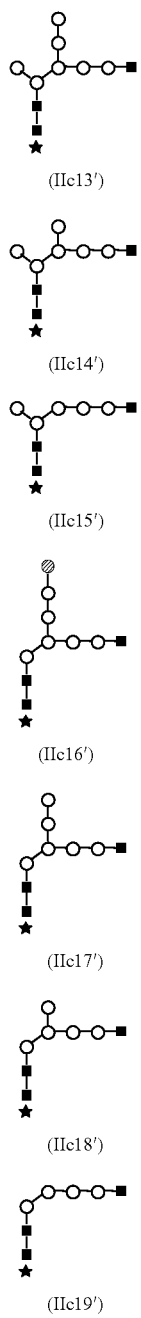

(IIc13')
(IIc14')
(IIc15')
(IIc16')
(IIc17')
(IIc18')
(IIc19')

● D-glucose
○ D-mannose
■ N-acetyl-D-glucosamine
◉ D-galactose
★ hydrogen, protecting group, amino acid residues, etc.

Hence, the present inventors investigated to determine whether or not the protecting groups (sugar residues) introduced to the non-reducing termini of the high mannose type sugar chain produced in 1.13 above can actually be removed independently.

Figure 3:
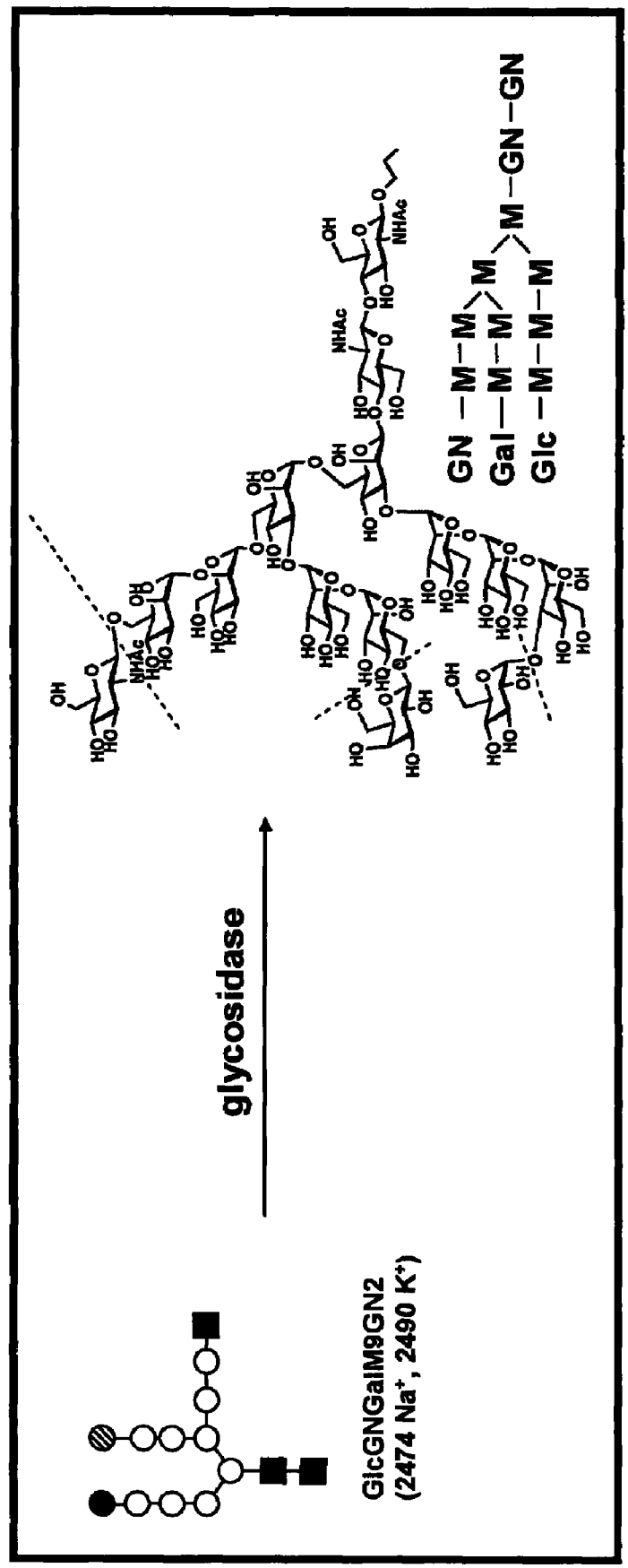
FIG. 3 shows an outline of the selective cleavage of sugar residues at sugar chain termini in a protected high mannose type sugar chain by glucosidase II, galactosidase or GlcNAcase.

A 100 μL of reaction mixture (tetradecasaccharide; 1 mg, any enzyme of GlcNAc'ase from Jack beans (5 U), galactosidase from *A. oryzae* (50 U) and glucosidase II from *A. oryzae* (200 μL of *A. oryzae* membrane fraction), DMNM (deoxymannonojirimycin), 40 mM acetate buffer (pH 4.5)) was incubated at 37° C. for certain days. The reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) (FIGS. 3 and 4).

Figure 4:
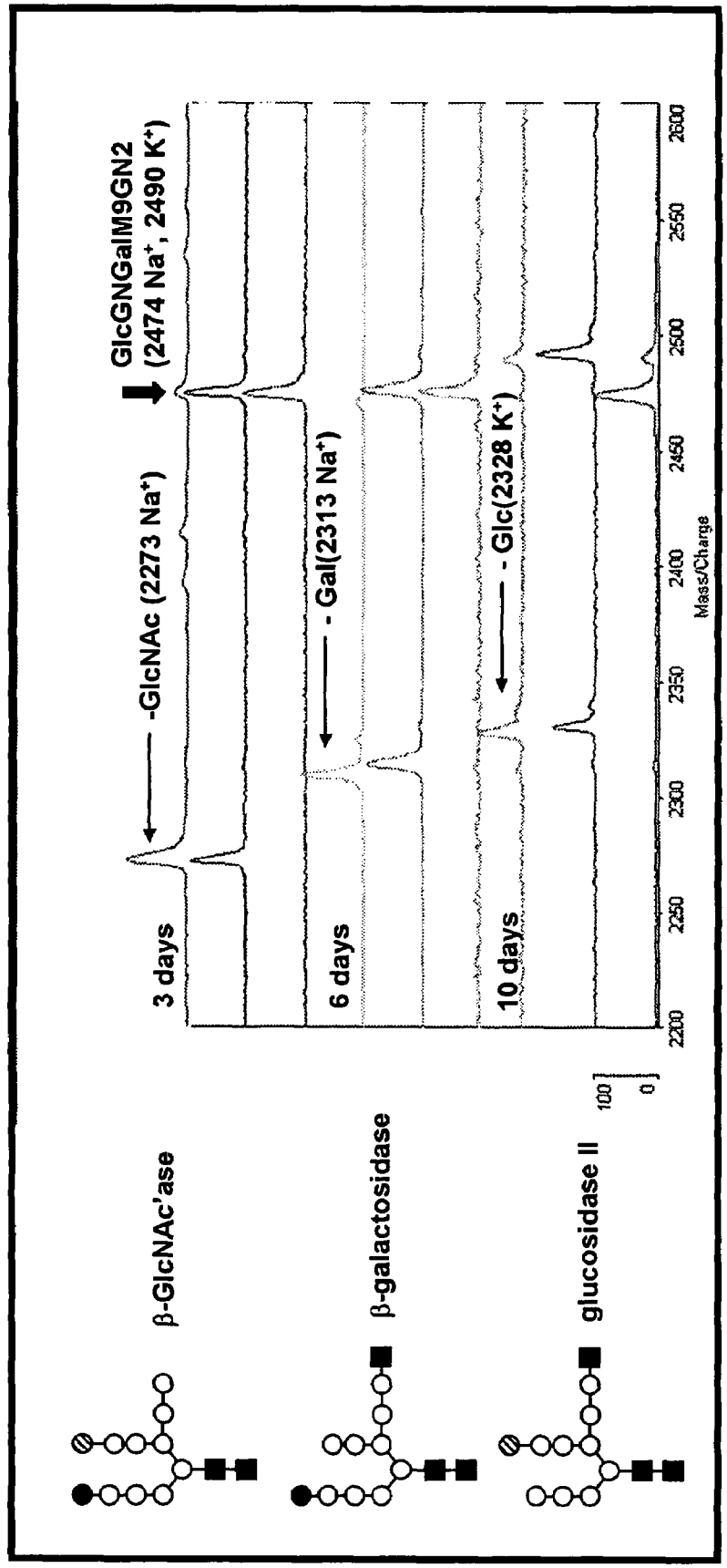
FIG. 4 shows the confirmation by MALDI TOF MS of the selective cleavage of sugar residues at sugar chain termini in a protected high mannose type sugar chain compound.

As a result, production of a sugar chain compound deprived of D-glucose from the non-reducing termini of the high mannose type sugar chain (tetradecasaccharide) (a compound represented by the formula (IIb4') above), production of a sugar chain compound deprived of D-galactose from the non-reducing termini of the high mannose type sugar chain (a compound represented by the formula (IIa4') above), and production of a sugar chain compound deprived of N-acetyl-D-glucosamine from the non-reducing termini of the high mannose type sugar chain (a compound represented by the formula (IIa1') above) were confirmed (FIG. 4).

Sugar chain compound deprived of D-glucose
$C_{87}H_{147}N_3O_{66}K_1$ Calcd for 2328.8, Found 2328.4
Sugar chain compound deprived of D-galactose
$C_{87}H_{147}N_3O_{66}Na_1$ Calcd for 2312.8, Found 2313.5
Sugar chain compound deprived of N-acetyl-D-glucosamine
$C_{85}H_{144}N_2O_{66}Na_1$ Calcd for 2271.8, Found 2271.7

Production Example 3

Preparation of GM9 (the Compound Represented by the Formula (IIa5') Described Above)

A 100 μL of reaction mixture (tetradecasaccharide; 1 mg, GlcNAc'ase from Jack beans (0.3 U), galactosidase from *A. oryzae* (30 U), 1 μL of 10 mM DMNM, and 40 mM acetate buffer (pH 4.5)) was incubated at 37° C. for 10 days. The reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM9 (1 mg, quant.).

GM9 (the compound represented by the formula (IIa5') described above)

The NMR and MS values of this compound agreed with those of the compound described in Matsuo et al., J. Am. Chem. Soc. 125: 3402 (2003).

Production Example 4

Preparation of GM8B (the Compound Represented by the Formula (IIa9') Described Above)

Figure 5:
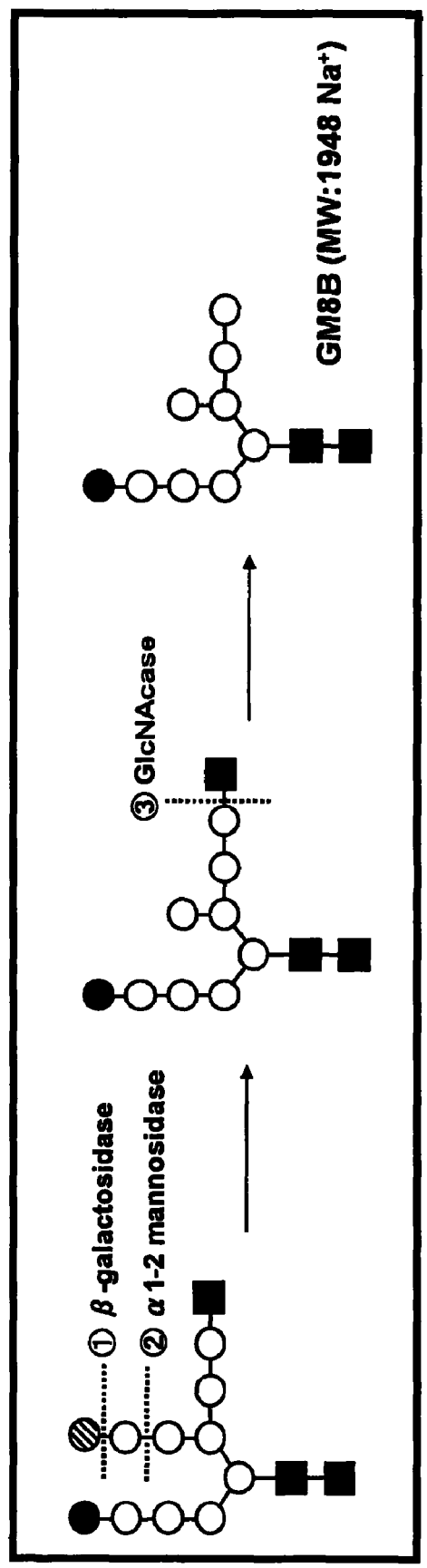
FIG. 5 shows an outline of GM8B production using galactosidase, α1-2 mannosidase and GlcNAcase.

A 100 μL of reaction mixture (tetradecasaccharide; 1 mg, galactosidase from *A. oryzae* (50 U), and 40 mM acetate buffer (pH 4.5)) was incubated at 37° C. for 7 days. The mixture was added α1-2 mannosidase (*A. saitoi*, 0.003 U) and incubated for 12 h, then GlcNAc'ase (Jack beans, 0.3 U) and 1 μL of 10 mM DMN (deoxynojirimycin) was added. The reaction mixture was incubated for 12 h. The reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM8B (1 mg, quant.) (FIGS. 5-7).

GM8B (the compound represented by the formula (IIa9') described above)

The NMR and MS values of this compound agreed with those of the compound described in Matsuo et al., Carbohydr. Res. 338: 2163 (2003).

Figure 6:
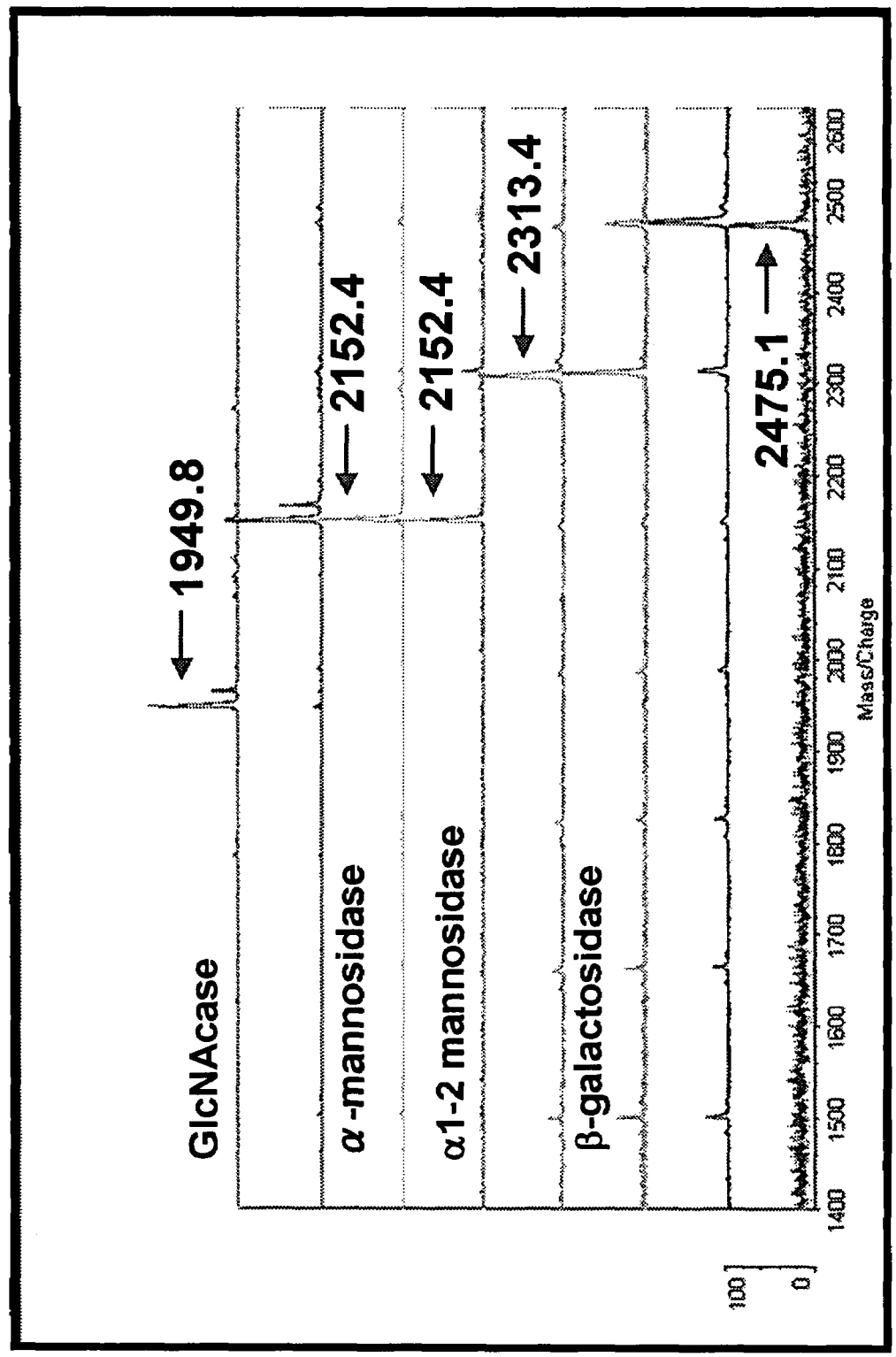
FIG. 6 shows the identification by MALDI TOF MS of GM8B produced by the selective cleavage of a protected high mannose type sugar chain compound, and an intermediate thereof.
Figure 7:
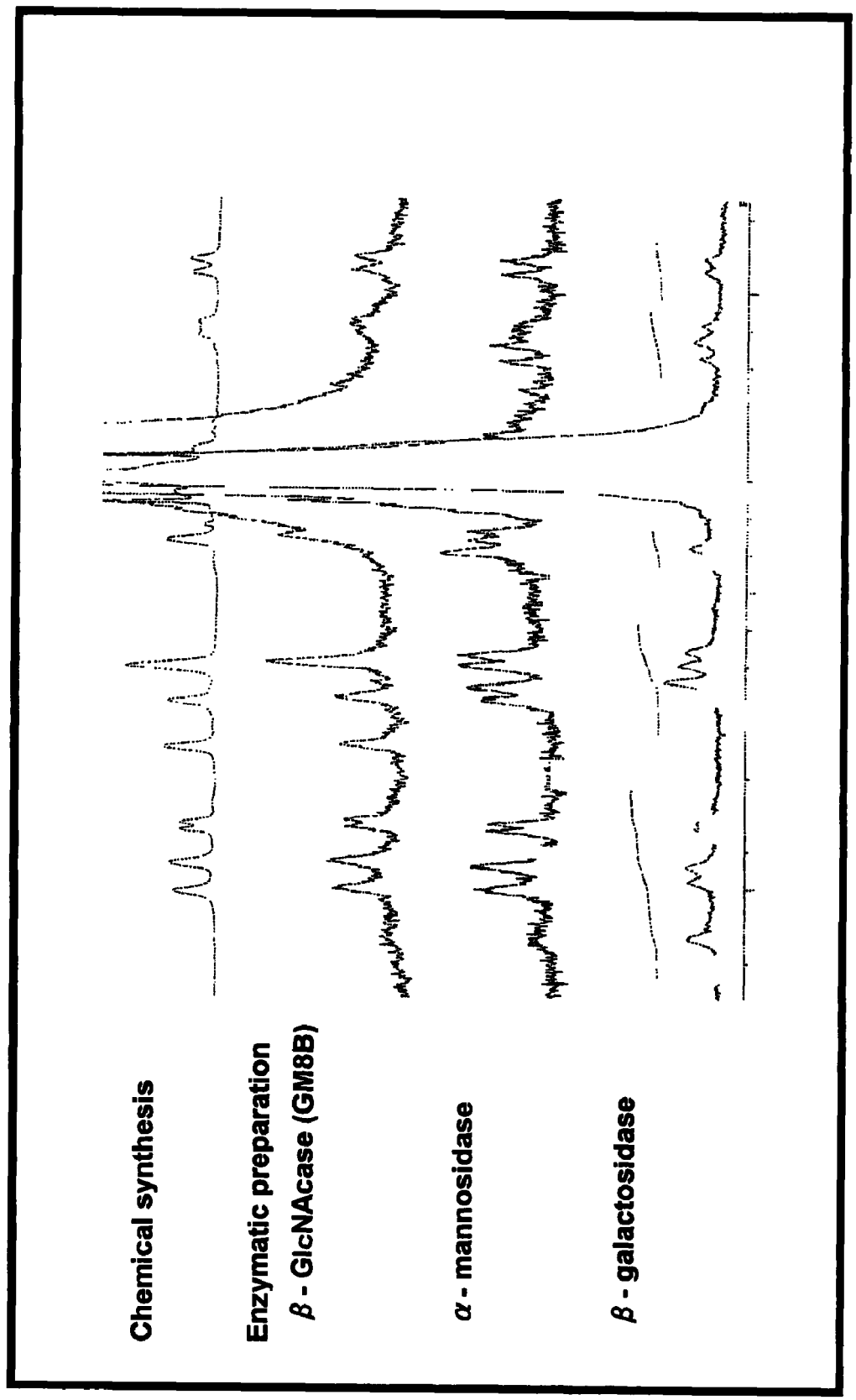
FIG. 7 shows the identification by NMR of GM8B produced by the selective cleavage of a protected high mannose type sugar chain compound, and an intermediate thereof. For information about the chemically synthesized GM8B used as the standard sample, see, for example, Matsuo et al., Carbohydr. Res. 338: 2163 (2003).

Production of compounds represented by the formulas (IIa4') and (IIa8') above, as intermediates for the preparation of GM8B, was also confirmed (FIGS. 6 and 7).

Compound represented by the formula (IIa8') above $C_{81}H_{137}N_3O_{61}Na_1$ Calcd for 2150.8, Found 2151.5

Production Example 5

Preparation of GM8C (the Compound Represented by the Formula (IIa6') Described Above)

A 100 μL of reaction mixture (tetradecasaccharide; 1 mg, GlcNAc'ase from Jack beans (0.3 U), α1-2 mannosidase from *A. saitoi* (0.001 U), 40 mM acetate buffer (pH 4.5)) was incubated at 37° C. for 24 h. The mixture was added galactosidase from *A. oryzae* (30 U) and DMNM. The reaction mixture was incubated for 10 days, then the reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM8C (1 mg, quant.).

GM8C (compound represented by the formula (IIa6') described above)

$C_{73}H_{124}N_2O_{56}Na_1$ Calcd for 1947.7, Found 1948.9

Production of compounds represented by the formula (IIa1') and (IIa2') above, as intermediates for the preparation of GM8C, were also identified.

Compound represented by the formula (IIa2') above $C_{79}H_{134}N_2O_{61}Na_1$ Calcd for 2109.7, Found 2109.9

Production Example 6

Preparation of GM7 (the Compound Represented by the Formula (IIa10') Described Above)

Figure 8:
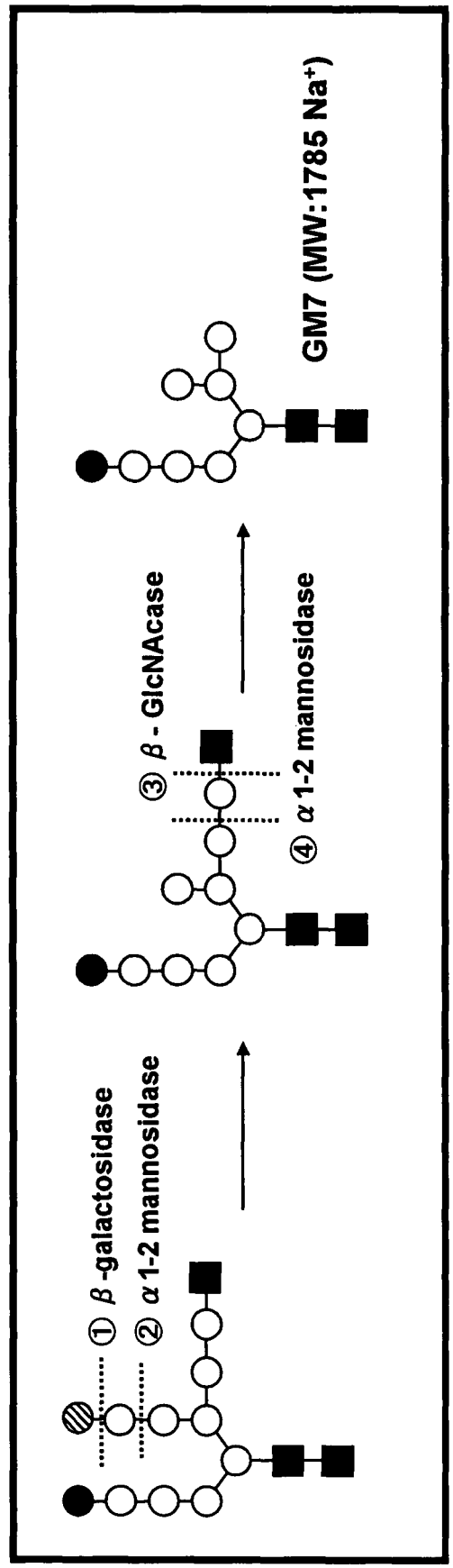
FIG. 8 shows an outline of GM7 production using galactosidase, α1-2 mannosidase and GlcNAcase.

A 100 μL of reaction mixture (tetradecasaccharide; 1 mg, galactosidase from *A. oryzae* (3 mg), α-mannosidase from Jack beans (5 μL), and 40 mM acetate buffer (pH 4.5)) was incubated at 37° C. for 7 min. The mixture was added GlcNAc'ase from Jack beans (0.3 U) and α1-2 mannosidase from *A. saitoi* (0.001 U) and incubated for 24 h. The reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM7 (FIGS. 8-10).

GM7 (compound represented by the formula (IIa10') described above)

$C_{67}H_{114}N_2O_{51}Na_1$ Calcd for 1785.6, Found 1787.2

Figure 9:
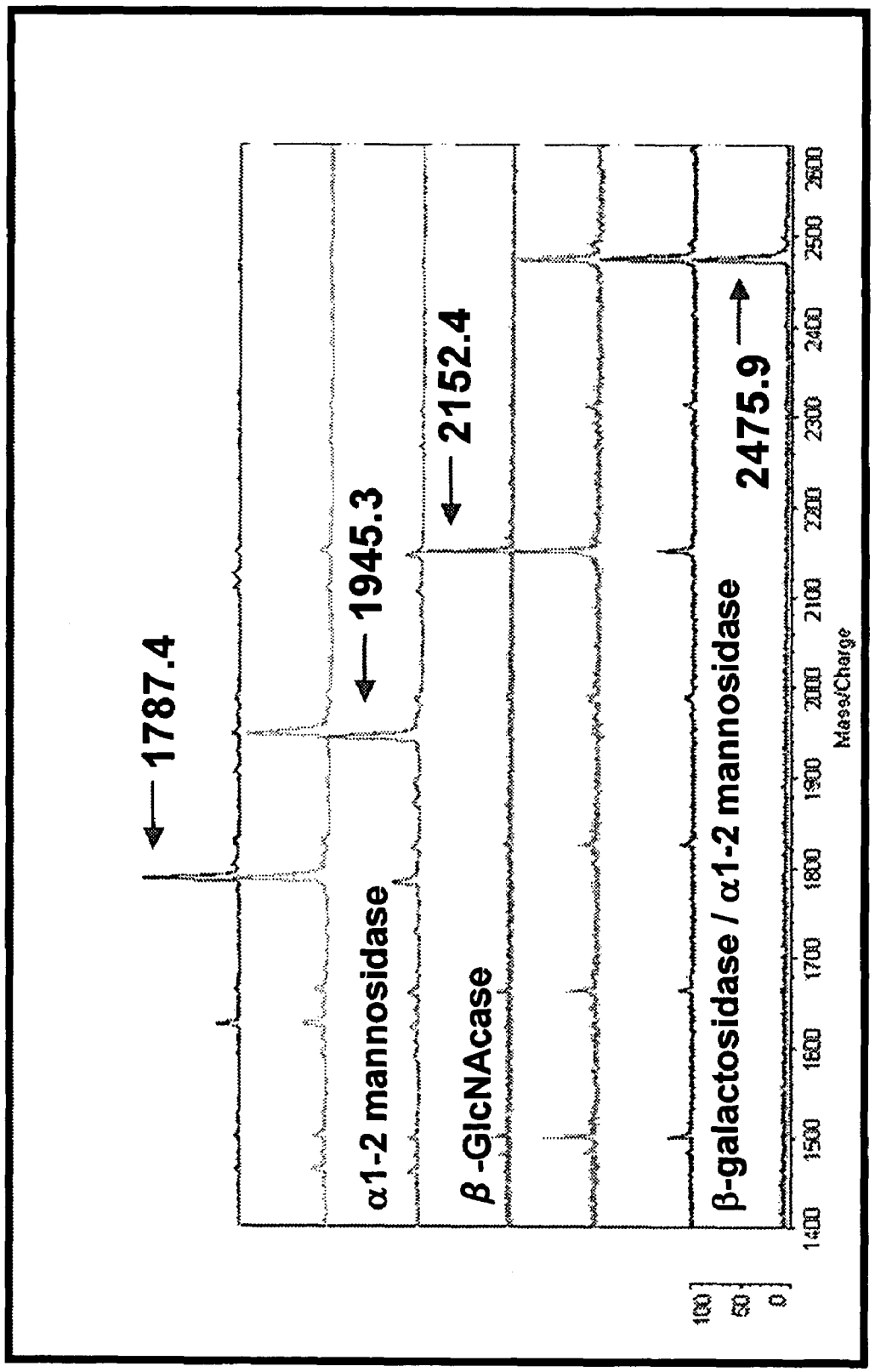
FIG. 9 shows the identification by MALDI TOF MS of GM7 produced by the selective cleavage of a protected high mannose type sugar chain compound, and an intermediate thereof.
Figure 10:
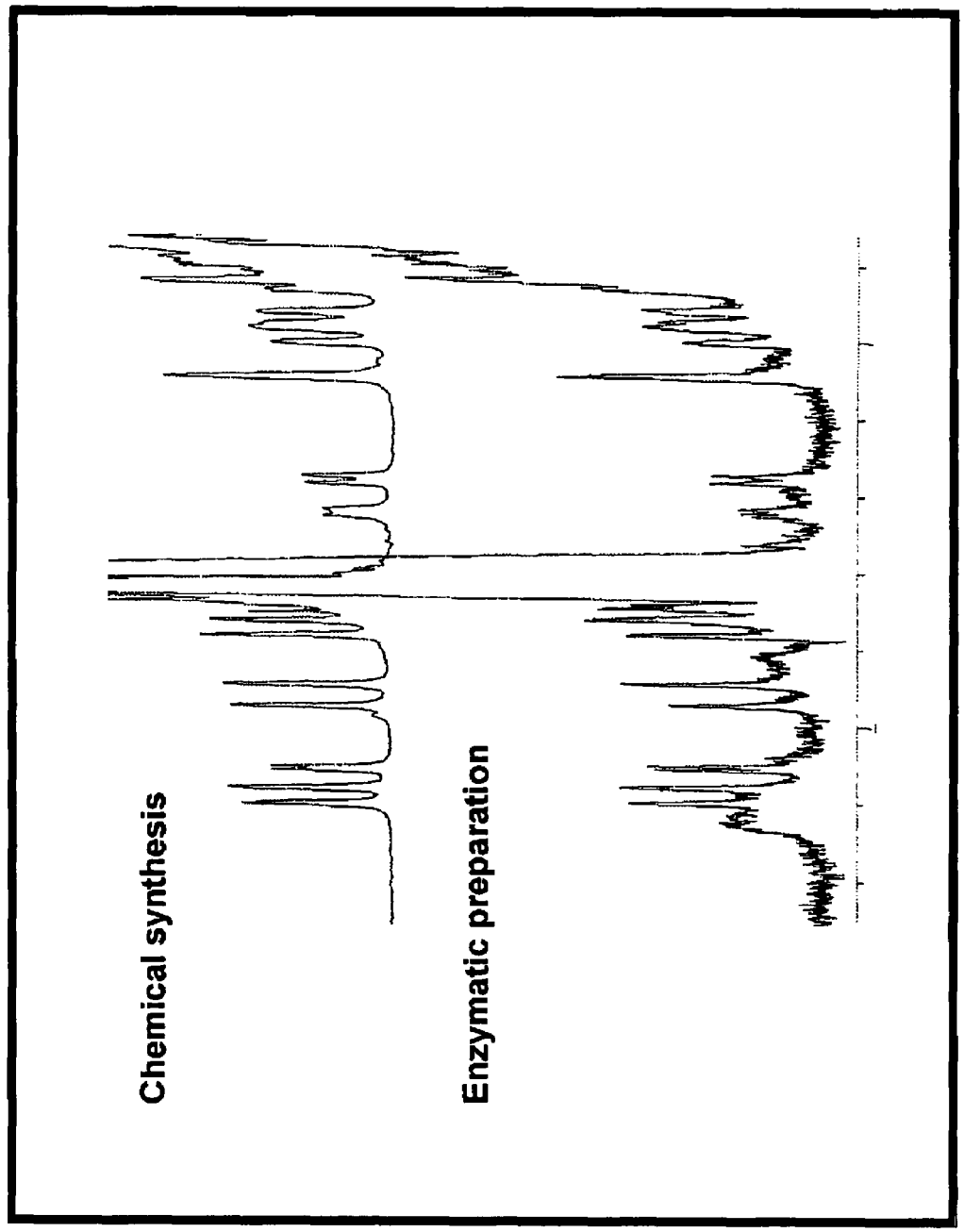
FIG. 10 shows the identification by NMR of GM7 produced by the selective cleavage of a protected high mannose type sugar chain compound. The synthetic GM7 used as the standard sample was chemically synthesized internally.

Production of compounds represented by the formulas (IIa4'), (IIa8') and (IIa9') above, as intermediates for the preparation of GM7, was also confirmed (FIG. 9).

Production Example 7

Preparation of GM7C (the Compound Represented by the Formula (IIa7') Described Above)

Figure 11:
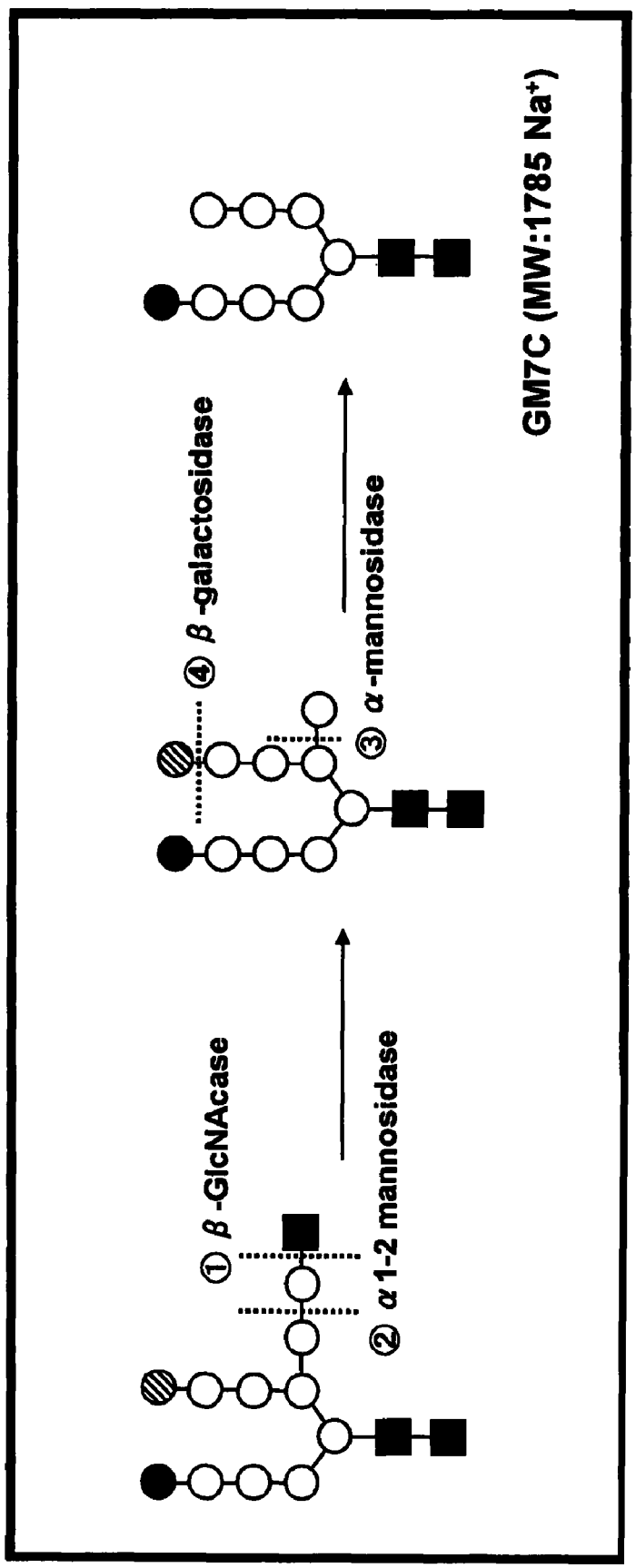
FIG. 11 shows an outline of GM7C production using galactosidase, α1-2 mannosidase, mannosidase and GlcNAcase.

A 100 μL of reaction mixture (tetradecasaccharide; 1 mg, GlcNAc'ase from Jack beans (0.3 U), α-mannosidase from Jack beans (0.5 U), and 40 mM acetate buffer (pH 4.5)) was incubated at 37° C. for 12 hours. The mixture was added galactosidase from *A. oryzae* (30 U) and incubated for 26 days, then the reaction was quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM7C (FIGS. 11 and 12).

GM7C (the compound represented by the formula (IIa7') described above)

$C_{67}H_{114}N_2O_{51}Na_1$ Calcd for 1785.6, Found 1787.2

Figure 12:
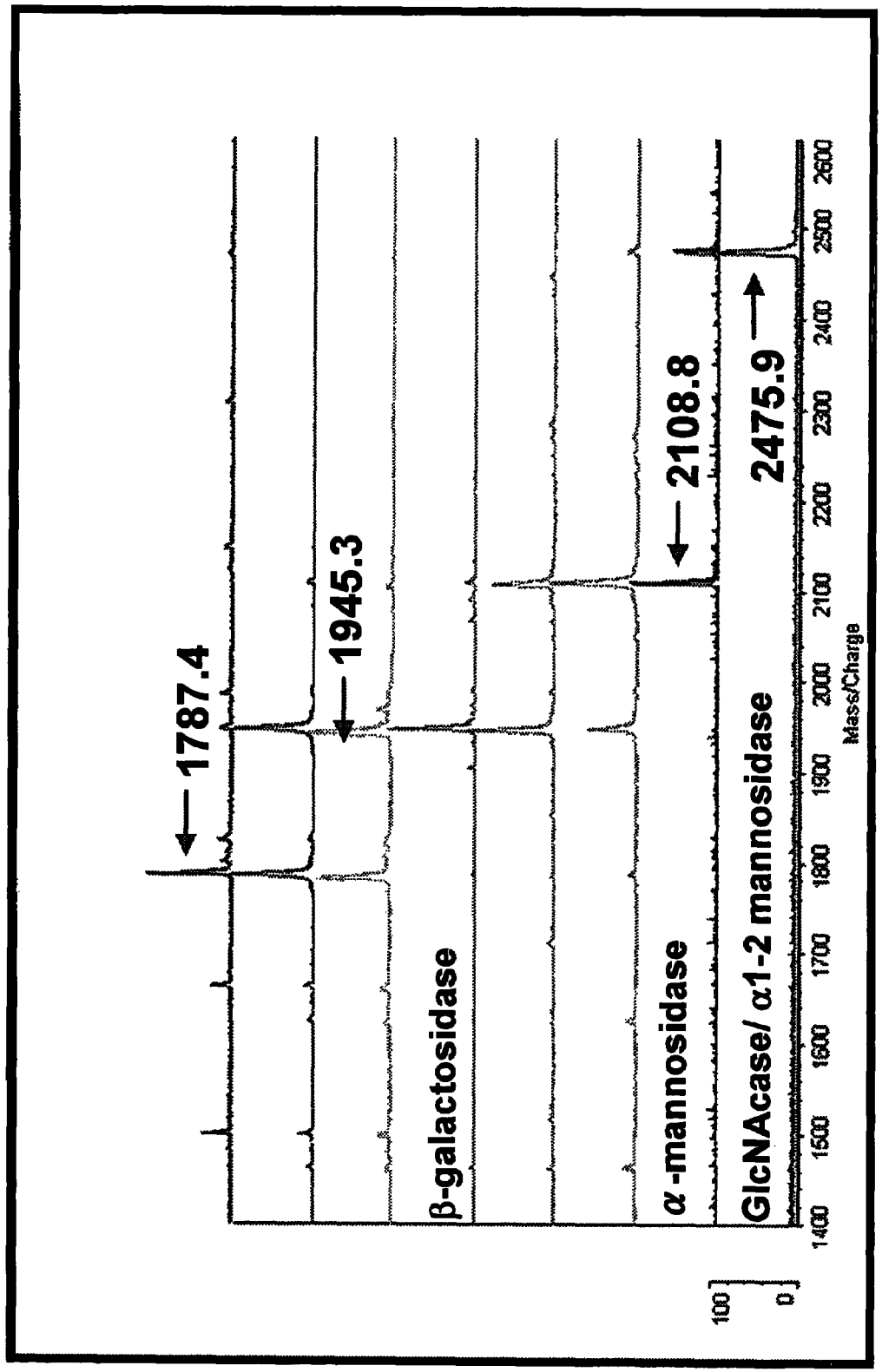
FIG. 12 shows the identification by MALDI TOF MS of GM7C produced by the selective cleavage of a protected high mannose type sugar chain compound, and an intermediate thereof.

Compounds represented by the formulas (IIa1'), (IIa2') and (IIa3') above, as intermediates for the preparation of GM7C, was also confirmed (FIG. 12).

Compound represented by the formula (IIa3')

$C_{73}H_{124}N_2O_{56}Na_1$ Calcd for 1947.7, Found 1945.3

Production Example 8

Preparation of M6C

Figure 13:
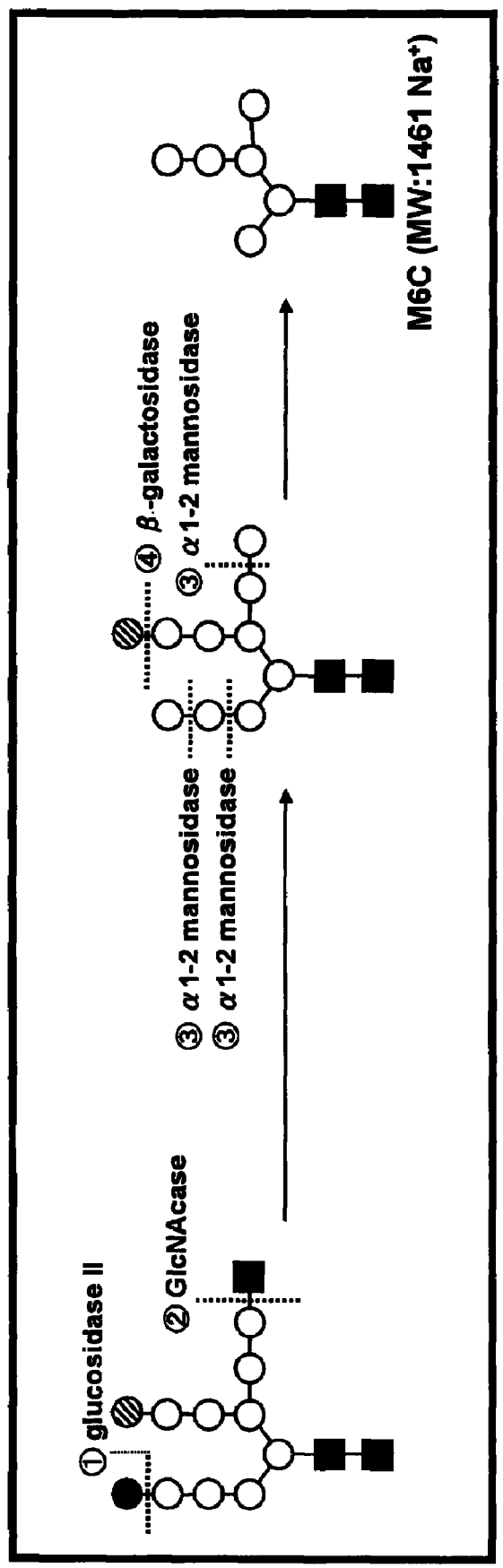
FIG. 13 shows an outline of M6C production using glucosidase II, GlcNAcase, galactosidase, α1-2 mannosidase, and galactosidase.

A 600 μL of reaction mixture (tetradecasaccharide; 1 mg, GlcNAc'ase from Jack beans (0.6 U), 500 μL of glucosidase II from *A. oryzae* (membrane fraction), 40 mM acetate buffer (pH 4.5)) was incubated at 37° C. for 12 hours. The mixture was added α1-2 mannosidase from *A. saitoi* (0.001 U), and incubated for 24 hours. The mixture was added galactosidase from *A. oryzae* (30 U), and incubated for 4 days, and the reaction was then quenched by heating at 100° C. for 1 min. The insoluble materials were filtrated by ultra-free (Millipore) and the filtrate was purified by Sep-Pak Cartridge (Waters, H$_2$O:MeOH, 100:0-70:30) to give GM6C (FIGS. 13 and 14).

GM6C $C_{55}H_{94}N_2O_{41}Na_1$ Calcd for 1461.5, Found 1463.4

Figure 14:
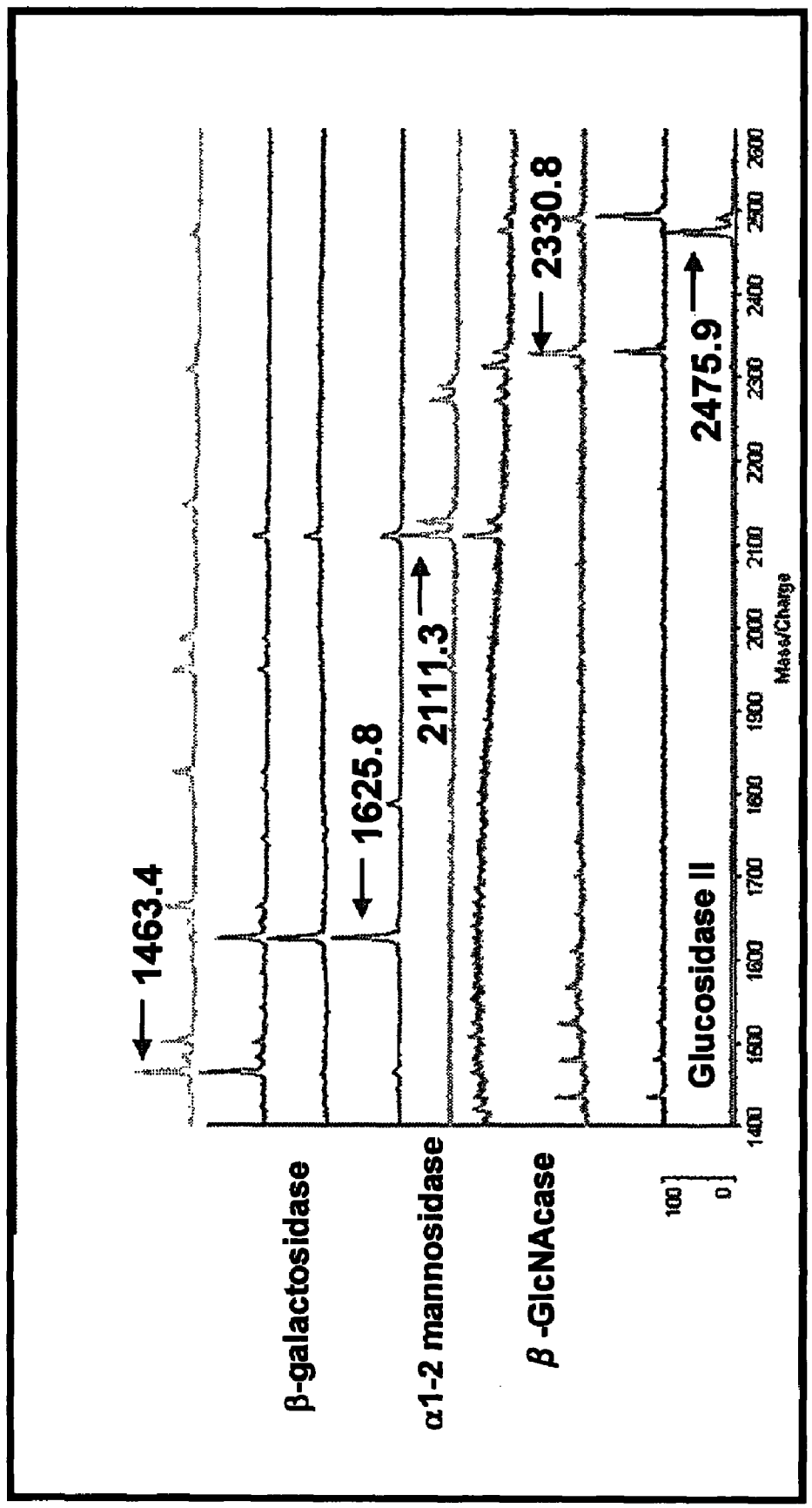
FIG. 14 shows the identification by MALDI TOF MS of M6C produced by the selective cleavage of a protected high mannose type sugar chain compound, and an intermediate thereof.

Production of compounds represented by the formulas (IIb4'), (IIb5') and (IIb14') above, as intermediates for the preparation of M6C, was also confirmed (FIG. 14).

Compound represented by the formula (IIb5') above $C_{79}H_{134}N_2O_{61}Na_1$ Calcd for 2109.7, Found 2111.3

Compound represented by the formula (IIb14') above $C_{61}H_{104}N_2O_{46}Na_1$ Calcd for 1623.6, Found 1625.8

Production Example 9

Preparation of Other Sugar Chain Compounds Having the Same Structure as that of Naturally Occurring Sugar Chain Generated from a High Mannose Type Sugar Chain By using glucosidase II, galactosidase, GlcNAc'ase, α-mannosidase and α1-2 mannosidase in the combinations shown in Table 5 below under the appropriate reaction conditions for the respective enzymes (e.g., the reaction conditions used in preparing the above-described sugar chain compounds), sugar chain compounds having the same structure as that of naturally occurring sugar chain generated from a high mannose type sugar chain (see, e.g., Table 1) are prepared.

TABLE 5
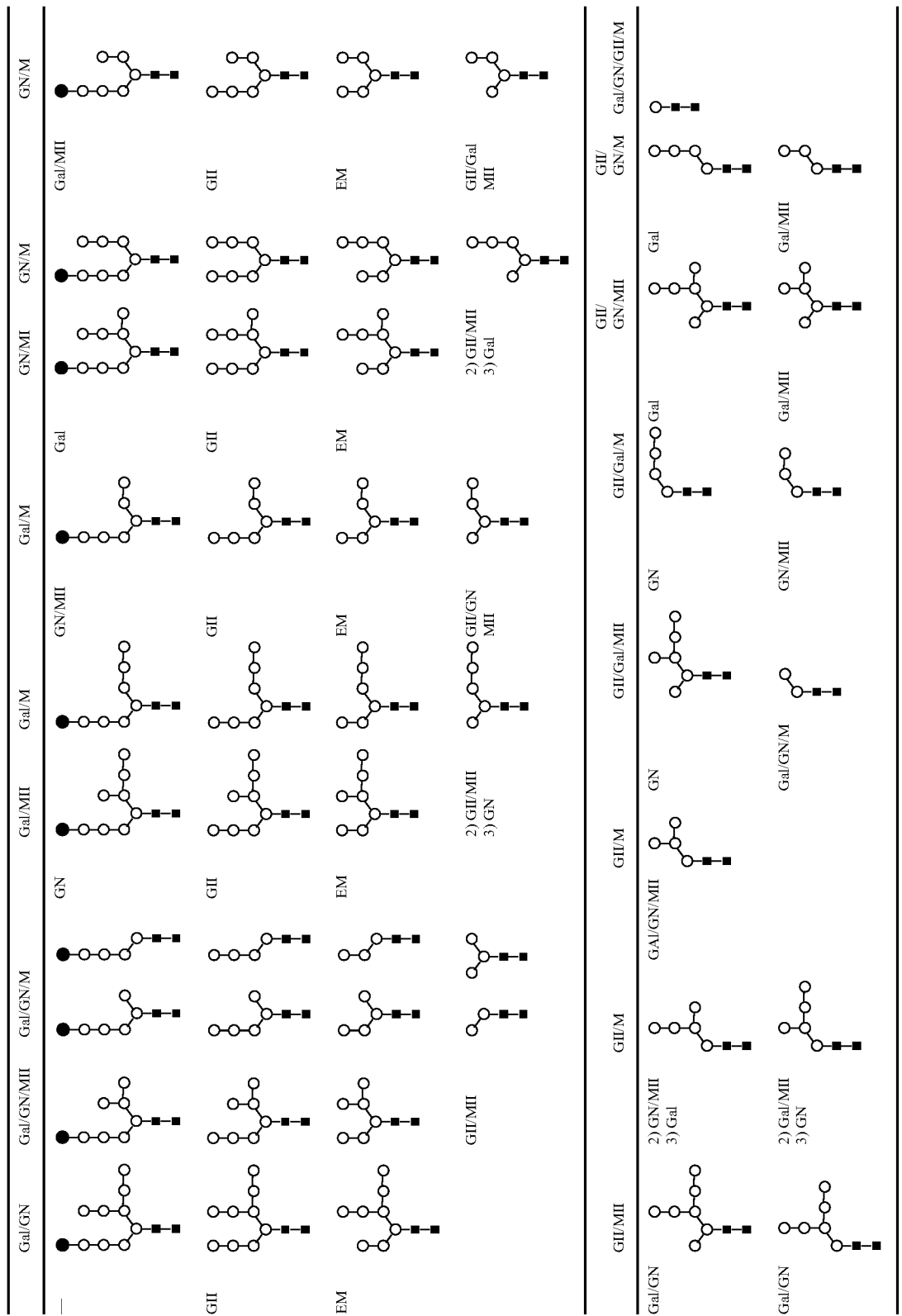

The abbreviations for the enzymes used herein are as follows:

Gal: β-galactosidase; MII: α1-2 mannosidase; M: mannosidase; GN: glucosidase II; EM: endomannosidase Production Example 10

Figure 15:
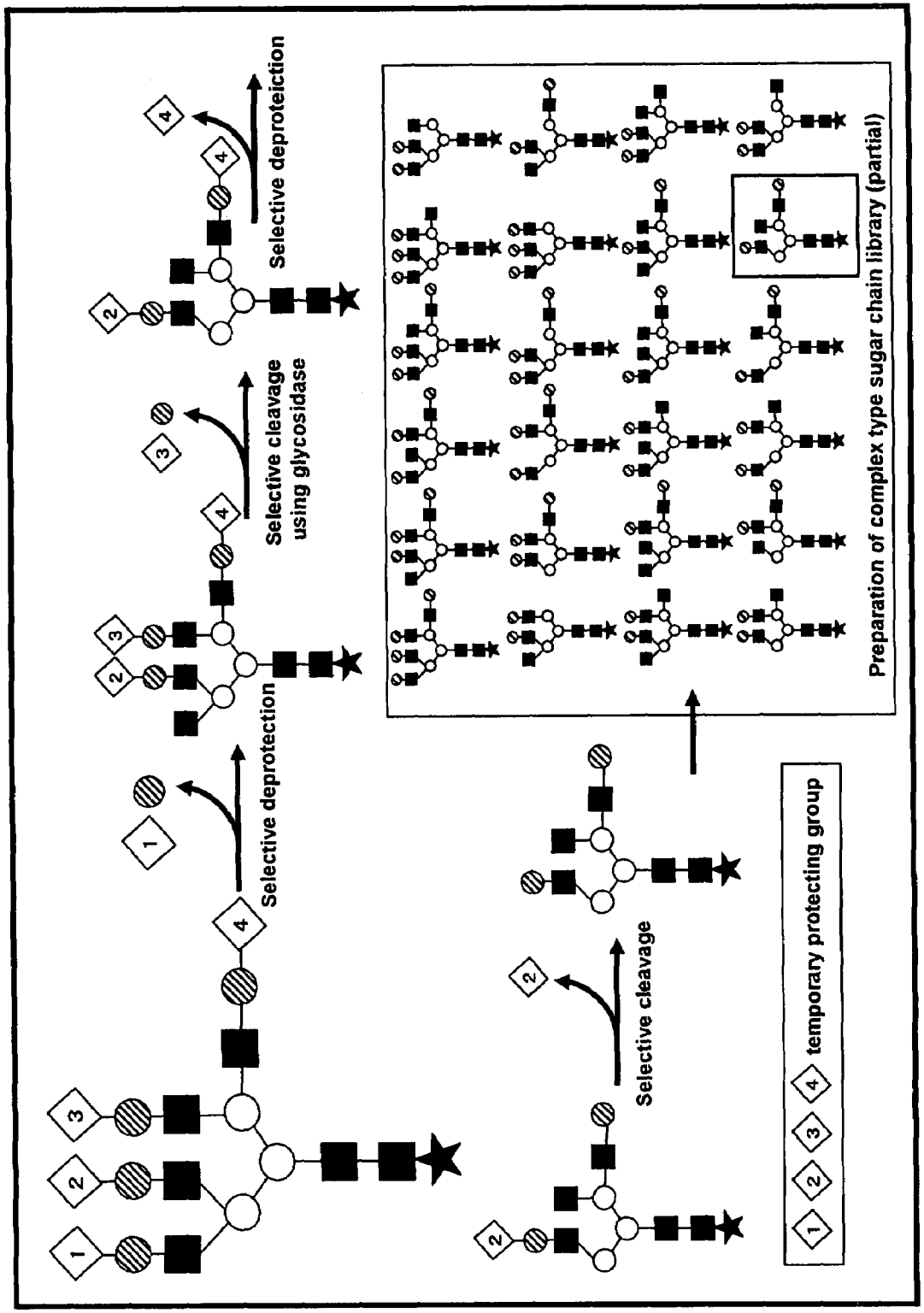
FIG. 15 shows an outline of the construction of various sugar chain compounds from a protected complex type sugar chain compound. The sugar residues at sugar chain termini are temporary protecting groups.
Figure 17:
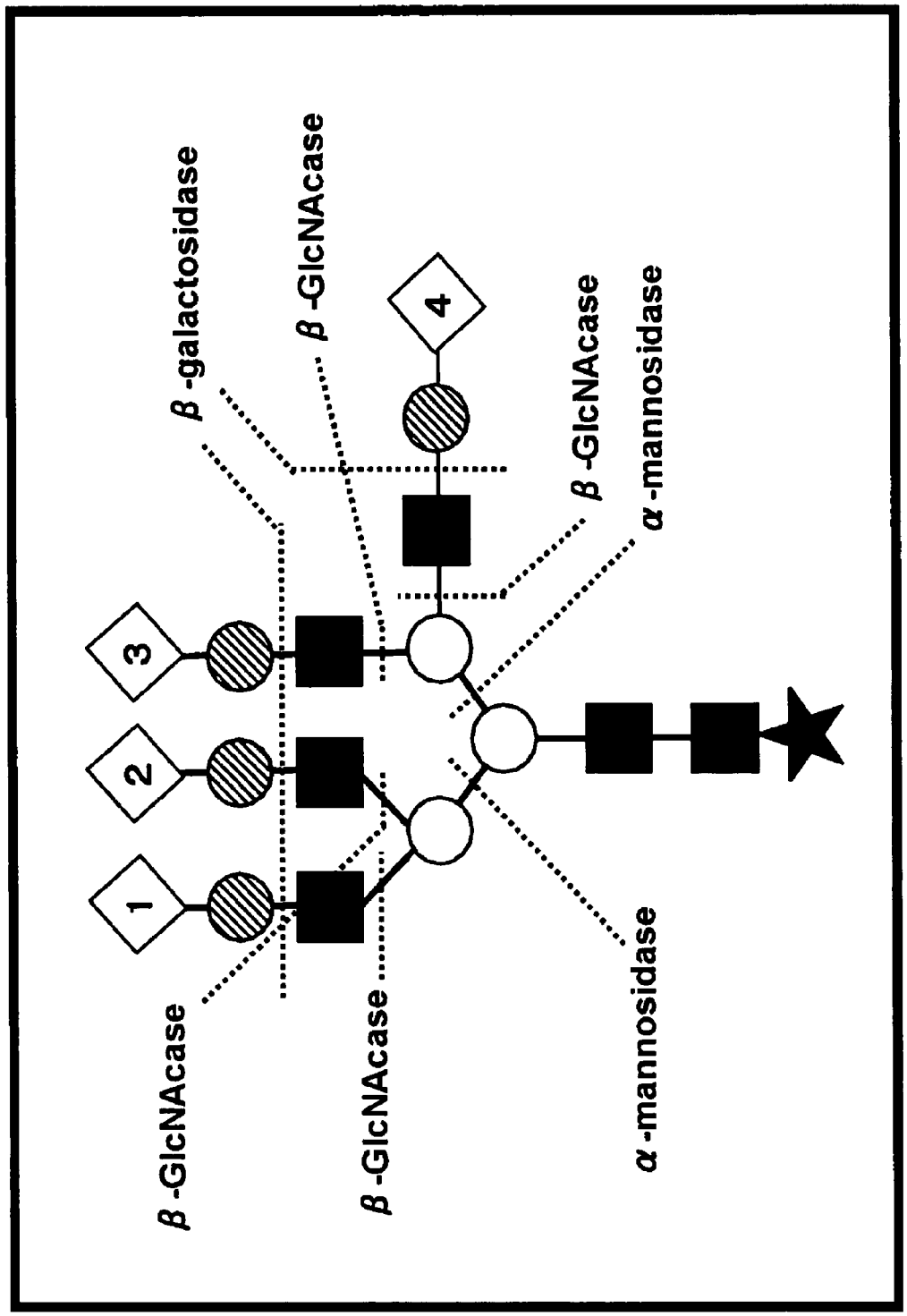
FIG. 17 shows the glycosidase cleavage site in a protected complex type sugar chain compound.

Preparation of Sugar Chain Compounds Having the Same Structure as that of Naturally Occurring Sugar Chain Generated from a Complex Type Sugar Chain First, a complex type sugar chain incorporating independently removable protecting groups on the non-reducing terminus sides of sugar chains is synthesized. Such a complex type sugar chain can easily be synthesized by using the method described in Seifert et al., Angewandte Chemie International Edition 39: 531-534 (2000), and a method well-known in the art. Next, by strategically cleaving the complex type sugar chain compound incorporating independently removable protecting groups introduced to the non-reducing terminus sides of sugar chains, with glycosidases, a sugar chain library is constructed (FIG. 15). Because the complex type sugar chain compound has the binding modes between sugar residues shown in FIG. 16, and also has the glycosidase cleavage sites shown in FIG. 17, appropriate reactions with these glycosidases result in various sugar chains.

Production Example 11

Figure 19:
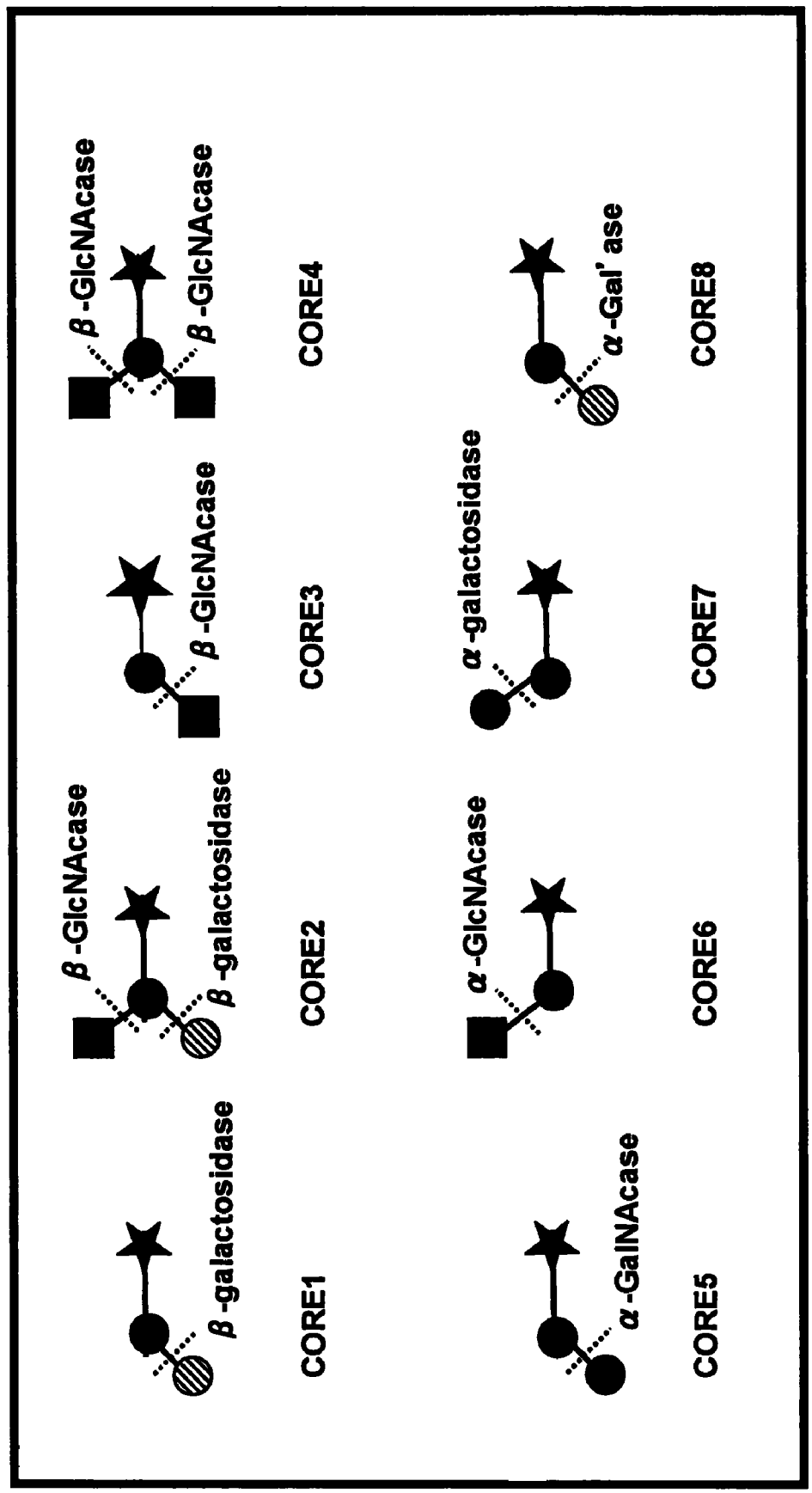
FIG. 19 shows glycosidases that cleave natural O-linked sugar chains CORE 1 to 8.
Figure 20:
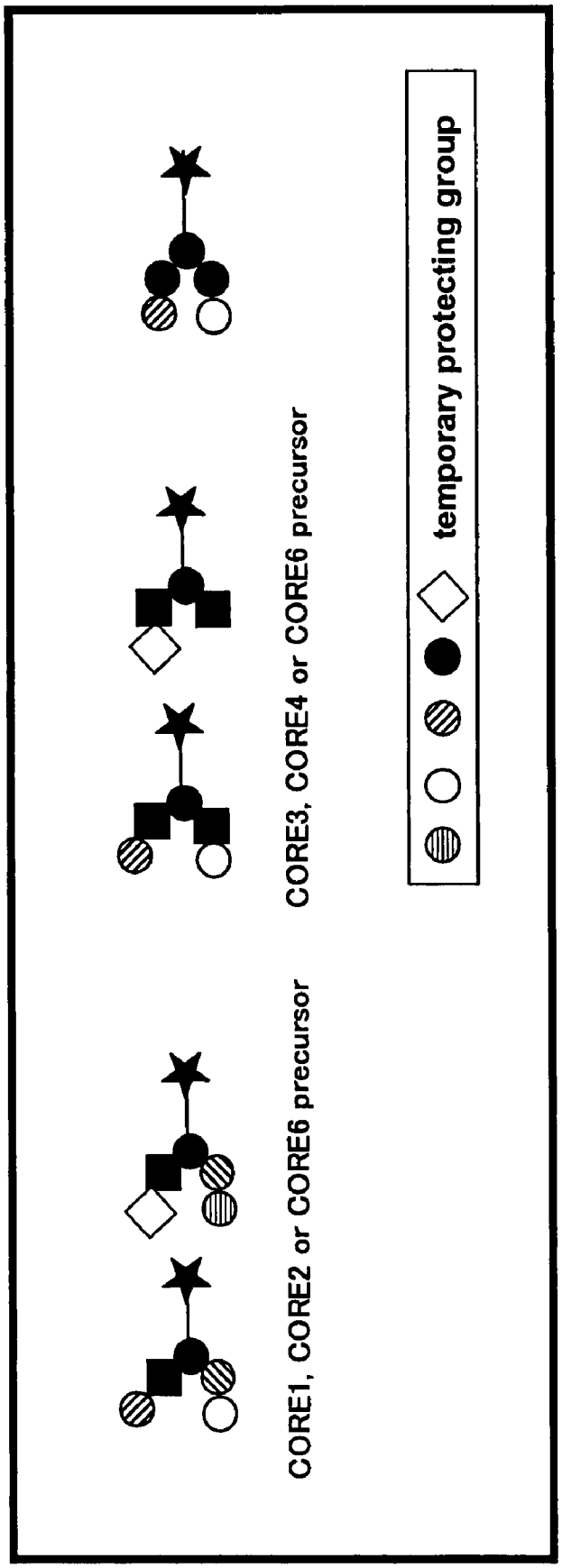
FIG. 20 shows the structure of a protected O-linked sugar chain.
Figure 21:
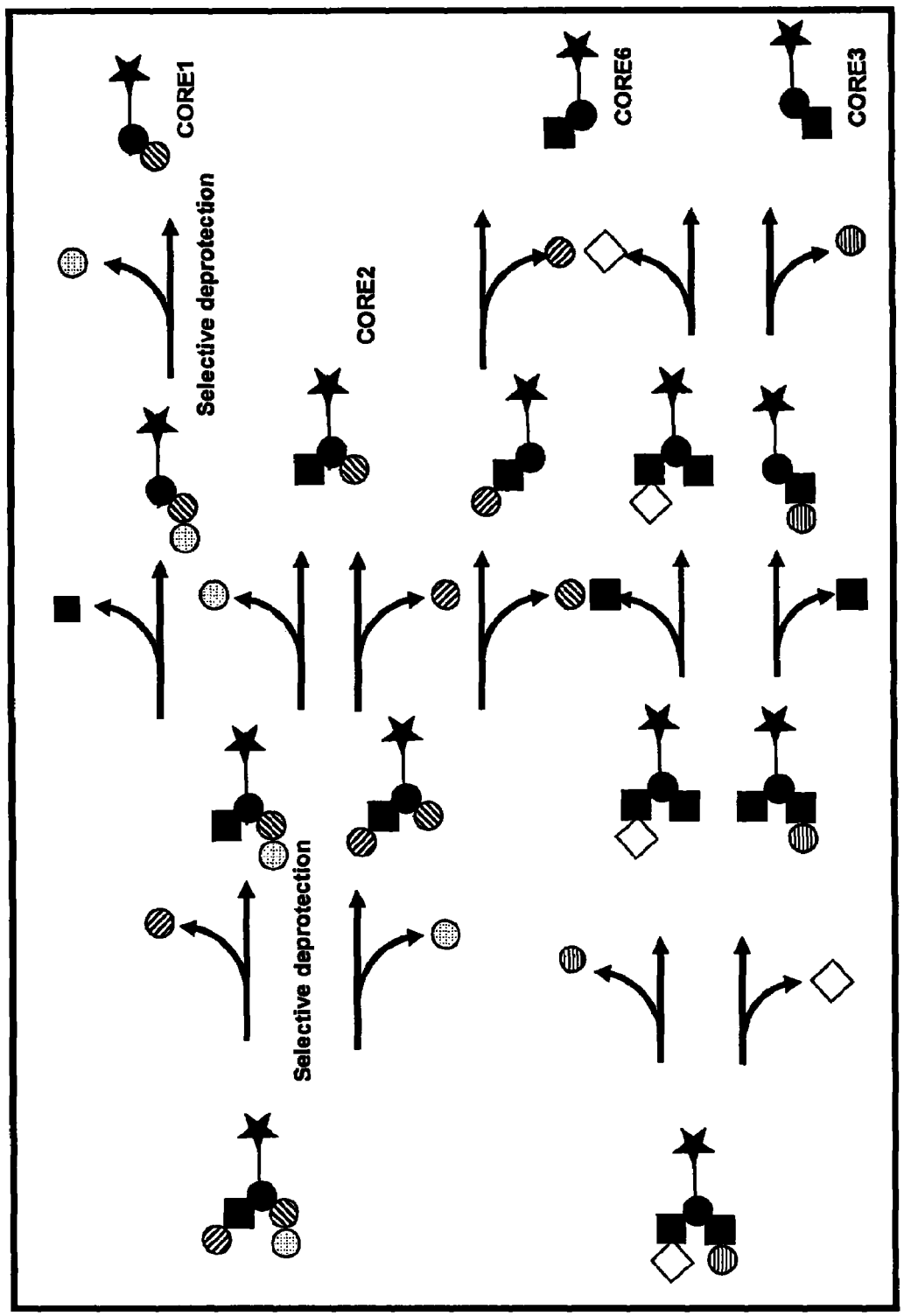
FIG. 21 shows an outline of the construction of various sugar chain compounds from a protected O-linked sugar chain compound. The symbols for sugar residues have the same definitions as those shown in FIGS. 18 and 19.

Preparation of Sugar Chain Compounds Having the Same Structure as that of Natural O-Linked Sugar Chain By preparing a starting sugar chain compound comprising all structures required for a sugar chain library, which incorporates independently removable protecting groups introduced to the non-reducing terminus sides of sugar chains, it is possible to convert the starting sugar chain compound to a desired sugar chain compound with no dependence on the selectivity of glycosidases. A natural O-linked sugar chain has the structures CORE 1 to 8 shown in FIG. 18 and the glycosidase cleavage sites shown in FIG. 19. Therefore, a sugar chain compound having the same structure as that of a natural O-linked sugar chain can be obtained by preparing an O-linked sugar chain compound incorporating individually removable protecting groups introduced to the non-reducing terminus sides of sugar chains, as shown in FIG. 20, and selectively cleaving the same with glycosidases, as shown in FIG. 21.

Figure 22:
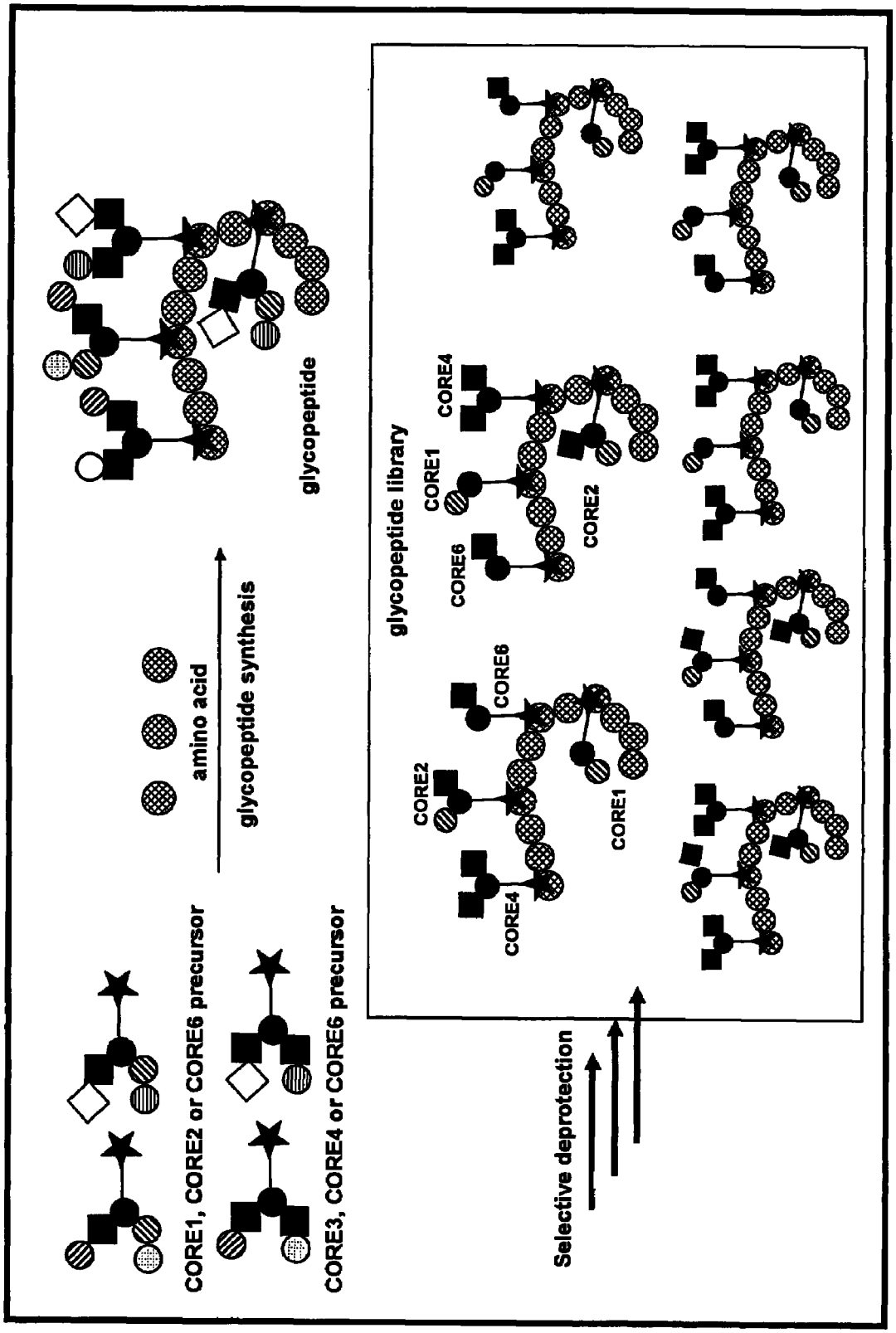
FIG. 22 shows an outline of the construction of a glycopeptide library.

A plurality of kinds of O-linked sugar chain compounds incorporating independently removable protecting groups (sugar residues) introduced to the non-reducing terminus sides of sugar chains (combinations of sugar residues that protect the terminus of O-linked sugar chain compound are mutually different) are synthesized, and these are bound to side chains of an amino acids (serine or threonine). The resulting amino acids having the sugar chain compound bound thereto are subjected to an amino acid polymerization reaction to yield a glycopeptide having the plurality of kinds of O-linked sugar chain compounds bound thereto. The polymerization of the amino acids having the sugar chain compounds bound thereto is carried out by, for example, the method described in Nakahara et al., Tetrahedron Letter 35: 3321-3324 (1994). Next, the glycopeptide having the plurality of kinds of O-linked sugar chain compounds bound thereto is selectively cleaved with glycosidases to yield a glycopeptide library (FIG. 22).

The specification is considered to be sufficient to enable one skilled in the art to practice the invention. It is understood that the examples and embodiments described herein are for illustrative purposes only. Indeed, various modifications of the invention in addition to those shown and described herein will become apparent to those skilled in the art from the foregoing description and fall within the scope of the appended claims.

The present application is base on Japanese patent application no. 2006-124468 filed in Japan on Apr. 27, 2006 and its content is herein incorporated by reference.

INDUSTRIAL APPLICABILITY

The protected sugar chain compound and salt thereof of the present invention and a library comprising the same are useful for enabling the specific and systematic production of various sugar chain compounds, and the like.

The sugar chain compound and salt thereof obtained by treating the protected sugar chain compound and salt thereof of the present invention and a library comprising the same, with glycosidases, and a library comprising the same are useful as intermediates in reactions for producing a naturally occurring sugar chain having biological activity or a population thereof, and the like.

The synthesis intermediate of the present invention is useful for enabling the easy preparation of the protected sugar chain compound and salt thereof of the present invention and a library comprising the same, and the like.

The present invention also provides a method of producing a sugar chain compound and salt thereof as described above, and a library comprising the same, and a reagent and kit comprising such a sugar chain compound and a salt thereof, and a library comprising the same, and the like.

What is claimed is:

1. A protected sugar chain compound or a salt thereof, which is represented by the formula (I) below:

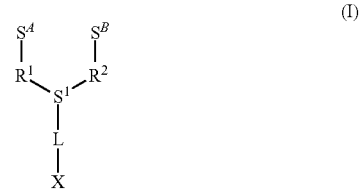

wherein
R$^1$ and R$^2$ are the same or different and each is a linear sugar chain with 3 to 10 sugar residues, or a branched sugar chain with 4 to 10 sugar residues, which has at a terminus thereof a protective sugar residue, and R$^1$ and R$^2$ comprise two or more sugar residues and one protective sugar residue, wherein the sugar residues within R$^1$ and R$^2$ are capable of being cleaved by the same exoglycosidases, S$^1$ is any sugar residue, S$^A$ and S$^B$ are the same or different sugar residues, L is a bond or a linear sugar chain with 1 to 5 sugar residues, X is
(i) absent, or
(ii) represents a hydroxyl-protecting group or amino acid residue bound to
any hydroxyl group in a sugar residue of L that has a reducing terminus, if L is a sugar chain, or any hydroxyl group in the sugar residue $S^1$, if L is a bond, or (iii) represents a structure wherein an amino group, or an amino-protecting group bound to the amino group, is substituted for any hydroxyl group in a sugar residue of L that has a reducing terminus, if L is a sugar chain, or any hydroxyl group in the sugar residue $S^1$, if L is a bond, and the sugar residue $S^A$ and the protective sugar residue within $R^1$ are cleaved by different exoglycosidases, and the sugar residue $S^B$ and the protective sugar residue within $R^2$ are cleaved by different exoglycosidases.

2. The protected sugar chain compound or salt thereof according to claim 1, which is characterized by one or more of the following features (a) to (d):

(a) $R^1$ and $R^2$ are linear sugar chains, and $S^A$ and $S^B$ are sugar residues different from each other;

(b) either $R^1$ or $R^2$ or both $R^1$ and $R^2$ are branched sugar chains having at a terminus thereof a protective sugar residue, and the protective sugar residue and the sugar residues $S^A$ and $S^B$ are different respectively;

(c) $R^1$ and $R^2$ are linear sugar chains, and the sugar residue in $R^1$, which is adjacent to $S^A$, and the sugar residue $S^A$ are different from each other, and the sugar residue in $R^2$, which is adjacent to $S^B$, and the sugar residue $S^B$ are different from each other;

(d) either $R^1$ or $R^2$ or both $R^1$ and $R^2$ are branched sugar chains having at a terminus thereof a protective sugar residue, and the protective sugar residue and the sugar residue adjacent thereto are different from each other, the sugar residue in $R^1$, which is adjacent to $S^A$, and the sugar residue $S^A$ are different from each other, and the sugar residue in $R^2$, which is adjacent to $S^B$, and the sugar residue $S^B$ are different from each other.

3. The protected sugar chain compound or salt thereof according to claim 1, which is characterized by one or more of the following features (a) to (c):

(a) $R^1$ and $R^2$ are linear sugar chains, and each of $R^1$ and $R^2$ is composed of one kind of sugar residue;

(b) either $R^1$ or $R^2$ or both $R^1$ and $R^2$ are branched sugar chains having at a terminus thereof a protective sugar residue, and each of $R^1$ and $R^2$ is composed of one kind of sugar residue except the protective sugar residue;

(c) the sugar residue in $R^1$, which is adjacent to $S^A$, and the sugar residue in $R^2$, which is adjacent to $S^B$, are cleaved by the same exoglycosidase.

4. The protected sugar chain compound or salt thereof according to claim 1, wherein the number of sugar residues in each of $R^1$ and $R^2$ is 3 to 8.

5. The protected sugar chain compound or salt thereof according to claim 1, wherein $R^1$ and $R^2$ are the same or different and each is either the formulas ($v^3$) or ($v^{14}$) below:

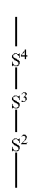

(v³)

-continued

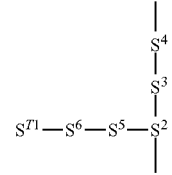

(v¹⁴)

wherein $S^2$ to $S^4$ in the formula ($v^3$) and $S^2$ to $S^6$ in the formula ($v^{14}$) are any sugar residues, and $S^{T1}$ in the formula ($v^{14}$) is the protective sugar residue.

6. The protected sugar chain compound or salt thereof according to claim 5, wherein the sugar residues $S^A$ and $S^B$ in the formula (I), the sugar residues $S^2$ to $S^4$ in the formula ($v^3$), and the sugar residues $S^2$ to $S^6$ and $S^{T1}$ in the formula ($v^{14}$) are selected from the group consisting of D-glucose, D-mannose, D-galactose, D-xylose, N-acetyl-D-glucosamine, N-acetyl-D-galactosamine, L-fucose and sialic acid.

7. The protected sugar chain compound or salt thereof according to claim 1, wherein the protected sugar chain compound is a compound represented by the formula (Ia) below:

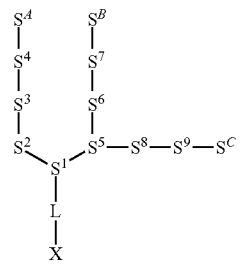

(Ia)

wherein $S^1$ to $S^9$ are any sugar residues, $S^A$, $S^B$ and $S^C$ are the same or different sugar residues, L is a bond or a linear sugar chain with 1 to 10 sugar residues, X is (i) absent, or (ii) represents a hydroxyl-protecting group or amino acid residue bound to any hydroxyl group in a sugar residue of L that has a reducing terminus, if L is a sugar chain, or any hydroxyl group in the sugar residue $S^1$, if L is a bond, or (iii) represents a structure wherein an amino group, or an amino-protecting group bound to the amino group, is substituted for any hydroxyl group in a sugar residue of L that has a reducing terminus, if L is a sugar chain, or any hydroxyl group in the sugar residue $S^1$, if L is a bond, and the sugar residues $S^A$, $S^B$, and $S^C$ are cleaved by different exoglycosidases, respectively.

8. The protected sugar chain compound or salt thereof according to claim 1, wherein the protected sugar chain compound is a compound represented by the formula (II) below:

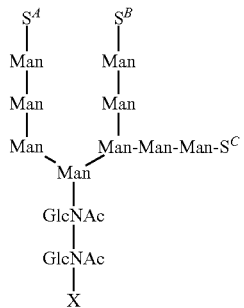
(II)

wherein

Man represents D-mannose,

GlcNAc represents N-acetyl-D-glucosamine, $S^A$, $S^B$ and $S^C$ are the same or different sugar residues, X is (i) absent, or (ii) represents a hydroxyl-protecting group or amino acid residue bound to any hydroxyl group in GlcNAc, or (iii) represents a structure wherein an amino group, or an amino-protecting group bound to the amino group, is substituted for any hydroxyl group in GlcNAc, and the sugar residues $S^A$, $S^B$, and $S^C$ are cleaved by different exoglycosidases, respectively.

9. The protected sugar chain compound or salt thereof according to claim 8, wherein all binding modes between Man and Man, between GlcNAc and GlcNAc, and between Man and GlcNAc, are the same as the binding mode of natural high mannose type sugar chain compound.

10. The protected sugar chain compound or salt thereof according to claim 8, wherein the sugar residues $S^A$, $S^B$ and $S^C$ are different sugar residues.

11. The protected sugar chain compound or salt thereof according to claim 8, wherein $S^A$ is D-glucose.

12. A sugar chain compound of any of the formulas (IIa1) to (IIa4), (IIa8), (IIb4) to (IIb5), and (IIb14) below or a salt thereof:

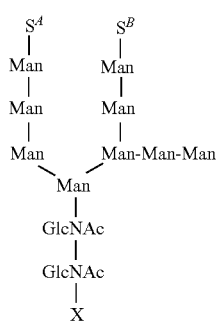
(IIa1)

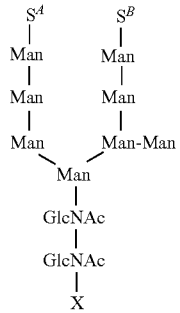
(IIa2)

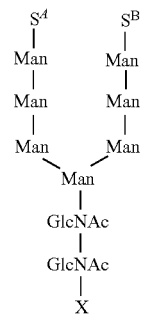
(IIa3)

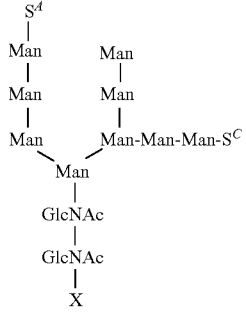
(IIa4)

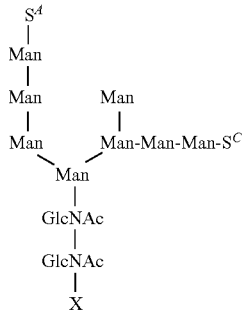
(IIa8)

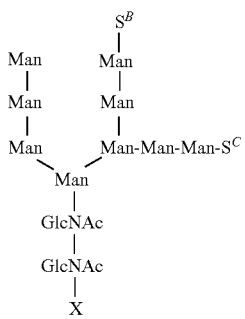
(IIb4)

-continued

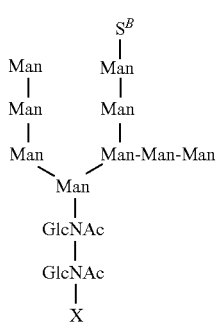
(IIb5)

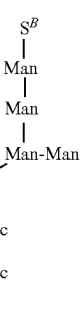
(IIb14)

wherein

Man represents D-mannose,

GlcNAc represents N-acetyl-D-glucosamine,

X is (i) absent, or (ii) represents a hydroxyl-protecting group or amino acid residue bound to any hydroxyl group in GlcNAc, or (iii) represents a structure wherein an amino group, or an amino-protecting group bound to the amino group, is substituted for any hydroxyl group in GlcNAc, and the sugar residues $S^A$, $S^B$, and $S^C$ are different respectively, and are selected from the group consisting of D-glucose, D-galactose, D-xylose, N-acetyl-D-glucosamine, N-acetyl-D-galactosamine, L-fucose, and sialic acid.

13. A reagent or kit, which comprises the sugar chain compound or salt thereof according to claim 1.

14. A reagent or kit, which comprises the sugar chain compound or salt thereof according to claim 12.

15. The reagent or kit according to claim 13, which further comprises one or more glycosidases.

* * * * *